US006387637B1

(12) United States Patent
Levin et al.

(10) Patent No.: US 6,387,637 B1
(45) Date of Patent: May 14, 2002

(54) HERBICIDE TARGET GENES AND METHOD

(75) Inventors: Joshua Z. Levin; Gregory J. Budziszewski, both of Durham; Sharon L. Potter, Raleigh, all of NC (US); Lynette M. Wegrich, San Jose, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/480,921

(22) Filed: Jan. 11, 2000

Related U.S. Application Data

(60) Provisional application No. 60/240,917, filed on Jan. 15, 1999, provisional application No. 60/183,017, filed on Jan. 26, 1999, provisional application No. 60/198,245, filed on Feb. 3, 1999, provisional application No. 60/304,202, filed on Feb. 18, 1999, and provisional application No. 60/155,231, filed on Mar. 30, 1999.

(51) Int. Cl.$^7$ .............................................. G01N 33/53

(52) U.S. Cl. ........................ 435/7.1; 435/7.1; 530/350; 530/380

(58) Field of Search ................................ 530/350, 300; 435/7.1

(56) References Cited

U.S. PATENT DOCUMENTS

| | | | |
|---|---|---|---|
| 5,013,659 A | 5/1991 | Bedbrook et al. | 435/172.3 |
| 5,162,602 A | 11/1992 | Somers et al. | 800/235 |
| 5,919,999 A | 7/1999 | Ko et al. | 800/298 |
| 6,281,017 B1 | 8/2001 | Croteau et al. | 435/468 |
| 6,303,365 B1 | 10/2001 | Martin et al. | 435/252.3 |

FOREIGN PATENT DOCUMENTS

EP 0 154 204 9/1985

OTHER PUBLICATIONS

Schwender et al., Accession No.: T52570, 1999.*
Kuzuyama et al., Tetrahedron Letters, vol. 39, pp. 7913–7916, 1998.*
Craigen, W.J. et al., "Bacterial peptide chain release factors: Conserved primary structure and possible frameshift regulation of release factor 2," Proc. Natl. Acad. Sci. USA, 82: pp. 3616–3620 (1985).
Craigen, W.J. et al., "The function, structure and regulation of E. coli peptide chain release factors," Biochimie, 69: pp. 1031–1041 (1987).
Errampalli, D. et al., "Embryonic Lethals and T–DNA Insertional Mutagenesis in Arabidopsis," The Plant Cell, 3: pp. 149–157 (1991).
Gautier, T. et al., "Nucleolar KKE/D Repeat Proteins Nop56p and Nop58p Interact with Nop1p and Are Required for Ribosome Biogenesis," Molecular and Cellular Biology, 17(12): pp. 7088–7098 (1997).

Ito, K. et al., "Single amino acid substitution in prokaryote polypeptide release factor 2 permits it to terminate translation at all three stop codons," Proc. Natl. Acad. Sci, USA, 95: pp. 8165–8169 (1998).
Johzuka, K and Ogawa, H., "Interaction of Mre11 and Rad50: Two Proteins Required for DNA Repair and Meiosis–Specific Double–Strand Break Formation in Saccharomyces cerevisiae," Genetics, 139: pp. 1521–1532 (1995).
Jurgens, G. et al., "Genetic analysis of pattern formation in the Arabidopsis embryo," The Company of Biologists Limited, Development Supplement 1, pp. 27–38 (1991).
Ko, K. et al., "Isolation and Characterization of a cDNA Clone Encoding a Member of the Com44/Cim44 Envelope Components of the Chloroplast Protein Import Apparatus," Journal of Biological Chemistry, 270(48): pp. 28601–28608 (1995).
Koncz, C. et al., "High–frequency T–DNA–mediated gene tagging in plants," Proc. Natl. Acad. Sci. USA, 86: pp. 8467–8471 (1989).
Mayer, U. et al., "Mutations affecting body organization in the Arabidopsis embryo," Nature, 353: pp. 402–407 (1991).
Morin, P.J. et al., "Genetic Analysis of Growth Inhibition by GAL4–IκB–α in Saccharomyces cerevisiae," Cell Growth & Differentiation, 6: pp. 789–798 (1998).
Pang, P. et al., "A Component of the Chloroplast Protein Import Apparatus Functions in Bacteria," Journal of Biological Chemistry, 272(41): pp. 25623–25627 (1997).
Paull, T.T. and Gellert, M., "The 3' to 5' Exonuclease Activity of Mre11 Faciliates Repair of DNA Double–Strand Breaks," Molecular Cell, 1: pp. 969–979 (1998).
Rzepecki, R. et al., "Interaction of the Pisum sativum nuclear matrix proteins with SAR DNA," Acta Biochimica Polonica, 42(1): pp. 75–82 (1995).
Schwender, J. et al., "Cloning and heterologous expression of a cDNA encoding 1–deoxy–D–xylulose–5–phosphate reductoisomerase of Arabidopsis thaliana," FEBS Letters, 455: pp. 140–144 (1999).
Stahl, T. et al., "Tic40, a New "Old" Subunit of the Chloroplast Protein Import Translocon," Journal of Biological Chemistry, 274(52): pp. 37467–37472 (1991).

(List continued on next page.)

Primary Examiner—Karen Cochrane Carlson
Assistant Examiner—Hope A. Robinson
(74) Attorney, Agent, or Firm—J. Timothy Meigs; Edouard G. Lebel; Larry W. Stults

(57) ABSTRACT

The invention relates to genes isolated from Arabidopsis that code for proteins essential for seedling growth. The invention also includes the methods of using these proteins to discover new herbicides, based on the essentiality of the genes for normal growth and development. The invention can also be used in a screening assay to identify inhibitors that are potential herbicides. The invention is also applied to the development of herbicide tolerant plants, plant tissues, plant seeds, and plant cells.

1 Claim, No Drawings

OTHER PUBLICATIONS

Takahashi, S. et al., "A 1–deoxy–D–xylulose 5–phosphate reductoisomerase catalyzing the formation of 2–C–methyl–D–erythritol 4–phosphate in an alternative nonmevalonate pathway for terpenoid biosynthesis," Proc. Acad. Sci. USA, 95: pp. 9879–9884 (1998).

Weidenhammer, E.M. et al., "Prp31p Promotes the Association of the U4/U6.U5 Tri–snRNP with Prespliceosomes to Form Spliceosomes in *Saccharomyces Cerevisiae*," Molecular and Cellular Biology, 17(7): pp. 3580–3588 (1997).

Weidenhammer, E.M. et al., "The PRP31 gene encodes a novel protein required for pre–mRNA splicing in *Saccaromyces cerevisiae* ," Nucleic Acids Research, 24(6): pp. 3580–3588 (1996).

Wu, C. et al., "Identification of Chloroplast Envelope Proteins in Close Physical Proximity to a Partially Translocated Chimeric Precursor Protein," Journal kof Biological Chemistry, 269(51): pp. 32264–32271 (1994).

Topping, J.F., "Mutations in the HYDRA1 gene of Arabidopsis perturb cell shape and disrupt embryonic and seeding morphogenesis," Development, 124: pp. 4415–4424 (1997).

Zhou, D.–X. et al., "COP1b, and isoform of COP1 generated by alternative splicing, has a negative effect on COP1 function in regulating light–dependent seeding development in Arabidopsis," Molecular & General Genetics, 257: pp. 387–391 (1998).

EMBL Sequence Accession No. B24357 Oct. 13, 1997.

International Search Report for application No. PCT/EP00/00246.

* cited by examiner

SEQUENCE LISTING

<160> NUMBER OF SEQ ID NOS: 29

<210> SEQ ID NO 1
<211> LENGTH: 1119
<212> TYPE: DNA
<213> ORGANISM: Arabidopsis thaliana
<220> FEATURE:
<221> NAME/KEY: CDS
<222> LOCATION: (1)..(1119)

<400> SEQUENCE: 1

```
atg gat gac atg gac acc gtc tac aag caa t tg gga ttg ttt tca cta        48
Met Asp Asp Met Asp Thr Val Tyr Lys Gln L eu Gly Leu Phe Ser Leu
 1               5                  10                  15 aag aag aag att aaa gat gtt gtt ctt aag g ct gag atg ttt gca ccg        96
Lys Lys Lys Ile Lys Asp Val Val Leu Lys A la Glu Met Phe Ala Pro
             20                  25                  30 gat gct ctt gag ctt gaa gaa gag cag tgg a ta aag caa gaa gaa aca       144
Asp Ala Leu Glu Leu Glu Glu Glu Gln Trp I le Lys Gln Glu Glu Thr
         35                  40                  45 atg cgt tac ttt gat tta tgg gat gat ccc g ct aaa tct gat gag att       192
Met Arg Tyr Phe Asp Leu Trp Asp Asp Pro A la Lys Ser Asp Glu Ile
     50                  55                  60 ctt ctc aaa tta gct gat cga gct aaa gca g tc gat tcc ctc aaa gac       240
Leu Leu Lys Leu Ala Asp Arg Ala Lys Ala V al Asp Ser Leu Lys Asp
 65                  70                  75                  80 ctc aaa tac aag gct gaa gaa gct aag ctg a tc ata caa ttg ggt gag       288
Leu Lys Tyr Lys Ala Glu Glu Ala Lys Leu I le Ile Gln Leu Gly Glu
                 85                  90                  95 atg gat gct ata gat tac agt ctc ttt gag c aa gcc tat gat tca tca       336
Met Asp Ala Ile Asp Tyr Ser Leu Phe Glu G ln Ala Tyr Asp Ser Ser
            100                 105                 110 ctc gat gta agt aga tcg ttg cat cac tat g ag atg tct aag ctt ctt       384
Leu Asp Val Ser Arg Ser Leu His His Tyr G lu Met Ser Lys Leu Leu
        115                 120                 125 agg gat caa tat gac gct gaa ggc gct tgt a tg att atc aaa tct gga       432
Arg Asp Gln Tyr Asp Ala Glu Gly Ala Cys M et Ile Ile Lys Ser Gly
    130                 135                 140 tct cca ggc gca aaa tct cag ata tgg aca g ag caa gtt gta agt atg       480
Ser Pro Gly Ala Lys Ser Gln Ile Trp Thr G lu Gln Val Val Ser Met
145                 150                 155                 160
```

```
tat atc aaa tgg gca gaa agg cta ggc caa a ac gcg cgg gtg gct gag      528
Tyr Ile Lys Trp Ala Glu Arg Leu Gly Gln A sn Ala Arg Val Ala Glu
                165                 170                 175 aaa tgt agt tta ttg agt aat aaa agt ggc g ta agt tca gcc acg ata      576
Lys Cys Ser Leu Leu Ser Asn Lys Ser Gly V al Ser Ser Ala Thr Ile
                180                 185                 190 gag ttt gaa ttc gag ttt gct tat ggt tat c tc tta ggt gag cga ggt      624
Glu Phe Glu Phe Glu Phe Ala Tyr Gly Tyr L eu Leu Gly Glu Arg Gly
                195                 200                 205 gtg cac cgc ctt atc ata agt tcc act tct a at gag gaa tgt tca gcg      672
Val His Arg Leu Ile Ile Ser Ser Thr Ser A sn Glu Glu Cys Ser Ala
    210                 215                 220 act gtt gat atc ata cca cta ttc ttg aga g ca tct cct gat ttt gaa      720
Thr Val Asp Ile Ile Pro Leu Phe Leu Arg A la Ser Pro Asp Phe Glu
225                 230                 235                 240 gta aag gaa ggt gat ttg att gta tcg tat c ct gca aaa gag gat cac      768
Val Lys Glu Gly Asp Leu Ile Val Ser Tyr P ro Ala Lys Glu Asp His
                245                 250                 255 aaa ata gct gag aat atg gtt tgt atc cac c at att ccg agt gga gta      816
Lys Ile Ala Glu Asn Met Val Cys Ile His H is Ile Pro Ser Gly Val
                260                 265                 270 aca cta caa tct tca gga gaa aga aac cgg t tt gca aac agg atc aaa      864
Thr Leu Gln Ser Ser Gly Glu Arg Asn Arg P he Ala Asn Arg Ile Lys
                275                 280                 285 gct cta aac cgg ttg aag gcg aag cta ctt g tg ata gca aaa gag caa      912
Ala Leu Asn Arg Leu Lys Ala Lys Leu Leu V al Ile Ala Lys Glu Gln
                290                 295                 300 aag gtt tcg gat gta aat aaa atc gac agc a ag aac att ttg gaa ccg      960
Lys Val Ser Asp Val Asn Lys Ile Asp Ser L ys Asn Ile Leu Glu Pro
305                 310                 315                 320 cgg gaa gaa acc agg agt tat gtc tct aag g gt cac aag atg gtg gtt     1008
Arg Glu Glu Thr Arg Ser Tyr Val Ser Lys G ly His Lys Met Val Val
                325                 330                 335 gat aga aaa acc ggt tta gag att ctg gac c tg aaa tcg gtc ttg gat     1056
Asp Arg Lys Thr Gly Leu Glu Ile Leu Asp L eu Lys Ser Val Leu Asp
                340                 345                 350 gga aac att gga cca ctc ctt gga gct cat a tt agc atg aga aga tca     1104
Gly Asn Ile Gly Pro Leu Leu Gly Ala His I le Ser Met Arg Arg Ser
                355                 360                 365 att gat gcg att tag                                                  1119
Ile Asp Ala Ile
    370

<210> SEQ ID NO 2
<211> LENGTH: 372
<212> TYPE: PRT
<213> ORGANISM: Arabidopsis thaliana

<400> SEQUENCE: 2

Met Asp Asp Met Asp Thr Val Tyr Lys Gln L eu Gly Leu Phe Ser Leu
1               5                   10                  15

Lys Lys Lys Ile Lys Asp Val Val Leu Lys A la Glu Met Phe Ala Pro
                20                  25                  30

Asp Ala Leu Glu Leu Glu Glu Glu Gln Trp I le Lys Gln Glu Glu Thr
            35                  40                  45

Met Arg Tyr Phe Asp Leu Trp Asp Asp Pro A la Lys Ser Asp Glu Ile
        50                  55                  60

Leu Leu Lys Leu Ala Asp Arg Ala Lys Ala V al Asp Ser Leu Lys Asp
65                  70                  75                  80
```

-continued

```
Leu Lys Tyr Lys Ala Glu Glu Ala Lys Leu Ile Ile Gln Leu Gly Glu
             85                  90                  95

Met Asp Ala Ile Asp Tyr Ser Leu Phe Glu Gln Ala Tyr Asp Ser Ser
            100                 105                 110

Leu Asp Val Ser Arg Ser Leu His His Tyr Glu Met Ser Lys Leu Leu
        115                 120                 125

Arg Asp Gln Tyr Asp Ala Glu Gly Ala Cys Met Ile Ile Lys Ser Gly
    130                 135                 140

Ser Pro Gly Ala Lys Ser Gln Ile Trp Thr Glu Gln Val Val Ser Met
145                 150                 155                 160

Tyr Ile Lys Trp Ala Glu Arg Leu Gly Gln Asn Ala Arg Val Ala Glu
                165                 170                 175

Lys Cys Ser Leu Leu Ser Asn Lys Ser Gly Val Ser Ser Ala Thr Ile
            180                 185                 190

Glu Phe Glu Phe Glu Phe Ala Tyr Gly Tyr Leu Leu Gly Glu Arg Gly
        195                 200                 205

Val His Arg Leu Ile Ile Ser Ser Thr Ser Asn Glu Glu Cys Ser Ala
    210                 215                 220

Thr Val Asp Ile Ile Pro Leu Phe Leu Arg Ala Ser Pro Asp Phe Glu
225                 230                 235                 240

Val Lys Glu Gly Asp Leu Ile Val Ser Tyr Pro Ala Lys Glu Asp His
                245                 250                 255

Lys Ile Ala Glu Asn Met Val Cys Ile His His Ile Pro Ser Gly Val
            260                 265                 270

Thr Leu Gln Ser Ser Gly Glu Arg Asn Arg Phe Ala Asn Arg Ile Lys
        275                 280                 285

Ala Leu Asn Arg Leu Lys Ala Lys Leu Leu Val Ile Ala Lys Glu Gln
    290                 295                 300

Lys Val Ser Asp Val Asn Lys Ile Asp Ser Lys Asn Ile Leu Glu Pro
305                 310                 315                 320

Arg Glu Glu Thr Arg Ser Tyr Val Ser Lys Gly His Lys Met Val Val
                325                 330                 335

Asp Arg Lys Thr Gly Leu Glu Ile Leu Asp Leu Lys Ser Val Leu Asp
            340                 345                 350

Gly Asn Ile Gly Pro Leu Leu Gly Ala His Ile Ser Met Arg Arg Ser
        355                 360                 365

Ile Asp Ala Ile
    370
```

<210> SEQ ID NO 3
<211> LENGTH: 1458
<212> TYPE: DNA
<213> ORGANISM: Arabidopsis thaliana
<220> FEATURE:
<221> NAME/KEY: CDS
<222> LOCATION: (1)..(1458)

<400> SEQUENCE: 3

```
atg gca act ctt gaa gat tct ttc ctt gct gat ttg gac gag tta tct    48
Met Ala Thr Leu Glu Asp Ser Phe Leu Ala Asp Leu Asp Glu Leu Ser
  1               5                  10                  15 gac aat gaa gca gaa ttg gac gag aat gat ggt gat gtt gga aag gaa    96
Asp Asn Glu Ala Glu Leu Asp Glu Asn Asp Gly Asp Val Gly Lys Glu
             20                  25                  30 gaa gaa gat gtt gat atg gat atg gct gat tta gag aca ctt aac tat   144
Glu Glu Asp Val Asp Met Asp Met Ala Asp Leu Glu Thr Leu Asn Tyr
        35                  40                  45
```

```
gat gat ctc gat aat gtt tct aag ctg cag a ag agt cag aga tat gct        192
Asp Asp Leu Asp Asn Val Ser Lys Leu Gln L ys Ser Gln Arg Tyr Ala
         50                  55                  60 gat att atg cat aaa gta gag gag gct ctt g gg aaa gat tct gat gga        240
Asp Ile Met His Lys Val Glu Glu Ala Leu G ly Lys Asp Ser Asp Gly
 65                  70                  75                  80 gct gag aaa gga act gtc ttg gaa gat gat c ct gag tat aag ctt att        288
Ala Glu Lys Gly Thr Val Leu Glu Asp Asp P ro Glu Tyr Lys Leu Ile
                 85                  90                  95 gtg gat tgt aat cag ctt tcg gtc gat att g ag aat gaa atc gtt att        336
Val Asp Cys Asn Gln Leu Ser Val Asp Ile G lu Asn Glu Ile Val Ile
            100                 105                 110 gtc cac aac ttt atc aaa gac aag tac aag c tt aag ttt caa gag ctt        384
Val His Asn Phe Ile Lys Asp Lys Tyr Lys L eu Lys Phe Gln Glu Leu
                115                 120                 125 gag tcg ttg gtt cat cac cct att gac tat g ca tgt gtt gtg aag aag        432
Glu Ser Leu Val His His Pro Ile Asp Tyr A la Cys Val Val Lys Lys
        130                 135                 140 att ggg aat gag acg gat ttg gct ctt gtt g at ctc gct gac ctt ctt        480
Ile Gly Asn Glu Thr Asp Leu Ala Leu Val A sp Leu Ala Asp Leu Leu
145                 150                 155                 160 cct tca gct att atc atg gtt gtt tca gtt a ct gct tta act acg aaa        528
Pro Ser Ala Ile Ile Met Val Val Ser Val T hr Ala Leu Thr Thr Lys
                165                 170                 175 ggg agt gca ctg cca gag gat gtt ttg caa a ag gtg tta gag gct tgt        576
Gly Ser Ala Leu Pro Glu Asp Val Leu Gln L ys Val Leu Glu Ala Cys
            180                 185                 190 gat cgg gct tta gat ctt gat tcc gca agg a ag aag gtc ctt gag ttt        624
Asp Arg Ala Leu Asp Leu Asp Ser Ala Arg L ys Lys Val Leu Glu Phe
        195                 200                 205 gtt gaa agt aag atg gga tct att gca cct a at ctt tct gct att gtt        672
Val Glu Ser Lys Met Gly Ser Ile Ala Pro A sn Leu Ser Ala Ile Val
    210                 215                 220 ggg agt gct gtt gca gcc aaa ctc atg ggg a ct gct gga ggt ttg tca        720
Gly Ser Ala Val Ala Ala Lys Leu Met Gly T hr Ala Gly Gly Leu Ser
225                 230                 235                 240 gca ctt gct aaa atg cct gcg tgt aat gtt c aa gtt ctt ggc cac aag        768
Ala Leu Ala Lys Met Pro Ala Cys Asn Val G ln Val Leu Gly His Lys
                245                 250                 255 agg aag aac ctt gct ggg ttt tct tct gca a cg tct cag tcc cgt gtg        816
Arg Lys Asn Leu Ala Gly Phe Ser Ser Ala T hr Ser Gln Ser Arg Val
            260                 265                 270 ggt tat ctg gag cag aca gag att tac caa a gc acg cct cct gga ctt        864
Gly Tyr Leu Glu Gln Thr Glu Ile Tyr Gln S er Thr Pro Pro Gly Leu
        275                 280                 285 cag gct cgc gct ggc agg ctc gtg gct gca a aa tca act ttg gca gca        912
Gln Ala Arg Ala Gly Arg Leu Val Ala Ala L ys Ser Thr Leu Ala Ala
    290                 295                 300 aga gtt gat gct act aga ggg gat ccg tta g gg ata agt gga aaa gct        960
Arg Val Asp Ala Thr Arg Gly Asp Pro Leu G ly Ile Ser Gly Lys Ala
305                 310                 315                 320 ttc agg gag gag atc cgt aag aag att gag a aa tgg caa gaa cct cct       1008
Phe Arg Glu Glu Ile Arg Lys Lys Ile Glu L ys Trp Gln Glu Pro Pro
                325                 330                 335 cct gca aga cag cct aag cca ctt cct gtt c ct gat tct gaa ccg aag       1056
Pro Ala Arg Gln Pro Lys Pro Leu Pro Val P ro Asp Ser Glu Pro Lys
            340                 345                 350 aaa aga agg ggt ggt cgc cgt cta aga aaa a tg aaa gaa agg tat caa       1104
Lys Arg Arg Gly Gly Arg Arg Leu Arg Lys M et Lys Glu Arg Tyr Gln
```

```
                355                360                365
gta aca gat atg agg aag ctg gcc aac aga a tg gcg ttt ggt aca cct    1152
Val Thr Asp Met Arg Lys Leu Ala Asn Arg M et Ala Phe Gly Thr Pro
        370                375                380 gaa gag agc tcc ctc ggt gat gga cta gga g aa ggt tat gga atg ctt    1200
Glu Glu Ser Ser Leu Gly Asp Gly Leu Gly G lu Gly Tyr Gly Met Leu
385                390                395                400 ggc cag gca gga agc aac agg ctg cga gta t cc agt gtt ccg agc aag    1248
Gly Gln Ala Gly Ser Asn Arg Leu Arg Val S er Ser Val Pro Ser Lys
                405                410                415 ctt aag att aat gct aag gtc gcc aaa aag c tt aaa gaa agg cag tat    1296
Leu Lys Ile Asn Ala Lys Val Ala Lys Lys L eu Lys Glu Arg Gln Tyr
            420                425                430 gcg ggt ggt gcg act acc tct ggt ttg aca t cg agc ctg gct ttc act    1344
Ala Gly Gly Ala Thr Thr Ser Gly Leu Thr S er Ser Leu Ala Phe Thr
        435                440                445 cct gtg cag gga ata gag ttg tgc aat cct c ag cag gct tta gga tta    1392
Pro Val Gln Gly Ile Glu Leu Cys Asn Pro G ln Gln Ala Leu Gly Leu
    450                455                460 gga agt ggg act caa agc act tac ttc tca g ag tca gga acc ttc tcg    1440
Gly Ser Gly Thr Gln Ser Thr Tyr Phe Ser G lu Ser Gly Thr Phe Ser
465                470                475                480 aag ctg aag aag atc taa                                             1458
Lys Leu Lys Lys Ile
                485

<210> SEQ ID NO 4
<211> LENGTH: 485
<212> TYPE: PRT
<213> ORGANISM: Arabidopsis thaliana

<400> SEQUENCE: 4

Met Ala Thr Leu Glu Asp Ser Phe Leu Ala A sp Leu Asp Glu Leu Ser
1               5                   10                  15

Asp Asn Glu Ala Glu Leu Asp Glu Asn Asp G ly Asp Val Gly Lys Glu
            20                  25                  30

Glu Glu Asp Val Asp Met Asp Met Ala Asp L eu Glu Thr Leu Asn Tyr
        35                  40                  45

Asp Asp Leu Asp Asn Val Ser Lys Leu Gln L ys Ser Gln Arg Tyr Ala
    50                  55                  60

Asp Ile Met His Lys Val Glu Glu Ala Leu G ly Lys Asp Ser Asp Gly
65                  70                  75                  80

Ala Glu Lys Gly Thr Val Leu Glu Asp Pro G lu Tyr Lys Leu Ile
                85                  90                  95

Val Asp Cys Asn Gln Leu Ser Val Asp Ile G lu Asn Glu Ile Val Ile
            100                 105                 110

Val His Asn Phe Ile Lys Asp Lys Tyr Lys L eu Lys Phe Gln Glu Leu
        115                 120                 125

Glu Ser Leu Val His His Pro Ile Asp Tyr A la Cys Val Val Lys Lys
    130                 135                 140

Ile Gly Asn Glu Thr Asp Leu Ala Leu Val A sp Leu Ala Asp Leu Leu
145                 150                 155                 160

Pro Ser Ala Ile Ile Met Val Val Ser Val T hr Ala Leu Thr Thr Lys
                165                 170                 175

Gly Ser Ala Leu Pro Glu Asp Val Leu Gln L ys Val Leu Glu Ala Cys
            180                 185                 190

Asp Arg Ala Leu Asp Leu Asp Ser Ala Arg L ys Lys Val Leu Glu Phe
```

```
                195                 200                 205
Val Glu Ser Lys Met Gly Ser Ile Ala Pro Asn Leu Ser Ala Ile Val
    210                 215                 220

Gly Ser Ala Val Ala Ala Lys Leu Met Gly Thr Ala Gly Gly Leu Ser
225                 230                 235                 240

Ala Leu Ala Lys Met Pro Ala Cys Asn Val Gln Val Leu Gly His Lys
                245                 250                 255

Arg Lys Asn Leu Ala Gly Phe Ser Ser Ala Thr Ser Gln Ser Arg Val
            260                 265                 270

Gly Tyr Leu Glu Gln Thr Glu Ile Tyr Gln Ser Thr Pro Pro Gly Leu
        275                 280                 285

Gln Ala Arg Ala Gly Arg Leu Val Ala Ala Lys Ser Thr Leu Ala Ala
    290                 295                 300

Arg Val Asp Ala Thr Arg Gly Asp Pro Leu Gly Ile Ser Gly Lys Ala
305                 310                 315                 320

Phe Arg Glu Glu Ile Arg Lys Lys Ile Glu Lys Trp Gln Glu Pro Pro
                325                 330                 335

Pro Ala Arg Gln Pro Lys Pro Leu Pro Val Pro Asp Ser Glu Pro Lys
            340                 345                 350

Lys Arg Arg Gly Gly Arg Arg Leu Arg Lys Met Lys Glu Arg Tyr Gln
        355                 360                 365

Val Thr Asp Met Arg Lys Leu Ala Asn Arg Met Ala Phe Gly Thr Pro
    370                 375                 380

Glu Glu Ser Ser Leu Gly Asp Gly Leu Gly Glu Gly Tyr Gly Met Leu
385                 390                 395                 400

Gly Gln Ala Gly Ser Asn Arg Leu Arg Val Ser Ser Val Pro Ser Lys
                405                 410                 415

Leu Lys Ile Asn Ala Lys Val Ala Lys Lys Leu Lys Glu Arg Gln Tyr
            420                 425                 430

Ala Gly Gly Ala Thr Thr Ser Gly Leu Thr Ser Ser Leu Ala Phe Thr
        435                 440                 445

Pro Val Gln Gly Ile Glu Leu Cys Asn Pro Gln Gln Ala Leu Gly Leu
    450                 455                 460

Gly Ser Gly Thr Gln Ser Thr Tyr Phe Ser Glu Ser Gly Thr Phe Ser
465                 470                 475                 480

Lys Leu Lys Lys Ile
                485

<210> SEQ ID NO 5
<211> LENGTH: 1344
<212> TYPE: DNA
<213> ORGANISM: Arabidopsis thaliana
<220> FEATURE:
<221> NAME/KEY: CDS
<222> LOCATION: (1)..(1344)

<400> SEQUENCE: 5 atg gag aac ctt acc cta gtt tct tgc tca gct tct tct cca aag ctg     48
Met Glu Asn Leu Thr Leu Val Ser Cys Ser Ala Ser Ser Pro Lys Leu
  1               5                  10                  15 tta att gga tgc aat ttc act tcc tcg ctg aaa aac cct act ggg ttt     96
Leu Ile Gly Cys Asn Phe Thr Ser Ser Leu Lys Asn Pro Thr Gly Phe
                 20                  25                  30 tct cgt cgg act cct aat att gtc ctc cgg tgt tcc aaa ata tct gcc    144
Ser Arg Arg Thr Pro Asn Ile Val Leu Arg Cys Ser Lys Ile Ser Ala
             35                  40                  45
```

| | | |
|---|---|---|
| tct gct caa tct caa tct ccc tct tcg cgt c cg gag aac act gga gaa<br>Ser Ala Gln Ser Gln Ser Pro Ser Ser Arg P ro Glu Asn Thr Gly Glu<br>50              55                   60 | 192 |
| atc gtg gtt gtg aaa cag aga agc aaa gct t tt gca agt ata ttt tct<br>Ile Val Val Lys Gln Arg Ser Lys Ala P he Ala Ser Ile Phe Ser<br>65              70              75              80 | 240 |
| tcg agt cgt gat caa cag aca act tct gtt g ct tcc cct agt gtg cct<br>Ser Ser Arg Asp Gln Gln Thr Thr Ser Val A la Ser Pro Ser Val Pro<br>          85              90              95 | 288 |
| gtg cca cca cca tct tca tca acc ata gga t ca cca ctt ttc tgg att<br>Val Pro Pro Pro Ser Ser Ser Thr Ile Gly S er Pro Leu Phe Trp Ile<br>          100              105              110 | 336 |
| ggt gtt ggt gtt ggt cta tca gct ttg ttc t ca tat gta act tca aat<br>Gly Val Gly Val Gly Leu Ser Ala Leu Phe S er Tyr Val Thr Ser Asn<br>          115              120              125 | 384 |
| tta aag aaa tat gca atg caa aca gct atg a ag acg atg atg aac caa<br>Leu Lys Lys Tyr Ala Met Gln Thr Ala Met L ys Thr Met Met Asn Gln<br>130              135              140 | 432 |
| atg aat acg caa aat agc cag ttt aat aat t ct gga ttc cca tca gga<br>Met Asn Thr Gln Asn Ser Gln Phe Asn Asn S er Gly Phe Pro Ser Gly<br>145              150              155              160 | 480 |
| tca cct ttt ccg ttt cca ttt cct cct caa a ca agt cct gct tcc tcg<br>Ser Pro Phe Pro Phe Pro Phe Pro Pro Gln T hr Ser Pro Ala Ser Ser<br>          165              170              175 | 528 |
| cca ttc caa tct caa tcc cag tct tca ggt g ct acc gtt gat gtg aca<br>Pro Phe Gln Ser Gln Ser Gln Ser Ser Gly A la Thr Val Asp Val Thr<br>          180              185              190 | 576 |
| gcg aca aaa gta gag aca cct cct tca act a aa ccg aaa cct aca cct<br>Ala Thr Lys Val Glu Thr Pro Pro Ser Thr L ys Pro Lys Pro Thr Pro<br>          195              200              205 | 624 |
| gca aag gat ata gag gtg gat aag cca agt g tt gtc tta gag gca agc<br>Ala Lys Asp Ile Glu Val Asp Lys Pro Ser V al Val Leu Glu Ala Ser<br>210              215              220 | 672 |
| aaa gag aag aaa gaa gaa aag aac tat gcc t tt gaa gac att tca ccc<br>Lys Glu Lys Lys Glu Glu Lys Asn Tyr Ala P he Glu Asp Ile Ser Pro<br>225              230              235              240 | 720 |
| gag gaa acc aca aaa gaa agc cca ttt agc a ac tat gca gaa gtc tct<br>Glu Glu Thr Thr Lys Glu Ser Pro Phe Ser A sn Tyr Ala Glu Val Ser<br>          245              250              255 | 768 |
| gaa act aat tcc ccc aaa gaa act cgc ttg t tt gag gat gtc ttg caa<br>Glu Thr Asn Ser Pro Lys Glu Thr Arg Leu P he Glu Asp Val Leu Gln<br>          260              265              270 | 816 |
| aat gga gct ggt ccg gca aat ggt gcc act g ct tca gag gtt ttt caa<br>Asn Gly Ala Gly Pro Ala Asn Gly Ala Thr A la Ser Glu Val Phe Gln<br>          275              280              285 | 864 |
| tct ttg ggt ggt ggg aaa gga ggg ccg ggt t ta tct gta gaa gct tta<br>Ser Leu Gly Gly Gly Lys Gly Gly Pro Gly L eu Ser Val Glu Ala Leu<br>290              295              300 | 912 |
| gag aaa atg atg gaa gat cca aca gtc cag a ag atg gtt tac cca tac<br>Glu Lys Met Met Glu Asp Pro Thr Val Gln L ys Met Val Tyr Pro Tyr<br>305              310              315              320 | 960 |
| ttg cct gag gag atg agg aac cca gaa act t tc aaa tgg atg ctt aaa<br>Leu Pro Glu Glu Met Arg Asn Pro Glu Thr P he Lys Trp Met Leu Lys<br>          325              330              335 | 1008 |
| aat cct cag tac cgt caa caa cta cag gac a tg ttg aat aat atg agt<br>Asn Pro Gln Tyr Arg Gln Gln Leu Gln Asp M et Leu Asn Asn Met Ser<br>          340              345              350 | 1056 |
| ggg agt ggt gaa tgg gac aag cga atg aca g at aca ttg aag aat ttt<br>Gly Ser Gly Glu Trp Asp Lys Arg Met Thr A sp Thr Leu Lys Asn Phe<br>          355              360              365 | 1104 |

-continued

```
gac ctg aat agt cct gaa gtg aag caa caa t tc aat caa ata gga cta    1152
Asp Leu Asn Ser Pro Glu Val Lys Gln Gln P he Asn Gln Ile Gly Leu
        370             375                 380 act cca gaa gaa gtc ata tct aag atc atg g ag aac cct gat gtt gcc    1200
Thr Pro Glu Glu Val Ile Ser Lys Ile Met G lu Asn Pro Asp Val Ala
385             390                 395                 400 atg gca ttc cag aat cct aga gtc caa gca g cg tta atg gaa tgc tca    1248
Met Ala Phe Gln Asn Pro Arg Val Gln Ala A la Leu Met Glu Cys Ser
                405                 410                 415 gag aac cca atg aac atc atg aag tac caa a ac gac aaa gag gta atg    1296
Glu Asn Pro Met Asn Ile Met Lys Tyr Gln A sn Asp Lys Glu Val Met
            420                 425                 430 gat gtg ttc aac aag ata tcg cag ctc ttc c ca gga atg acg ggt tga    1344
Asp Val Phe Asn Lys Ile Ser Gln Leu Phe P ro Gly Met Thr Gly
        435                 440                 445
```

<210> SEQ ID NO 6
<211> LENGTH: 447
<212> TYPE: PRT
<213> ORGANISM: Arabidopsis thaliana

<400> SEQUENCE: 6

```
Met Glu Asn Leu Thr Leu Val Ser Cys Ser A la Ser Ser Pro Lys Leu
 1               5                  10                  15

Leu Ile Gly Cys Asn Phe Thr Ser Ser Leu L ys Asn Pro Thr Gly Phe
            20                  25                  30

Ser Arg Arg Thr Pro Asn Ile Val Leu Arg C ys Ser Lys Ile Ser Ala
        35                  40                  45

Ser Ala Gln Ser Gln Ser Pro Ser Ser Arg P ro Glu Asn Thr Gly Glu
    50                  55                  60

Ile Val Val Lys Gln Arg Ser Lys Ala P he Ala Ser Ile Phe Ser
65                  70                  75                  80

Ser Ser Arg Asp Gln Gln Thr Thr Ser Val A la Ser Pro Ser Val Pro
                85                  90                  95

Val Pro Pro Ser Ser Ser Thr Ile Gly S er Pro Leu Phe Trp Ile
            100                 105                 110

Gly Val Gly Val Gly Leu Ser Ala Leu Phe S er Tyr Val Thr Ser Asn
        115                 120                 125

Leu Lys Lys Tyr Ala Met Gln Thr Ala Met L ys Thr Met Met Asn Gln
    130                 135                 140

Met Asn Thr Gln Asn Ser Gln Phe Asn Asn S er Gly Phe Pro Ser Gly
145                 150                 155                 160

Ser Pro Phe Pro Phe Pro Phe Pro Pro Gln T hr Ser Pro Ala Ser Ser
                165                 170                 175

Pro Phe Gln Ser Gln Ser Gln Ser Ser Gly A la Thr Val Asp Val Thr
            180                 185                 190

Ala Thr Lys Val Glu Thr Pro Pro Ser Thr L ys Pro Lys Pro Thr Pro
        195                 200                 205

Ala Lys Asp Ile Glu Val Asp Lys Pro Ser V al Val Leu Glu Ala Ser
    210                 215                 220

Lys Glu Lys Lys Glu Glu Lys Asn Tyr Ala P he Glu Asp Ile Ser Pro
225                 230                 235                 240

Glu Glu Thr Thr Lys Glu Ser Pro Phe Ser A sn Tyr Ala Glu Val Ser
                245                 250                 255

Glu Thr Asn Ser Pro Lys Glu Thr Arg Leu P he Glu Asp Val Leu Gln
            260                 265                 270
```

```
Asn Gly Ala Gly Pro Ala Asn Gly Ala Thr Ala Ser Glu Val Phe Gln
            275                 280                 285

Ser Leu Gly Gly Gly Lys Gly Pro Gly Leu Ser Val Glu Ala Leu
        290                 295                 300

Glu Lys Met Met Glu Asp Pro Thr Val Gln Lys Met Val Tyr Pro Tyr
305                 310                 315                 320

Leu Pro Glu Glu Met Arg Asn Pro Glu Thr Phe Lys Trp Met Leu Lys
                325                 330                 335

Asn Pro Gln Tyr Arg Gln Gln Leu Gln Asp Met Leu Asn Asn Met Ser
            340                 345                 350

Gly Ser Gly Glu Trp Asp Lys Arg Met Thr Asp Thr Leu Lys Asn Phe
        355                 360                 365

Asp Leu Asn Ser Pro Glu Val Lys Gln Gln Phe Asn Gln Ile Gly Leu
370                 375                 380

Thr Pro Glu Glu Val Ile Ser Lys Ile Met Glu Asn Pro Asp Val Ala
385                 390                 395                 400

Met Ala Phe Gln Asn Pro Arg Val Gln Ala Ala Leu Met Glu Cys Ser
                405                 410                 415

Glu Asn Pro Met Asn Ile Met Lys Tyr Gln Asn Asp Lys Glu Val Met
            420                 425                 430

Asp Val Phe Asn Lys Ile Ser Gln Leu Phe Pro Gly Met Thr Gly
        435                 440                 445

<210> SEQ ID NO 7
<211> LENGTH: 2163
<212> TYPE: DNA
<213> ORGANISM: Arabidopsis thaliana
<220> FEATURE:
<221> NAME/KEY: CDS
<222> LOCATION: (1)..(2163)

<400> SEQUENCE: 7 atg tct agg gag gat ttt agt gat aca ctt cga gta ctt gtt gca act      48
Met Ser Arg Glu Asp Phe Ser Asp Thr Leu Arg Val Leu Val Ala Thr
 1               5                  10                  15 gat tgc cac ttg ggc tac atg gag aag gat gaa att agg cgg cat gat      96
Asp Cys His Leu Gly Tyr Met Glu Lys Asp Glu Ile Arg Arg His Asp
             20                  25                  30 tca ttt aag gct ttc gaa gag ata tgt tct ata gct gag gag aaa cag     144
Ser Phe Lys Ala Phe Glu Glu Ile Cys Ser Ile Ala Glu Glu Lys Gln
         35                  40                  45 gtg gac ttc tta ctc ctc gga ggt gat ctt ttt cat gag aat aaa ccc     192
Val Asp Phe Leu Leu Leu Gly Gly Asp Leu Phe His Glu Asn Lys Pro
     50                  55                  60 tct aga act acg tta gtt aaa gcc att gaa att ctt cgt cgc cac tgt     240
Ser Arg Thr Thr Leu Val Lys Ala Ile Glu Ile Leu Arg Arg His Cys
 65                  70                  75                  80 ctg aat gat aaa cca gtg cag ttt caa gta gtc agc gac cag aca gta     288
Leu Asn Asp Lys Pro Val Gln Phe Gln Val Val Ser Asp Gln Thr Val
                 85                  90                  95 aat ttt cag aat gcg ttt ggt caa gtc aat tac gag gat cca cac ttc     336
Asn Phe Gln Asn Ala Phe Gly Gln Val Asn Tyr Glu Asp Pro His Phe
            100                 105                 110 aat gta ggc ttg ccc gtg ttc agt att cat gga aac cat gat gat cca     384
Asn Val Gly Leu Pro Val Phe Ser Ile His Gly Asn His Asp Asp Pro
        115                 120                 125 gcc gga gtg gac aat ctt tct gca att gat att ctt tcc gca tgc aac     432
Ala Gly Val Asp Asn Leu Ser Ala Ile Asp Ile Leu Ser Ala Cys Asn
```

-continued

| | | | |
|---|---|---|---|
| ctt gtg aac tat ttt gga aag atg gtt ctt g gt ggt tct ggt gtt ggc<br>Leu Val Asn Tyr Phe Gly Lys Met Val Leu G ly Gly Ser Gly Val Gly<br>145                         150                         155                     160 | 480 |
| cag att act ctc tac cct ata ctt atg aag a ag ggc tca aca acc gtg<br>Gln Ile Thr Leu Tyr Pro Ile Leu Met Lys L ys Gly Ser Thr Thr Val<br>                     165                         170                     175 | 528 |
| gct ctc tat ggt tta gga aac atc agg gat g aa cgt ctc aat aga atg<br>Ala Leu Tyr Gly Leu Gly Asn Ile Arg Asp G lu Arg Leu Asn Arg Met<br>                  180                       185                      190 | 576 |
| ttt cag acc cca cat gct gtc caa tgg atg a gg cct gaa gtt caa gaa<br>Phe Gln Thr Pro His Ala Val Gln Trp Met A rg Pro Glu Val Gln Glu<br>              195                       200                     205 | 624 |
| gga tgt gat gtt tct gac tgg ttc aac att c tg gtg ctt cat caa aat<br>Gly Cys Asp Val Ser Asp Trp Phe Asn Ile L eu Val Leu His Gln Asn<br>210                         215                      220 | 672 |
| agg gtg aaa tca aac ccc aaa aat gca ata a gt gag cac ttt ctt cca<br>Arg Val Lys Ser Asn Pro Lys Asn Ala Ile S er Glu His Phe Leu Pro<br>225                        230                       235                     240 | 720 |
| cgt ttc ctc gac ttc att gtg tgg ggc cat g ag cat gaa tgc cta atc<br>Arg Phe Leu Asp Phe Ile Val Trp Gly His G lu His Glu Cys Leu Ile<br>                       245                       250                     255 | 768 |
| gac ccc cag gag gta tct gga atg ggc ttc c ac atc aca caa cca gga<br>Asp Pro Gln Glu Val Ser Gly Met Gly Phe H is Ile Thr Gln Pro Gly<br>                  260                       265                     270 | 816 |
| tct tct gtg gca aca tca ctt att gat ggg g aa tcg aag cca aaa cat<br>Ser Ser Val Ala Thr Ser Leu Ile Asp Gly G lu Ser Lys Pro Lys His<br>             275                       280                     285 | 864 |
| gtt ctt ctc tta gaa atc aag gga aat caa t at cgt cct acg aag ata<br>Val Leu Leu Leu Glu Ile Lys Gly Asn Gln T yr Arg Pro Thr Lys Ile<br>290                         295                       300 | 912 |
| cct ttg aca tct gtg agg cct ttt gag tat a ca gag att gtt tta aag<br>Pro Leu Thr Ser Val Arg Pro Phe Glu Tyr T hr Glu Ile Val Leu Lys<br>305                         310                       315                     320 | 960 |
| gat gaa agt gat att gat ccc aat gat caa a ac tca att ctg gaa cac<br>Asp Glu Ser Asp Ile Asp Pro Asn Asp Gln A sn Ser Ile Leu Glu His<br>                       325                       330                     335 | 1008 |
| ttg gat aaa gtg gtc aga aat cta ata gag a aa gct agc aaa aaa gct<br>Leu Asp Lys Val Val Arg Asn Leu Ile Glu L ys Ala Ser Lys Lys Ala<br>               340                       345                     350 | 1056 |
| gtt aac aga tca gag atc aaa ctc cca ttg g tt cga atc aag gta gat<br>Val Asn Arg Ser Glu Ile Lys Leu Pro Leu V al Arg Ile Lys Val Asp<br>             355                       360                     365 | 1104 |
| tat tct gga ttt atg acg ata aat cct caa a ga ttt gga cag aaa tat<br>Tyr Ser Gly Phe Met Thr Ile Asn Pro Gln A rg Phe Gly Gln Lys Tyr<br>370                         375                       380 | 1152 |
| gtg gga aag gtt gca aat ccc cag gac att t tg ata ttt tcc aag gct<br>Val Gly Lys Val Ala Asn Pro Gln Asp Ile L eu Ile Phe Ser Lys Ala<br>385                         390                       395                     400 | 1200 |
| tct aag aag ggt cgg agc gaa gcc aac atc g at gat tct gag cgg ctt<br>Ser Lys Lys Gly Arg Ser Glu Ala Asn Ile A sp Asp Ser Glu Arg Leu<br>                  405                       410                     415 | 1248 |
| cgt cca gaa gaa ctg aac cag cag aat ata g aa gct tta gta gct gaa<br>Arg Pro Glu Glu Leu Asn Gln Gln Asn Ile G lu Ala Leu Val Ala Glu<br>              420                       425                     430 | 1296 |
| agc aac ctg aaa atg gag atc ctt cca gtt a ac gat ctg gat gtt gct<br>Ser Asn Leu Lys Met Glu Ile Leu Pro Val A sn Asp Leu Asp Val Ala<br>             435                       440                     445 | 1344 |
| ctt cac aat ttt gtg aac aag gat gat aaa c ta gcc ttc tac tca tgc | 1392 |

```
                                                                  -continued Leu His Asn Phe Val Asn Lys Asp Asp Lys L eu Ala Phe Tyr Ser Cys
        450                 455                 460 gtt cag tac aat ctt caa gag act cgt ggt a aa ctt gca aag gat tca       1440
Val Gln Tyr Asn Leu Gln Glu Thr Arg Gly L ys Leu Ala Lys Asp Ser
465                 470                 475                 480 gat gcc aag aaa ttt gag gaa gat gac ttg a tt ctt aaa gtg gga gag       1488
Asp Ala Lys Lys Phe Glu Glu Asp Asp Leu I le Leu Lys Val Gly Glu
                    485                 490                 495 tgc tta gag gaa cgc ttg aaa gat agg tcc a ct cga ccc act ggt tcc       1536
Cys Leu Glu Glu Arg Leu Lys Asp Arg Ser T hr Arg Pro Thr Gly Ser
                500                 505                 510 tca cag ttt tta tcc act gga ttg act tca g ag aat ttg aca aaa gga       1584
Ser Gln Phe Leu Ser Thr Gly Leu Thr Ser G lu Asn Leu Thr Lys Gly
            515                 520                 525 agc agt ggc atc gcg aat gct tcg ttc agt g at gat gaa gac aca act       1632
Ser Ser Gly Ile Ala Asn Ala Ser Phe Ser A sp Asp Glu Asp Thr Thr
        530                 535                 540 cag atg tct ggt tta gct cct ccc act aga g ga cga aga ggt tca tcc       1680
Gln Met Ser Gly Leu Ala Pro Pro Thr Arg G ly Arg Arg Gly Ser Ser
545                 550                 555                 560 act gct aat aca act cgt ggt aga gct aaa g cc cca acc aga gga cga       1728
Thr Ala Asn Thr Thr Arg Gly Arg Ala Lys A la Pro Thr Arg Gly Arg
                565                 570                 575 ggc cgt ggt aag gcc tca agt gcg atg aag c aa acc act ctt gat agt       1776
Gly Arg Gly Lys Ala Ser Ser Ala Met Lys G ln Thr Thr Leu Asp Ser
                    580                 585                 590 tct ctt ggt ttc cgc cag tct caa aga tct g ct tcg gct gct gct tca       1824
Ser Leu Gly Phe Arg Gln Ser Gln Arg Ser A la Ser Ala Ala Ala Ser
                595                 600                 605 gct gcc ttc aaa agt gct tcc acc att gga g aa gat gat gta gat tct       1872
Ala Ala Phe Lys Ser Ala Ser Thr Ile Gly G lu Asp Asp Val Asp Ser
610                 615                 620 cct tca agc gaa gaa gtc gag cct gaa gat t tt aac aaa cct gac agc       1920
Pro Ser Ser Glu Glu Val Glu Pro Glu Asp P he Asn Lys Pro Asp Ser
625                 630                 635                 640 agt tcg gag gac gat gag agc act aaa ggc a aa gga cgt aaa aga cca       1968
Ser Ser Glu Asp Asp Glu Ser Thr Lys Gly L ys Gly Arg Lys Arg Pro
                645                 650                 655 gct act act aag aga ggc aga ggt aga ggt t ct ggg act tca aaa cgt       2016
Ala Thr Thr Lys Arg Gly Arg Gly Arg Gly S er Gly Thr Ser Lys Arg
                    660                 665                 670 ggt aga aaa aac gaa agc tct tct tca ctt a at agg cta ctc agt agc       2064
Gly Arg Lys Asn Glu Ser Ser Ser Ser Leu A sn Arg Leu Leu Ser Ser
                675                 680                 685 aaa gac gat gac gag gac gaa gat gat gaa g ac aga gaa aag aag ctt       2112
Lys Asp Asp Asp Glu Asp Glu Asp Asp Glu A sp Arg Glu Lys Lys Leu
690                 695                 700 aac aaa tct cag cct cgg gtt aca agg aac t at gga gct cta aga aga       2160
Asn Lys Ser Gln Pro Arg Val Thr Arg Asn T yr Gly Ala Leu Arg Arg
705                 710                 715                 720 taa                                                                    2163

<210> SEQ ID NO 8
<211> LENGTH: 720
<212> TYPE: PRT
<213> ORGANISM: Arabidopsis thaliana

<400> SEQUENCE: 8

Met Ser Arg Glu Asp Phe Ser Asp Thr Leu A rg Val Leu Val Ala Thr
1               5                   10                  15
```

-continued

```
Asp Cys His Leu Gly Tyr Met Glu Lys Asp Glu Ile Arg Arg His Asp
             20                  25                  30

Ser Phe Lys Ala Phe Glu Ile Cys Ser Ile Ala Glu Glu Lys Gln
         35                  40                  45

Val Asp Phe Leu Leu Gly Gly Asp Leu Phe His Glu Asn Lys Pro
         50                  55                  60

Ser Arg Thr Thr Leu Val Lys Ala Ile Glu Ile Leu Arg Arg His Cys
 65                  70                  75                  80

Leu Asn Asp Lys Pro Val Gln Phe Gln Val Ser Asp Gln Thr Val
             85                  90                  95

Asn Phe Gln Asn Ala Phe Gly Gln Val Asn Tyr Glu Asp Pro His Phe
             100                 105                 110

Asn Val Gly Leu Pro Val Phe Ser Ile His Gly Asn His Asp Asp Pro
         115                 120                 125

Ala Gly Val Asp Asn Leu Ser Ala Ile Asp Ile Leu Ser Ala Cys Asn
         130                 135                 140

Leu Val Asn Tyr Phe Gly Lys Met Val Leu Gly Gly Ser Gly Val Gly
145                 150                 155                 160

Gln Ile Thr Leu Tyr Pro Ile Leu Met Lys Lys Gly Ser Thr Thr Val
             165                 170                 175

Ala Leu Tyr Gly Leu Gly Asn Ile Arg Asp Glu Arg Leu Asn Arg Met
             180                 185                 190

Phe Gln Thr Pro His Ala Val Gln Trp Met Arg Pro Glu Val Gln Glu
             195                 200                 205

Gly Cys Asp Val Ser Asp Trp Phe Asn Ile Leu Val Leu His Gln Asn
         210                 215                 220

Arg Val Lys Ser Asn Pro Lys Asn Ala Ile Ser Glu His Phe Leu Pro
225                 230                 235                 240

Arg Phe Leu Asp Phe Ile Val Trp Gly His Glu His Glu Cys Leu Ile
                 245                 250                 255

Asp Pro Gln Glu Val Ser Gly Met Gly Phe His Ile Thr Gln Pro Gly
             260                 265                 270

Ser Ser Val Ala Thr Ser Leu Ile Asp Gly Glu Ser Lys Pro Lys His
         275                 280                 285

Val Leu Leu Leu Glu Ile Lys Gly Asn Gln Tyr Arg Pro Thr Lys Ile
         290                 295                 300

Pro Leu Thr Ser Val Arg Pro Phe Glu Tyr Thr Glu Ile Val Leu Lys
305                 310                 315                 320

Asp Glu Ser Asp Ile Asp Pro Asn Asp Gln Asn Ser Ile Leu Glu His
                 325                 330                 335

Leu Asp Lys Val Val Arg Asn Leu Ile Glu Lys Ala Ser Lys Lys Ala
             340                 345                 350

Val Asn Arg Ser Glu Ile Lys Leu Pro Leu Val Arg Ile Lys Val Asp
         355                 360                 365

Tyr Ser Gly Phe Met Thr Ile Asn Pro Gln Arg Phe Gly Gln Lys Tyr
         370                 375                 380

Val Gly Lys Val Ala Asn Pro Gln Asp Ile Leu Ile Phe Ser Lys Ala
385                 390                 395                 400

Ser Lys Lys Gly Arg Ser Glu Ala Asn Ile Asp Asp Ser Glu Arg Leu
             405                 410                 415

Arg Pro Glu Glu Leu Asn Gln Gln Asn Ile Glu Ala Leu Val Ala Glu
             420                 425                 430
```

-continued

```
Ser Asn Leu Lys Met Glu Ile Leu Pro Val Asn Asp Leu Asp Val Ala
            435                 440                 445

Leu His Asn Phe Val Asn Lys Asp Asp Lys Leu Ala Phe Tyr Ser Cys
        450                 455                 460

Val Gln Tyr Asn Leu Gln Glu Thr Arg Gly Lys Leu Ala Lys Asp Ser
465                 470                 475                 480

Asp Ala Lys Lys Phe Glu Glu Asp Leu Ile Leu Lys Val Gly Glu
                485                 490                 495

Cys Leu Glu Glu Arg Leu Lys Asp Arg Ser Thr Arg Pro Thr Gly Ser
                500                 505                 510

Ser Gln Phe Leu Ser Thr Gly Leu Thr Ser Glu Asn Leu Thr Lys Gly
            515                 520                 525

Ser Ser Gly Ile Ala Asn Ala Ser Phe Ser Asp Asp Glu Asp Thr Thr
        530                 535                 540

Gln Met Ser Gly Leu Ala Pro Pro Thr Arg Gly Arg Arg Gly Ser Ser
545                 550                 555                 560

Thr Ala Asn Thr Thr Arg Gly Arg Ala Lys Ala Pro Thr Arg Gly Arg
                565                 570                 575

Gly Arg Gly Lys Ala Ser Ser Ala Met Lys Gln Thr Thr Leu Asp Ser
                580                 585                 590

Ser Leu Gly Phe Arg Gln Ser Gln Arg Ser Ala Ser Ala Ala Ala Ser
            595                 600                 605

Ala Ala Phe Lys Ser Ala Ser Thr Ile Gly Glu Asp Asp Val Asp Ser
        610                 615                 620

Pro Ser Ser Glu Glu Val Glu Pro Glu Asp Phe Asn Lys Pro Asp Ser
625                 630                 635                 640

Ser Ser Glu Asp Asp Glu Ser Thr Lys Gly Lys Gly Arg Lys Arg Pro
                645                 650                 655

Ala Thr Thr Lys Arg Gly Arg Gly Arg Gly Ser Gly Thr Ser Lys Arg
                660                 665                 670

Gly Arg Lys Asn Glu Ser Ser Ser Leu Asn Arg Leu Leu Ser Ser
            675                 680                 685

Lys Asp Asp Asp Glu Asp Glu Asp Glu Asp Arg Glu Lys Lys Leu
        690                 695                 700

Asn Lys Ser Gln Pro Arg Val Thr Arg Asn Tyr Gly Ala Leu Arg Arg
705                 710                 715                 720

<210> SEQ ID NO 9
<211> LENGTH: 1434
<212> TYPE: DNA
<213> ORGANISM: Arabidopsis thaliana
<220> FEATURE:
<221> NAME/KEY: CDS
<222> LOCATION: (1)..(1434)

<400> SEQUENCE: 9 atg atg aca tta aac tca cta tct cca gct gaa tcc aaa gct att tct     48
Met Met Thr Leu Asn Ser Leu Ser Pro Ala Glu Ser Lys Ala Ile Ser
  1               5                  10                  15 ttc ttg gat acc tcc agg ttc aat cca atc cct aaa ctc tca ggt ggg     96
Phe Leu Asp Thr Ser Arg Phe Asn Pro Ile Pro Lys Leu Ser Gly Gly
             20                  25                  30 ttt agt ttg agg agg agg gat caa ggg aga ggt ttt gga aaa ggt gtt   144
Phe Ser Leu Arg Arg Arg Asp Gln Gly Arg Gly Phe Gly Lys Gly Val
         35                  40                  45 aag tgt tca gtg aaa gtg cag cag caa caa caa cct cct cca gca tgg   192
Lys Cys Ser Val Lys Val Gln Gln Gln Gln Gln Pro Pro Pro Ala Trp
```

```
                50                      55                      60
cct ggg aga gct gtt cct gag gcg cct cgt c aa tct tgg gat gga cca      240
Pro Gly Arg Ala Val Pro Glu Ala Pro Arg G ln Ser Trp Asp Gly Pro
 65                      70                      75                  80 aaa ccc atc tct atc gtt gga tct act ggt t cc atc ggc act cag aca      288
Lys Pro Ile Ser Ile Val Gly Ser Thr Gly S er Ile Gly Thr Gln Thr
                         85                      90                  95 ttg gat att gtg gct gag aat cct gac aaa t tt aga gtt gtg gct cta      336
Leu Asp Ile Val Ala Glu Asn Pro Asp Lys P he Arg Val Val Ala Leu
                100                     105                     110 gct gct ggt tcg aat gtt act cta ctt gct g at cag gta agg aga ttt      384
Ala Ala Gly Ser Asn Val Thr Leu Leu Ala A sp Gln Val Arg Arg Phe
            115                     120                     125 aag cct gcg ttg gtt gct gtt aga aac gag t ca ctg att aat gag ctt      432
Lys Pro Ala Leu Val Ala Val Arg Asn Glu S er Leu Ile Asn Glu Leu
        130                     135                     140 aaa gag gct tta gct gat ttg gac tat aaa c cc gag att att cca gga      480
Lys Glu Ala Leu Ala Asp Leu Asp Tyr Lys P ro Glu Ile Ile Pro Gly
145                     150                     155                 160 gag cta gga gtg att gag gtt gcc cga cat c ct gaa gct gta acc gtt      528
Glu Leu Gly Val Ile Glu Val Ala Arg His P ro Glu Ala Val Thr Val
                        165                     170                 175 gtt acc gga ata gta ggt tgt gcg gga ctg a ag cct acg gtt gct gca      576
Val Thr Gly Ile Val Gly Cys Ala Gly Leu L ys Pro Thr Val Ala Ala
                    180                     185                     190 att gaa gca gga aag gac att gct ctt gca a ac aaa gag aca tta atc      624
Ile Glu Ala Gly Lys Asp Ile Ala Leu Ala A sn Lys Glu Thr Leu Ile
                195                     200                     205 gca ggt ggt cct ttc gtg ctt ccg ctt gcc a ac aaa cat aat gta aag      672
Ala Gly Gly Pro Phe Val Leu Pro Leu Ala A sn Lys His Asn Val Lys
            210                     215                     220 att ctt ccg gca gat tca gaa cat tct gcc a ta ttt cag tgt att caa      720
Ile Leu Pro Ala Asp Ser Glu His Ser Ala I le Phe Gln Cys Ile Gln
225                     230                     235                 240 ggt ttg cct gaa ggc gct ctg cgc aag ata a tc ttg act gca tct ggt      768
Gly Leu Pro Glu Gly Ala Leu Arg Lys Ile I le Leu Thr Ala Ser Gly
                        245                     250                 255 gga gct ttt agg gat tgg cct gtc gaa aag c ta aag gaa gtt aaa gta      816
Gly Ala Phe Arg Asp Trp Pro Val Glu Lys L eu Lys Glu Val Lys Val
                    260                     265                     270 gcg gat gcg ttg aag cat cca aac tgg aac a tg gga aag aaa atc act      864
Ala Asp Ala Leu Lys His Pro Asn Trp Asn M et Gly Lys Lys Ile Thr
                275                     280                     285 gtg gac tct gct acg ctt ttc aac aag ggt c tt gag gtc att gaa gcg      912
Val Asp Ser Ala Thr Leu Phe Asn Lys Gly L eu Glu Val Ile Glu Ala
            290                     295                     300 cat tat ttg ttt gga gct gag tat gac gat a ta gag att gtc att cat      960
His Tyr Leu Phe Gly Ala Glu Tyr Asp Asp I le Glu Ile Val Ile His
305                     310                     315                 320 cct caa agt atc ata cat tcc atg att gaa a ca cag gat tca tct gtg     1008
Pro Gln Ser Ile Ile His Ser Met Ile Glu T hr Gln Asp Ser Ser Val
                        325                     330                 335 ctt gct caa ttg ggt tgg cct gat atg cgt t ta ccg att ctc tac acc     1056
Leu Ala Gln Leu Gly Trp Pro Asp Met Arg L eu Pro Ile Leu Tyr Thr
                    340                     345                     350 atg tca tgg ccc gat aga gtt cct tgt tct g aa gta act tgg cct aga     1104
Met Ser Trp Pro Asp Arg Val Pro Cys Ser G lu Val Thr Trp Pro Arg
                355                     360                     365 ctt gac ctt tgc aaa ctc ggt tca ttg act t tc aag aaa cca gac aat     1152
```

```
Leu Asp Leu Cys Lys Leu Gly Ser Leu Thr Phe Lys Lys Pro Asp Asn
        370                 375                 380 gtg aaa tac cca tcc atg gat ctt gct tat gct gct gga cga gct gga        1200
Val Lys Tyr Pro Ser Met Asp Leu Ala Tyr Ala Ala Gly Arg Ala Gly
385                 390                 395                 400 ggc aca atg act gga gtt ctc agc gcc gcc aat gag aaa gct gtt gaa        1248
Gly Thr Met Thr Gly Val Leu Ser Ala Ala Asn Glu Lys Ala Val Glu
                405                 410                 415 atg ttt att gat gaa aag ata agc tat ttg gat atc ttc aag gtt gtg        1296
Met Phe Ile Asp Glu Lys Ile Ser Tyr Leu Asp Ile Phe Lys Val Val
            420                 425                 430 gaa tta aca tgc gat aaa cat cga aac gag ttg gta aca tca ccg tct        1344
Glu Leu Thr Cys Asp Lys His Arg Asn Glu Leu Val Thr Ser Pro Ser
        435                 440                 445 ctt gaa gag att gtt cac tat gac ttg tgg gca cgt gaa tat gcc gcg        1392
Leu Glu Glu Ile Val His Tyr Asp Leu Trp Ala Arg Glu Tyr Ala Ala
450                 455                 460 gat gtg cag ctt tct tct ggt gct agg cca gtt cat gca tga              1434
Asp Val Gln Leu Ser Ser Gly Ala Arg Pro Val His Ala
465                 470                 475

<210> SEQ ID NO 10
<211> LENGTH: 477
<212> TYPE: PRT
<213> ORGANISM: Arabidopsis thaliana

<400> SEQUENCE: 10

Met Met Thr Leu Asn Ser Leu Ser Pro Ala Glu Ser Lys Ala Ile Ser
  1               5                  10                  15

Phe Leu Asp Thr Ser Arg Phe Asn Pro Ile Pro Lys Leu Ser Gly Gly
                20                  25                  30

Phe Ser Leu Arg Arg Arg Asp Gln Gly Arg Gly Phe Gly Lys Gly Val
            35                  40                  45

Lys Cys Ser Val Lys Val Gln Gln Gln Gln Pro Pro Pro Ala Trp
    50                  55                  60

Pro Gly Arg Ala Val Pro Glu Ala Pro Arg Gln Ser Trp Asp Gly Pro
 65                  70                  75                  80

Lys Pro Ile Ser Ile Val Gly Ser Thr Gly Ser Ile Gly Thr Gln Thr
                85                  90                  95

Leu Asp Ile Val Ala Glu Asn Pro Asp Lys Phe Arg Val Val Ala Leu
            100                 105                 110

Ala Ala Gly Ser Asn Val Thr Leu Leu Ala Asp Gln Val Arg Arg Phe
        115                 120                 125

Lys Pro Ala Leu Val Ala Arg Asn Glu Ser Leu Ile Asn Glu Leu
    130                 135                 140

Lys Glu Ala Leu Ala Asp Leu Asp Tyr Lys Pro Glu Ile Ile Pro Gly
145                 150                 155                 160

Glu Leu Gly Val Ile Glu Val Ala Arg His Pro Glu Ala Val Thr Val
                165                 170                 175

Val Thr Gly Ile Val Gly Cys Ala Gly Leu Lys Pro Thr Val Ala Ala
            180                 185                 190

Ile Glu Ala Gly Lys Asp Ile Ala Leu Ala Asn Lys Glu Thr Leu Ile
        195                 200                 205

Ala Gly Gly Pro Phe Val Leu Pro Leu Ala Asn Lys His Asn Val Lys
    210                 215                 220

Ile Leu Pro Ala Asp Ser Glu His Ser Ala Ile Phe Gln Cys Ile Gln
225                 230                 235                 240
```

```
Gly Leu Pro Glu Gly Ala Leu Arg Lys Ile Ile Leu Thr Ala Ser Gly
                245                 250                 255
Gly Ala Phe Arg Asp Trp Pro Val Glu Lys Leu Lys Glu Val Lys Val
            260                 265                 270
Ala Asp Ala Leu Lys His Pro Asn Trp Asn Met Gly Lys Lys Ile Thr
        275                 280                 285
Val Asp Ser Ala Thr Leu Phe Asn Lys Gly Leu Glu Val Ile Glu Ala
    290                 295                 300
His Tyr Leu Phe Gly Ala Glu Tyr Asp Ile Glu Ile Val Ile His
305                 310                 315                 320
Pro Gln Ser Ile Ile His Ser Met Ile Glu Thr Gln Asp Ser Ser Val
                325                 330                 335
Leu Ala Gln Leu Gly Trp Pro Asp Met Arg Leu Pro Ile Leu Tyr Thr
            340                 345                 350
Met Ser Trp Pro Asp Arg Val Pro Cys Ser Glu Val Thr Trp Pro Arg
        355                 360                 365
Leu Asp Leu Cys Lys Leu Gly Ser Leu Thr Phe Lys Lys Pro Asp Asn
    370                 375                 380
Val Lys Tyr Pro Ser Met Asp Leu Ala Tyr Ala Ala Gly Arg Ala Gly
385                 390                 395                 400
Gly Thr Met Thr Gly Val Leu Ser Ala Ala Asn Glu Lys Ala Val Glu
                405                 410                 415
Met Phe Ile Asp Glu Lys Ile Ser Tyr Leu Asp Ile Phe Lys Val Val
            420                 425                 430
Glu Leu Thr Cys Asp Lys His Arg Asn Glu Leu Val Thr Ser Pro Ser
        435                 440                 445
Leu Glu Glu Ile Val His Tyr Asp Leu Trp Ala Arg Glu Tyr Ala Ala
    450                 455                 460
Asp Val Gln Leu Ser Ser Gly Ala Arg Pro Val His Ala
465                 470                 475

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
gcggacatct acatttttga                                              20

<210> SEQ ID NO 12
<211> LENGTH: 1353
<212> TYPE: DNA
<213> ORGANISM: Arabidopsis thaliana

<400> SEQUENCE: 12
gctgggtaag tagatcgttg catcactatg agatgtctaa gcttcttagg gatcaatatg     60
acgctgaagg cgcttgtatg attatcaaat ctggatctcc aggcgcaaaa tctcaggtca    120
gtttcatcat tctcaaggca cttacagttt ccaactcttt gcttgtaact tagtttctgt    180
ttgttcttaa acatattttg aggatttgca gatatggaca gagcaagttg taagtatgta    240
tatcaaatgg gcagaaaggc taggccaaaa cgcgcgggtg gctgagaaat gtagtttatt    300
gagtaataaa agtggcgtaa gttcagccac gatagagttt gaattcgagt tgcttatgg    360
```

```
ttatctctta ggtgagcgag gtgtgcaccg ccttatcata agttccactt c taatgaggt      420 atacattata agttataact ctctttctcg taactaatca ctttcgtgtc c attatcatg      480 gcccgggaaa gaattaaaag aggttttctt tgcgccagga atgttcagcg a ctgttgata      540 tcataccact attcttgaga gcatcctg attttgaagt aaaggaaggt g atttgattg       600 tatcgtatcc tgcaaaagag gatcacaaaa tagctgagaa tatggtttgt a tccaccata      660 ttccgagtgg agtaacacta caatcttcag gtattcttga gtgtgttgtt a gttgttaca      720 ctttggttta ctgcatttta tgcagattat ataacatgag gtttttgatg c aggagaaag      780 aaaccggttt gcaaacagga tcaaagctct aaaccggttg aaggcgaagc t acttgtgat      840 agcaaaagag caaaaggttt cggatgtaaa taaaatcgac agcaagaaca t tttggaacc      900 gcgggaagaa accaggagtt atgtctctaa gggtcacaag atggtggttg a tagaaaaac      960 cggtttagag attctggacc tgaaatcggt cttggatgga aacattggac c actccttgg     1020 agctcatatt agcatgagaa gatcaattga tgcgatttag gcttaatcaa t tggtacttt     1080 aattgctttt tgttttgtat ccaaaaagca acaaatggtt gcttgtgtgt g tatatatat     1140 aaccttcttg tccagaacca tatatgattc taaccatcaa acaaagataa g aattggtga     1200 ctatgtgcta tactctacaa tatcaccatg aatacttcaa actagacttt t gataaattt     1260 tgaaacggtt attaccaata aaacgaaaac catgaaactc ttgttttaat t atcagattc     1320 gagaaagttg tgtacaaaca tagctgagaa ggg                                   1353
```

<210> SEQ ID NO 13
<211> LENGTH: 184
<212> TYPE: DNA
<213> ORGANISM: Arabidopsis thaliana

<400> SEQUENCE: 13

```
gcttaatcaa ttggtacttt aattgctttt tggtttgtat cccaaaagca a caaatggk t       60 gcttgtgtgt gtatatatat aaccttcttg gccagaacca tatatgawtc t aaccatta a     120 accaagatta gaattggtga ctaaaaaaaa agaaaaaaaa aaaaaaaaaa a aaaaaaaa a     180 aaaa                                                                    184
```

<210> SEQ ID NO 14
<211> LENGTH: 2170
<212> TYPE: DNA
<213> ORGANISM: Arabidopsis thaliana

<400> SEQUENCE: 14

```
atggtaagcg tttctttaac tctattttct tcattgtttc agttattggc g attgtattc       60 tctgtttatt gtaatcgtat tgtgttaatt ttgatttgac tcatcttctc t aaagttcaa     120 tttcaaaatt agggattccg agatcataga tattgctttg tttccgagat t tgagttatt     180 cttaagcttg ttttactaac tttcaatatg ttggatttgt tataggcaac t cttgaagat     240 tctttccttg ctgatttgga cgagttatct gacaatgaag cagaattggt g agtgttaaa     300 acacttttga ttactattat ctgtttactt ggaggagcta tgattgtaat t gtagtttgt     360 ttgattatac atatgcagga cgagaatgat ggtgatgttg aaaggaaga a gaagatgtt     420 gatatggata tggctgattt agagacactt aactatgatg atctcgataa t gtttctaag     480 ctgcagaaga gtcagagata tgctgatatt atgcataaag tagaggaggc t cttgggaaa     540 gattctgatg gagctgagaa aggaactgtc ttggaagatg atcctgagta t aagcttatt     600 gtggattgta atcagctttc ggtcgatatt gagaatgaaa tcgttattgt c cacaacttt     660
```

```
atcaaagaca agtacaagct taagtttcaa gagcttgagt cgttggttca t cacccctatt    720 gactatgcat gtgttgtgaa gaagattggg aatgagacgg atttggctct t gttgatctc    780 gctgaccttc ttccttcagc tattatcatg gttgtttcag ttactgcttt a actacgaaa    840 gggagtgcac tgccagagga tgttttgcaa aaggtgttag aggcttgtga t cgggcttta    900 gatcttgatt ccgcaaggaa gaaggtcctt gagtttgttg aaagtaagat g ggatctatt    960 gcacctaatc tttctgctat tgttgggagt gctgttgcag ccaaactcat g gggactgct   1020 ggaggtttgt cagcacttgc taaaatgcct gcgtgtaatg ttcaagttct t ggccacaag   1080 aggaagaacc ttgctgggtt ttcttctgca acgtctcagt cccgtgtggg t tatctggag   1140 cagacagaga tttaccaaag cacgcctcct ggacttcagg ctcgcgctgg c aggctcgtg   1200 gctgcaaaat caactttggc agcaagagtt gatgctacta gagggatcc g ttagggata   1260 agtggaaaag ctttcaggga ggagatccgt aagaagattg agaaatggca a gaacctcct   1320 cctgcaagac agcctaagcc acttcctgtt cctgattctg aaccgaagaa a agaagggt   1380 ggtcgccgtc taagaaaaat gaaagaaagg tagccttttt catcctactt t gtgtcctta   1440 attactgtag attgagttct attcacctgt atttattttg ttgcattctt a cgtttctct   1500 ttaaatcagg tatcaagtaa cagatatgag gaagctggcc aacagaatgg c gtttggtac   1560 acctgaagag agctccctcg gtaatatatc ttgtagttac acttgttaat g gccacttat   1620 aaggcactta gtctaatatc tactcttcat gatgataggt gatggactag g agaaggtta   1680 tggaatgctt ggccaggcag gaagcaacag gctgcgagta tccagtgttc c gagcaagct   1740 taagattaat gctaaggtcg ccaaaaagta agtgttcctc tatttctcct g tgtttttc    1800 ggattttatca tgttaatatt tttactctta caaattatcc tgccctgttc t tcttccatc   1860 atatctcatt tgcgtctttta tatcaattac ttttcaggc ttaaagaaag g cagtatgcg   1920 ggtggtgcga ctacctctgg tttgacatcg agcctggctt tcactcctgt g caggtacaa   1980 acatttcatt cgattcttga caaaagtttg atcctgtgtt ccatttgcat c actgtctga   2040 ctccaattgg ttatctatttt gacagggaat agagttgtgc aatcctcagc a ggctttagg   2100 attaggaagt gggactcaaa gcacttactt ctcagagtca ggaaccttct c gaagctgaa   2160 gaagatctaa                                                           2170
```

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: oligonucleotide

<400> SEQUENCE: 15

```
accttaggcg acttttgaac                                                   20
```

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: oligonucleotide

<400> SEQUENCE: 16

```
aaacgcttac catatctctt tcta                                              24
```

<210> SEQ ID NO 17
<211> LENGTH: 113
<212> TYPE: DNA
<213> ORGANISM: Arabidopsis thaliana

<400> SEQUENCE: 17

| aaacactagt cgctcgctgc tcttcaattt tcttctcgaa tctaatcgat t gatttctcc | 60 |
| ttcgattctt caggagaatc actgaagctt ttgcctccca agtagaaaga g at | 113 |

<210> SEQ ID NO 18
<211> LENGTH: 218
<212> TYPE: DNA
<213> ORGANISM: Arabidopsis thaliana
<220> FEATURE:
<221> NAME/KEY: misc_feature
<222> LOCATION: (1)..(218)
<223> OTHER INFORMATION: n = a, t, c or g

<400> SEQUENCE: 18

| aatatggaag acagagatnc aagtcttgaa aagccgagca ctaaaagtgt a aaaatgaac | 60 |
| caaaggtgga aagaaactgc tttctctatc tcatgtctgt tttaaggttt c ttcggtcac | 120 |
| ttaagagaca aaaggcattg ttttgatcac tctttggaaa cgttttataa a ttttatttt | 180 |
| tgtattagag ccaaaaaaaa aaaaaaaaaa aaaaaaaa | 218 |

<210> SEQ ID NO 19
<211> LENGTH: 4140
<212> TYPE: DNA
<213> ORGANISM: Arabidopsis thaliana

<400> SEQUENCE: 19

| cagtacactt agctacactg gatccaagtc tagtgctaaa ctcaaacctc g tggttttag | 60 |
| accaaaatct cttcttcttc gtttccttct tcctcatcat atctttcatc t tctccacca | 120 |
| gaatttgttt taggctctcc ttcttctgtt tcttttttctc ccaaagaaac a attagatat | 180 |
| ggagaacctt accctagttt cttgctcagc ttcttctccca aagctgttaa t tggatgcaa | 240 |
| tttcacttcc tcgctgaaaa accctactgg gttttctcgt cggactccta a tattgtcct | 300 |
| ccggtgttcc aaaatatctg cctctgctca atctcaatct ccctcttcgc g tccggagaa | 360 |
| cactggagaa atcggttagt ttgcaaattc cactcgacac tctattatag c aaatgccaa | 420 |
| aattttccgg aaaaatttcc agtttattac ttttatctat cttattgaaa c tcaaattgc | 480 |
| gaaccctttt cgactggttt aatatgagct tatgaattgc tatatctctt a aaaaaatcc | 540 |
| acactttgtg aatttgcaat ttgaattctt gtagaaacca ttcattgtta g aattgttta | 600 |
| ctttaagttt atgttcgatt tgcagtggtt gtgaaacaga gaagcaaagc t tttgcaagt | 660 |
| atattttctt cgagtcgtga tcaacagaca acttctgttg cttcccctag t gtgcctgtg | 720 |
| ccaccaccat cttcatcaac catgtaattt tcctggtttt ggacaatgtg c ttagtttgt | 780 |
| atgtcgtttg attcttggtt attaaattgt gttttttctt ttttcttgta g aggatcacc | 840 |
| actttctgg attggtgttg gtgttggtct atcagctttg ttctcatatg t gagtatcaa | 900 |
| gattccttcc taatttttttt ttcctctata aatattcttt cttgcttcaa t attgattaa | 960 |
| taagtgcttg acctttttttc ttttctgatg gcattgcagg taacttcaaa t ttaaaggta | 1020 |
| cagatacttg gccctctggt tttacgggac ttttgttctc tagtctgttg c agaaccacg | 1080 |
| atttttatgct tcatgtcaac tctagtgtat tgtgctcatg tatctgagat a gttttattc | 1140 |
| actaaactgg ttatcttaac aaggtgaact gtttgctcac acttgttgaa c cgtttatat | 1200 |

-continued

```
aagcatcgaa cttttgcctc tctttttttg ggtagtcact tgattcgtag a tggtaacct    1260
acataccatt atggttttag tgatgcaact caggtattca gacttatagt c attttcgca    1320
actccagtat ttgattgaaa tatattatac aagttgtcat tgctttctct c attattctc    1380
taaccggctg ttactctctt tggattttt ttttgctttt ggtttagaaa t atgcaatgc     1440
aaacagctat gaagacgatg atgaaccaaa tgaatacgca aaatagccag t ttaataatt   1500
ctggattccc atcaggatca cctttccgt ttccatttcc tcctcaaaca a gtcctgctt    1560
cctcgccatt ccaatctcaa tcccagtctt caggtgctac cgttgatgtg a cagcgacaa   1620
aagtagagac acctccttca actaaaccga aacctacacc tgcaaaggat a tagaggtgg   1680
ataagccaag tgttgtctta gaggcaagca aagagaagaa agaagaaaag a actatggta   1740
gattctttt ctgtttcaga aatcaacgtc ttttcatttg tattctcaat t ttgactttc    1800
ttcctttctc atttcccaag cttctaactt ggaagctgat ttacttttgg a tgcagcctt   1860
tgaagacatt tcacccgagg aaaccacaaa agaaagccca tttagcaact a tgcagaagt   1920
ctctgaaact aattccccca agaaactcg cttgtttgag gatgtaagtt t cgttttctt    1980
ttgtatttcc acagcacacc aagtggtgat ttaaaaacgt gacatagttt t gctaacctt   2040
ctatgctctc ttattgatct ctgggtgaag gtcttgcaaa atggagctgg t ccggcaaat   2100
ggtgccactg cttcagaggt ttttcaatct ttgggtgagt tattgaattt c agttttcat   2160
cactatcagc gcactgtgca tgattcatga ttaaggctac ggatttcaat t ttatttat    2220
agcatatgcc aacaattata aacaaggaa gatatgaaat tggtgataaa g aggaatgag    2280
ttggcttcaa aaggatctac tccgttactt ttgtccttct gctagtcgtt g atctgtatt   2340
ggtataacca tataagactt gcaggatatt accttggcaa tctgtttcat a tctcatgtg   2400
ttatgattct ttttcttat atgctcacgt tattgtctct cttttcctta t tctaaattt   2460
aaaactgaat cctgagtctg tctattgttt acacaggtgg tgggaagga g ggccgggtt   2520
tatctgtaga agctttagag aaaatgatgg aagatccaac agtccagaag a tggtttacc   2580
cgtaactcat cttccctagc acattgtctt taaatgcatc cattaagttt a tctttaaaa   2640
ctggttgctt agtggacatt tggtaacatt gcatgtataa atgcagatac t tgcctgagg   2700
agatgaggaa cccagaaact ttcaaatgta agtcttttaa tatttaatcc t gctatcatt   2760
cttttattag tcctcatttt tacatatttc taaagactaa aggttacatg a ctagcttt    2820
gaatgatgta attcgtttat aggttgatcc aatggttatc taaatttaaa a tacagtttg   2880
gtacttattg tctccgcttg gaattttgta gggatgctta aaaatcctca g taccgtcaa   2940
caactacagg acatgttgta agagctccat tttacgaaca atttagttgt t ccattgct    3000
tttaagaatg tctaaactat gtaattaaga aatactcttg tttgtttctt t tcatgaatt   3060
taggaataat atgagtggga gtggtgaatg ggacaagcga atgacagata c attgaagaa   3120
ttttgacctg aatagtcctg aagtgaagca acaattcagt aagacaaatc t cagtttgta   3180
ccaagttaat agtacgttaa ataggtctga tactcaatga ttgaatctgt a tttgtcaga   3240
tcaaatagga ctaactccag aagaagtcat atctaagatc atggagaacc c tgatgttgc   3300
catggcattc cagaatccta gagtccaagc agcgttaatg gaagtacgtt t tcttttaac   3360
ctgaataaga gaattgctta attttacccc acttctttct tcatacaaaa c agaaaccaa   3420
ttacattctt gttgttgttg cagtgctcag agaacccaat gaacatcatg a agtaccaaa   3480
acgacaaaga ggtaataata ctgccacttc tccattgccc aaaaaggcga t tactttttt   3540
```

-continued

| | |
|---|---|
| aagaaatttg aggttattat acattgattg caggtaatgg atgtgttcaa c aagatatcg | 3600 |
| cagctcttcc caggaatgac gggttgaaaa agctcacgtc tttggttcta t caaaaatgt | 3660 |
| cacattgtct ttagctttt gtagggagaa aaaaatgttt tttttttgc a aagagtctt | 3720 |
| cagttttggt cagatcagag aattgtgtac catgttaatc ttaaacgcgg t cgggaattg | 3780 |
| gagtcgtgtg aaaacgccgc tgctgttgtt tggtatgaat attatacaat a gaatttgtt | 3840 |
| gtcttaccaa aaaagtcta tgaagacact gaagagcaaa ttattatttt t aagggaaaa | 3900 |
| tttccaaaat aaacttcatg tattcaaaat ttgcttgaaa aaacctcaat t tttttgtt | 3960 |
| tgagattgtg tgaataaatc tgccaatatt ttgttttagc aatttaaaaa ttgaagtttt | 4020 |
| tttctcgca aatttaaat agttgtgatt tattttggaa ttttaccta t ttttaatat | 4080 |
| ccaaaaggag aagtgacgtg gcgatatcga agcggtttaa tgaagtgatg g ccccatctt | 4140 |

<210> SEQ ID NO 20
<211> LENGTH: 77
<212> TYPE: DNA
<213> ORGANISM: Arabidopsis thaliana

<400> SEQUENCE: 20

| | |
|---|---|
| ccacgcgtcc gctccaccag aatttgtttt aggctctcct tcttctgttt c tttttctcc | 60 |
| caaagaaaca attagat | 77 |

<210> SEQ ID NO 21
<211> LENGTH: 354
<212> TYPE: DNA
<213> ORGANISM: Arabidopsis thaliana

<400> SEQUENCE: 21

| | |
|---|---|
| aaaagctcac gtctttggtt ctatcaaaaa tgtcacattg tctttagctt t ttgtaggga | 60 |
| gaaaaaaatg tttttttttt tgcaaagagt cttcagtttt ggtcagatca g agaattgtg | 120 |
| taccatgtta atcttaaacg cggtcgggaa ttggagtcgt gtgaaaacgc c gctgctgtt | 180 |
| gtttggtatg aatattatac aatagaattt gttgtcttac caaaaaagt c tatgaagac | 240 |
| actgaagagc aaattattat ttttaaggga aaatttccaa aataaacttc a tgtattcaa | 300 |
| aatttgcttg aaaaacctc aatttttttt gttgaaaaaa aaaaaaaaa a aaa | 354 |

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: oligonucleotide

<400> SEQUENCE: 22

| | |
|---|---|
| cagaccacaa taccttcaaa aata | 24 |

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: oligonucleotide

<400> SEQUENCE: 23

| | |
|---|---|
| ccattgtgtc tccctcccgc tgtt | 24 |

<210> SEQ ID NO 24
<211> LENGTH: 5077
<212> TYPE: DNA
<213> ORGANISM: Arabidopsis thaliana

<400> SEQUENCE: 24

| | | | | | |
|---|---|---|---|---|---|
| atgattgtaa | aacttgacag | ggaggatttt | agtgatacac | ttcgagtact t | gttgcaact | 60 |
| gattgccact | tgggctacat | ggagaaggat | gaaattaggc | ggcatgattc a | tttaaggct | 120 |
| ttcgaagaga | tatgttctat | agctgaggag | aaacaggtct | ggtattcagt a | tctatccct | 180 |
| tgccagtatt | atcttgcgtt | tgaatcatct | aacatattat | cttaaataaa a | atcttctcc | 240 |
| caatattatg | agtagtaaac | agtgttctac | ctaatttta | caaaaattca a | ccaattgcg | 300 |
| aggaagaatt | ctcagaaagt | ttcatatctt | cttttttcac | tcttttgaaa c | aggtggact | 360 |
| tcttactcct | cggaggtgat | cttttttcatg | agaataaacc | ctctagaact a | cgttagtta | 420 |
| aagccattga | aattcttcgt | cgccactgtc | tgaatgataa | accagtgcag t | tcaagtag | 480 |
| tcagcgacca | gacagtaaat | tttcagaatg | cgtgagactc | tatcctttct g | ctattaatc | 540 |
| taatcataac | aggaaataat | ttcaactgaa | ctaattaatt | ggcaaattgg c | tcaaattcg | 600 |
| tgtatagatc | tacgtattct | tattaatccc | ttgacattat | tttctggcta c | aggtttggt | 660 |
| caagtcaatt | acgaggatcc | acacttcaat | gtaggcttgc | ccgtgttcag t | attcatgga | 720 |
| aaccatgatg | atccagccgg | agtggtacat | cacttacatc | tgcatgctct t | gttatgcaa | 780 |
| actcatttga | ataggtatat | agaactggat | tagttagtga | ataggtattt t | attgtgttt | 840 |
| ttgttctatg | tctcttatgg | ctacaggaca | atctttctgc | aattgatatt c | tttccgcat | 900 |
| gcaaccttgt | gaactatttt | ggaaagatgg | ttcttggtgg | ttctggtgtt g | gccagatta | 960 |
| ctctctaccc | tatacttatg | aagaaggttg | gtgtaaagaa | tttctaacct a | gacacctgg | 1020 |
| ctcccctga | cttcttggac | tatcatttaa | tcaaattaat | gtttagggct c | aacaaccgt | 1080 |
| ggctctctat | ggtttaggaa | acatcaggga | tgaacgtctc | aatagaatgt t | tcaggtaat | 1140 |
| ccagaggacc | ctcacctttt | gctatacaat | tgttaattgt | gttaatattt a | ttggtttca | 1200 |
| cagacccac | atgctgtcca | atggatgagg | cctgaagttc | aagaaggatg t | gatgtttct | 1260 |
| gactggttca | acattctggt | gcttcatcaa | aataggttga | ttccattgct a | taacatctt | 1320 |
| ttagatcgtt | ttcttactca | ttctgtatca | gaaaatttga | tactgtattc a | tatgacttg | 1380 |
| cagggtgaaa | tcaaacccca | aaaatgcaat | aagtgagcac | tttcttccac g | tttcctcga | 1440 |
| cttcattgtg | tggggccatg | agcatgaatg | cctaatcgac | ccccaggtcc a | tgaaaaatt | 1500 |
| tgattttttgg | agttattgca | tttaaataag | agtgagccac | aatgttactt g | cctctttga | 1560 |
| gctaaaagct | attaaacttt | tgaaggaggt | atctggaatg | ggcttccaca t | cacacaacc | 1620 |
| aggatcttct | gtggcaacat | cacttattga | tggggaatcg | aagccaaaac a | tgttcttct | 1680 |
| cttagaaatc | aaggttcttc | agcaaacaat | ctgaaatttc | atcttcactt t | attcgtact | 1740 |
| tcattttctg | gtcttttttc | ctccttttca | atcaagcatg | taagcttgag t | gacttaaaa | 1800 |
| tatatgactt | acagggaaat | caatatcgtc | ctacgaagat | acctttgaca t | ctgtgaggc | 1860 |
| cttttgagta | tacagaggta | aagtttactt | ttccttaata | tgttatggtg g | tggcagact | 1920 |
| tctttgctta | catattttca | aagtgcagat | tgttttaaag | gatgaaagtg a | tattgatcc | 1980 |
| caatgatcaa | aactcaattc | tggaacactt | ggataaagtg | gtacctattc c | ctcttctca | 2040 |
| tagttcatgt | ggatatcttt | tctcctgccc | ttttgaata | accagtcact g | aatgtctct | 2100 |
| actaatatct | acaaaattgt | taggtcagaa | atctaataga | gaaagctagc a | aaaagctg | 2160 |

-continued

```
ttaacagatc agagatcaaa ctcccattgg ttcgaatcaa ggtaacttgt t tccaagttt     2220 tcttcaaact gctgcaaatt ctagcaacac tcatataatt aaacctttat t ttctaaccc     2280 aactctagag gctaggcttt gccagtttga tgcatgcaca cccatagcca c aaacagata     2340 attgttatta agaatattaa atgactgaca aaagactaag atctgcttca t ctttcaggt     2400 agattattct ggatttatga cgataaatcc tcaaagattt ggacagaaat a tgtgggaaa     2460 ggtacctaga aattagttac tgtaacatga tggtcaccat acttctttga a tgttggcta     2520 actaatgaca aagtcccaaa cacttacagg ttgcaaatcc ccaggacatt t tgatatttt     2580 ccaaggcttc taagaagggt cggagcgaag gtaagggcat tggtgtacta g taatttata     2640 caattttgtt tggattagat tgatgcacgt gcttttactc taacttgtaa t agcttatct     2700 ggcaaaaatt acggttaagt agtgtatctg agatatagta atgtagaaca a tatgggcct     2760 atgataacct cctttgttgt tttattgtcg gtattataat tctcgtcata t atatcatga     2820 ctactaactt tctgttgtgt ggagcttgat attgatgtat tgagtgttaa t tttctttct     2880 gttccacttt tcttgttata gttcatgttt cttcgtgtgt aacctatagc a tcaaaattt     2940 tgcgaatctt atggattatc tctagttagt atatattgga aatttgccat t tgataatt      3000 tttttgtcta gtgaattgaa tggcaatgat gcatgtcctg atggttgtcc a gtgatccag     3060 ttatgatata tttcaatctt ccatttcaca gccaacatcg atgattctga g cggcttcgt     3120 ccagaagaac tgaaccagca gaatatagaa gctttagtag ctgaaagcaa c ctggtacat     3180 cctgcaacct tctttcctta tgattgtgtt attatcgtca acccctgtag a actttgcca     3240 cagaatgata tagacttggg tagttaccaa atgggcatga gtacactatg g gatgatcat     3300 tctattttct tccgcagaaa atggagatcc ttccagttaa cgatctggat g ttgctcttc     3360 acaattttgt gaacaaggat gataaactag ccttctactc atgcgttcag t acaatcttc     3420 aagagactcg tgtatgtact atttttttact tcaccattca atacaaagtt c tgcatagga     3480 tattatttt atttcgtagc acgtccttgt tattgctttt atgatttatc t cttccctct      3540 ttttgtacag ggtaaacttg caaaggattc agatgccaag aaatttgagg a agatgactt     3600 gattcttaaa gtgggagagt gcttagaggc aagaagatat agattcagtt a gttctgccg     3660 cagattatga gaaccagcag aatattgatc tcacttgcat tattgttcgt g caggaacgc     3720 ttgaaagata ggtccactcg acccactggt tcctcacagt ttttatccac t ggattgact     3780 tcagaggttt aaattctctt ttttagattt tccttgcctc tgtccttccg t tggtttctc     3840 acagtgctat tttctacctg agattggtac agaatttgac aaaaggaagc a gtggcatcg     3900 cgaatgcttc gttcagtgat gatgaagaca caactcagat gtctggttta g ctcctccca     3960 ctagaggacg aagaggttca tccactgcta atacaactcg tggtagagct a aagccccaa     4020 ccagaggacg aggccgtggt aaggcctcaa gtgcgatgaa gcaaaccact c ttgatagtt     4080 ctcttggttt ccgccagtct caaaggtaac tttttgacag cacatttaac c agtttaggg     4140 taggattcac ggacgtgcaa ggaaatgatt ggcatcacta gctagctaat g ttatgtccc     4200 taatttgtct ttcatagatc tgcttcggct gctgcttcag ctgccttcaa a gtgcttcc      4260 accattggag aagatgatgt agattctcct tcaagcgaag aagtcgagcc t gaagatttt     4320 aacaaacctg acagcagttc ggtatggact attccttaca ctgttattca t ttgttcact     4380 accataagaa agcccatgta aaacttgaca acatataac ttttggcatt c ttatttctc      4440 tatttgaagt aaattttgcg ttttttactt tcctgattct tgtttgatat c cactaaagg     4500 aggacgatga gagcactaaa ggcaaaggac gtaaaagacc agctactact a agagaggca     4560
```

```
gaggtagagg ttctgggact tcaaaacgtg gtagaaaaaa cgaaagctct t cttcactta      4620 ataggctact cagtagcaaa gacgatgacg aggacgaaga tgatgaagac a gagaaaaga     4680 agcttaacaa atctcagcct cgggtttgtt aatcacatct attttcccctt c tttcgctgc   4740 ttattagcag gttttagtaa gttgttgtta accatttgag atcaaagctc a cttaatagt    4800 acaatttgaa tatgcaggtt acaaggaact atggagctct aagaagataa a tacatatca   4860 aaccccaatc tctgacatca caacgaagct tcattttcct gttatttcct a gcgacctct   4920 caagcggaac aacttctgaa gaagagaaat tagtactaac aagagttctg t gagatgatg   4980 tacagagaat tttgtagtgt ttttttttct tgctcttttt aaggttacgt t gttgatgaa    5040 tgaggcaata tgattaacgt cagtaagaag tctaaaa                              5077
```

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: oligonucleotide

<400> SEQUENCE: 25

```
tgtaaaacga cggccagt                                                     18
```

<210> SEQ ID NO 26
<211> LENGTH: 255
<212> TYPE: DNA
<213> ORGANISM: Arabidopsis thaliana

<400> SEQUENCE: 26

```
atacatatca aaccccaatc tctgacatca caacgaagct tcattttcct g ttatttcct     60 agcgacctct caagcggaac aacttctgaa gaagagaaat tagtactaac a agagttctg   120 tgagatgatg tacagagaat tttgtagtgt ttttttttct tgctcttttt a aggttacgt   180 tgttgatgaa tgaggcaata tgattaacgt cagtaagaag tctaaaaaaa a aaaaaaaa   240 aaaaaaaaaa aaaaa                                                     255
```

<210> SEQ ID NO 27
<211> LENGTH: 2935
<212> TYPE: DNA
<213> ORGANISM: Arabidopsis thaliana

<400> SEQUENCE: 27

```
tcatgcatga actggcctag caccagaaga aagctgcaca ttcgcggcat a ttcacgtgc     60 ccacaagtca tagtgaacaa tctcttcaag agacggtgat gttaccaact c gtttcgatg   120 tttatcgcat gttaattcca caaccttgaa gatatccaaa tagcttatcc t gtaaacaaa   180 agtgagaata taacaattg tgattcgtat caagaacttc attgagatgc t caaaactga    240 aaataattc ttacttttca tcaatgaaca tttcaacagc tttctcattg g cggcgctga    300 gaactccagt cattgtgcct ccagctcgtc cagcagcata agcaagatcc a tggatgggt   360 atttcacatt gtctggtttc ttgaaagtca atgaaccgag tctgccaaaa t ccacaattg   420 taaacaactt tggttttag gtgctgaatg ctgatagata aggcagtggt c ctaacccag   480 tttaactgat ccacaccaaa acagtagcaa ataaccaat tgcaaaacca a accgaagac     540 cgattcggtt tcatttttta tcttatctaa acaacctaaa accaaactga a aacaagatt   600
```

-continued

```
ggggaactttt tcttggtgat aattaaaatt ttcaactaag cttagcttca c acttgataa    660 acagagagta tataaatgtg gttagcttac ttgcaaaggt caagtcttgg c caagttact    720 tcagaacaag gaactctatc gggccatgac atggtgtaga gaatcggtaa a cgcatatca    780 ggccaaccca attgagcaag cacagatgaa tcctgtggaa caaaacaaat a catgttata    840 cagttatttt tttaaaaccg gaaaataat aatttagtta gtaatgtttc a gcaagacct    900 gtgtttcaat catggaatgt atgatacttt gcggatgaat gacaatctct a tatcgtcat    960 actcagctcc aaacaaataa tgcgcttcaa tgacctcaag accctgtttc a aaaaatcaa   1020 gaactcatct accttgatca aaggtatttt caaaatcaga gtttaacctt a ggagaaaat   1080 aatcttaacc ttgttgaaaa gcgtagcaga gtccacagtg attttctttc c catgttcca   1140 gtttggatgc ttcaacgcat ccgctacttt aacttccttt agcttttcga c aggccaatc   1200 cctttttcaa aatccagtga aaagtttcca ttaaccaaac gagaattgag a agaaaaaaa   1260 gtctatgcag agagagaaga atatcgaaac aaacctaaaa gctccaccag a tgcagtcaa   1320 gattatcttg cgcagagcgc cttcaggcaa accttgaata cactagagaa c ataaaagaa   1380 gatttttcac tcaaattgcc agaggttgaa cttgcattaa gaccaacgct g aactcaata   1440 tgaaagttga ggtacttaat tctatgtgat ttgtgatacc tgaaatatgg c agaatgttc   1500 tgaatctgcc ggaagaatct ttacattatg tttgttggca gcggaagca c gaaaggacc   1560 acctgcgatt aatgtctctt tgtttgcaag agcaatgtcc tttcctgctt c aattgcagc   1620 aaccgtaggc tgcagtaaaa ataagcaaca agctttatca tctgcaactt t ctttttttca   1680 tatcctctta ataaggttta ataacaaaaa attagagtat atacctttag t cccgcacaa   1740 cctactattc cggtaacaac ggttacagct tcaggatgtc gggcaacctg t tgatgaaca   1800 taataagtaa aaacctatct acactacaat caaaactaac aaatgaacta a cctcaatca   1860 ctccttgctc tcctggaata atctcgagtt tatagtccaa atcagctaaa g cctctttaa   1920 gctcattaat cagtgactcg tttctaacag caaccaatgc aggcttaaat c tccttacct   1980 gccaccattc aaaatagaat cacagaacca tactatagag atttcttgag a ttgcagaag   2040 caaaagccta accagaacc tgatttctct ggtttgatct gatacataac g agttaatac   2100 tatcttgctt atgatactac cactgaactg agaattaaac tgaattccaa g tggtctgaa   2160 tgacaaattg gagagactca atactaattt ttttacaaat gaagccaact t acctgatca   2220 gcaagtagag taacattcga accagcagct agagccacaa ctctgaattt g tcaggattc   2280 tcagccacaa tatccaatgt ctgcaaaatg gaagttcttg tcgataaaaa t gatgcaaca   2340 ataactcagt aagaaaaaaa tatcattctt ctatgagtct agtcattcat a agacaaact   2400 taaagtctgg tcatactcaa gaactgcaca ataatgcctt aatcgaaata a aacctgagt   2460 gccaatagaa ccagtagatc caacgataga gatgggtttt ggtccatccc a agattgacg   2520 aggcgcctca gggacagctc tcccaggcca tgctggagga ggttgttgtt g ctgctgcac   2580 tttcactgaa cacttaacac cttttccaaa acctctccct tgattcctcc t cctcaaact   2640 aaacccacct gtgaaacact ccaaagatgt aaaatttaaa actctacgac c taaagcaaa   2700 ccaaaaaaaa tcgaattgaa gaaataacag attacctaga tagagaaatt c acaagagcc   2760 taagacaact aatgaaagtt tgcaacttta atcgaaaaga gagttgacca a ggaggagga   2820 aagaagagag gaagaagaag aaacctgaga gtttagggat tggattgaac c tggaggtat   2880 ccaagaaaga aatagctttg gattcagctg gagatagtga gtttaatgtc a tcat       2935
```

<210> SEQ ID NO 28
<211> LENGTH: 1434
<212> TYPE: DNA
<213> ORGANISM: Arabidopsis thaliana
<220> FEATURE:
<221> NAME/KEY: misc_feature
<222> LOCATION: (1)..(1434)
<223> OTHER INFORMATION: encodes SEQ ID NO:29

<400> SEQUENCE: 28

| | | | | | |
|---|---|---|---|---|---|
| atgatgacat | taaactcact | atctccagct | gaatccaaag | ctatttcttt c | ttggatacc | 60 |
| tccaggttca | atccaatccc | taaactctca | ggtgggttta | gtttgaggag g | aggratcaa | 120 |
| gggagaggtt | ttggaaaagg | tgttaagtgt | tcagtgaaag | tgcagcagca a | caacaacct | 180 |
| cctccagcat | ggcctgggag | agctgtycct | gaggcgcctc | gtcaatcttg g | gatggacca | 240 |
| aaacccatct | ctatcgttgg | atctactggt | tcyatyggca | ctcagacatt g | gatattgtg | 300 |
| gctgagaatc | ctgacaaatt | yagagttgtg | gctctagctg | ctggttcgaa t | gttactcta | 360 |
| cttgctgatc | aggtaaggag | atttaagcct | gcrttggttg | ctgttagaaa c | gagtcactg | 420 |
| attaatgagc | ttaaagaggc | tttagctgat | ttggactata | aacycgagat t | attccagga | 480 |
| gagcwaggag | tgattgaggt | tgcccgacat | cctgaagctg | taaccgttgt t | accggaata | 540 |
| gtaggttgtg | cgggactgma | gcctacggtt | gctgcaattg | aagcaggaaa g | gacattgct | 600 |
| cttgcaaaca | aagagacatt | aatcgcaggt | ggtcctttcg | tgcttccgct t | ccaacaaa | 660 |
| cataatgtaa | agattcttcc | ggcagattca | gaacattctg | ccatatttca g | tgtattcaa | 720 |
| ggtttgcctg | aaggcgctct | gcgcaagata | atcttgactg | catctggtgg a | gcttttagg | 780 |
| gattggcctg | tcgaaaagct | aaaggaagtt | aaagtagcgg | atgcgttgaa g | catccaaac | 840 |
| tggaacatgg | gaaagaaaat | cactgtggac | tctgctacgc | ttttcaacaa g | gtcttgag | 900 |
| gtcattgaag | cgcattattt | gtttggagct | gagtatgacg | atatagagat t | gtcattcat | 960 |
| cckcaaagta | tcatacattc | catgattgaa | acacaggatt | catctgtgct t | gctcaattg | 1020 |
| ggttggcctg | atatgcgttt | accgattctc | tacaccatgt | catggcccga t | agagttcct | 1080 |
| tgttctgaag | taacttggcc | wagacttgac | ctttgcaaac | tcggttcatt g | actttcaag | 1140 |
| aaaccagaca | atgtgaaata | cccatccatg | gatcttgctt | atgctgctgg a | cgagctgga | 1200 |
| ggcacaatga | ctggagttct | cagcgccgcc | aatgagaaag | ctgttgaaat g | ttyattgat | 1260 |
| gaaaagataa | gctatttgga | tatcttcaag | gttgtggaat | taacatgcga t | aaacatcga | 1320 |
| aacgagttgg | taacatcacc | gtctcttgaa | gagattgttc | actatgactt g | tgggcacgt | 1380 |
| gaatatgccg | cgratgtgca | gctttcttct | ggtgctaggc | cagttcatgc a | tga | 1434 |

<210> SEQ ID NO 29
<211> LENGTH: 477
<212> TYPE: PRT
<213> ORGANISM: Arabidopsis thaliana
<220> FEATURE:
<221> NAME/KEY: SITE
<222> LOCATION: (39)
<223> OTHER INFORMATION: Xaa = Asp or Asn
<221> NAME/KEY: SITE
<222> LOCATION: (155)
<223> OTHER INFORMATION: Xaa = Pro or Leu
<221> NAME/KEY: SITE
<222> LOCATION: (162)
<223> OTHER INFORMATION: Xaa = Leu or Gln
<221> NAME/KEY: SITE
<222> LOCATION: (187)
<223> OTHER INFORMATION: Xaa = Lys or Gln
<221> NAME/KEY: SITE
<222> LOCATION: (465)

<223> OTHER INFORMATION: Xaa = Asp or Asn

<400> SEQUENCE: 29

```
Met Met Thr Leu Asn Ser Leu Ser Pro Ala Glu Ser Lys Ala Ile Ser
  1               5                  10                  15

Phe Leu Asp Thr Ser Arg Phe Asn Pro Ile Pro Lys Leu Ser Gly Gly
             20                  25                  30

Phe Ser Leu Arg Arg Arg Xaa Gln Gly Arg Gly Phe Gly Lys Gly Val
         35                  40                  45

Lys Cys Ser Val Lys Val Gln Gln Gln Gln Pro Pro Pro Ala Trp
 50                  55                  60

Pro Gly Arg Ala Val Pro Glu Ala Pro Arg Gln Ser Trp Asp Gly Pro
 65                  70                  75                  80

Lys Pro Ile Ser Ile Val Gly Ser Thr Gly Ser Ile Gly Thr Gln Thr
                 85                  90                  95

Leu Asp Ile Val Ala Glu Asn Pro Asp Lys Phe Arg Val Val Ala Leu
                100                 105                 110

Ala Ala Gly Ser Asn Val Thr Leu Leu Ala Asp Gln Val Arg Arg Phe
            115                 120                 125

Lys Pro Ala Leu Val Ala Val Arg Asn Glu Ser Leu Ile Asn Glu Leu
130                 135                 140

Lys Glu Ala Leu Ala Asp Leu Asp Tyr Lys Xaa Glu Ile Ile Pro Gly
145                 150                 155                 160

Glu Xaa Gly Val Ile Glu Val Ala Arg His Pro Glu Ala Val Thr Val
                165                 170                 175

Val Thr Gly Ile Val Gly Cys Ala Gly Leu Xaa Pro Thr Val Ala Ala
            180                 185                 190

Ile Glu Ala Gly Lys Asp Ile Ala Leu Ala Asn Lys Glu Thr Leu Ile
            195                 200                 205

Ala Gly Gly Pro Phe Val Leu Pro Leu Ala Asn Lys His Asn Val Lys
            210                 215                 220

Ile Leu Pro Ala Asp Ser Glu His Ser Ala Ile Phe Gln Cys Ile Gln
225                 230                 235                 240

Gly Leu Pro Glu Gly Ala Leu Arg Lys Ile Ile Leu Thr Ala Ser Gly
                245                 250                 255

Gly Ala Phe Arg Asp Trp Pro Val Glu Lys Leu Lys Glu Val Lys Val
                260                 265                 270

Ala Asp Ala Leu Lys His Pro Asn Trp Asn Met Gly Lys Lys Ile Thr
            275                 280                 285

Val Asp Ser Ala Thr Leu Phe Asn Lys Gly Leu Glu Val Ile Glu Ala
            290                 295                 300

His Tyr Leu Phe Gly Ala Glu Tyr Asp Asp Ile Glu Ile Val Ile His
305                 310                 315                 320

Pro Gln Ser Ile Ile His Ser Met Ile Glu Thr Gln Asp Ser Ser Val
                325                 330                 335

Leu Ala Gln Leu Gly Trp Pro Asp Met Arg Leu Pro Ile Leu Tyr Thr
            340                 345                 350

Met Ser Trp Pro Asp Arg Val Pro Cys Ser Glu Val Thr Trp Pro Arg
            355                 360                 365

Leu Asp Leu Cys Lys Leu Gly Ser Leu Thr Phe Lys Lys Pro Asp Asn
            370                 375                 380

Val Lys Tyr Pro Ser Met Asp Leu Ala Tyr Ala Ala Gly Arg Ala Gly
385                 390                 395                 400
```

```
Gly Thr Met Thr Gly Val Leu Ser Ala Ala Asn Glu Lys Ala Val Glu
                405                 410                 415

Met Phe Ile Asp Glu Lys Ile Ser Tyr Leu Asp Ile Phe Lys Val Val
                420                 425                 430

Glu Leu Thr Cys Asp Lys His Arg Asn Glu Leu Val Thr Ser Pro Ser
            435                 440                 445

Leu Glu Glu Ile Val His Tyr Asp Leu Trp Ala Arg Glu Tyr Ala Ala
        450                 455                 460

Xaa Val Gln Leu Ser Ser Gly Ala Arg Pro Val His Ala
465                 470                 475
```

HERBICIDE TARGET GENES AND METHOD

This application claims the benefit of U.S. Provisional Application No. 60/240,917, filed Jan. 15, 1999. This application also claims the benefit of U.S. Provisional Application No. 60/183,017, filed Jan. 26, 1999. This application also claims the benefit of U.S. Provisional Application No. 60/198,245, filed Feb. 3, 1999. This application also claims the benefit of U.S. Provisional Application No. 60/304,202, filed Feb. 18, 1999. This application also claims the benefit of U.S. Provisional Application No. 60/155,231, filed Mar. 30, 1999. The disclosures of these priority documents are hereby expressly incorporated by reference in their entirety into the instant disclosure.

FIELD OF THE INVENTION

The invention relates to genes isolated from Arabidopsis that code for proteins essential for seedling growth. The invention also includes the methods of using these proteins as an herbicide target, based on the essentiality of the gene for normal growth and development. The invention is also useful as a screening assay to identify inhibitors that are potential herbicides. The invention may also be applied to the development of herbicide tolerant plants, plant tissues, plant seeds, and plant cells.

BACKGROUND OF THE INVENTION

The use of herbicides to control undesirable vegetation such as weeds in crop fields has become almost a universal practice. The herbicide market exceeds 15 billion dollars annually. Despite this extensive use, weed control remains a significant and costly problem for farmers.

Effective use of herbicides requires sound management. For instance, the time and method of application and stage of weed plant development are critical to getting good weed control with herbicides. Since various weed species are resistant to herbicides, the production of effective new herbicides becomes increasingly important. Novel herbicides can now be discovered using high-throughput screens that implement recombinant DNA technology. Metabolic enzymes found to be essential to plant growth and development can be recombinantly produced through standard molecular biological techniques and utilized as herbicide targets in screens for novel inhibitors of the enzyme activity. The novel inhibitors discovered through such screens may then be used as herbicides to control undesirable vegetation.

Herbicides that exhibit greater potency, broader weed spectrum, and more rapid degradation in soil can also, unfortunately, have greater crop phytotoxicity. One solution applied to this problem has been to develop crops that are resistant or tolerant to herbicides. Crop hybrids or varieties tolerant to the herbicides allow for the use of the herbicides to kill weeds without attendant risk of damage to the crop. Development of tolerance can allow application of a herbicide to a crop where its use was previously precluded or limited (e.g. to pre-emergence use) due to sensitivity of the crop to the herbicide. For example, U.S. Pat. No. 4,761,373 to Anderson et al. is directed to plants resistant to various imidazolinone or sulfonamide herbicides. An altered aceto-hydroxyacid synthase (AHAS) enzyme confers the resistance. U.S. Pat. No. 4,975,374 to Goodman et al. relates to plant cells and plants containing a gene encoding a mutant glutamine synthetase (GS) resistant to inhibition by herbicides that were known to inhibit GS, e.g. phosphinothricin and methionine sulfoximine. U.S. Pat. No. 5,013,659 to Bedbrook et al. is directed to plants expressing a mutant acetolactate synthase that renders the plants resistant to inhibition by sulfonylurea herbicides. U.S. Pat. No. 5,162,602 to Somers et al. discloses plants tolerant to inhibition by cyclohexanedione and aryloxyphenoxypropanoic acid herbicides. The tolerance is conferred by an altered acetyl coenzyme A carboxylase (ACCase).

Notwithstanding the above described advancements, there remain persistent and ongoing problems with unwanted or detrimental vegetation growth (e.g. weeds). Furthermore, as the population continues to grow, there will be increasing food shortages. Therefore, there exists a long felt, yet unfulfilled need, to find new, effective, and economic herbicides.

SUMMARY OF THE INVENTION

One object of the present invention is to provide an essential gene in plants for assay development for inhibitory compounds with herbicidal activity. Genetic results show that when the 245 gene, the 5283 gene, the 2490 gene, the 3963 gene or the 4036 gene is mutated in Arabidopsis, the resulting phenotype is seedling lethal in the homozygous state. This suggests a critical role for the gene product encoded by the mutated gene.

Using T-DNA insertion mutagenesis, the inventors of the present invention have demonstrated that the activity encoded by the Arabidopsis 245 gene, the Arabidopsis 5283 gene, the Arabidopsis 2490 gene, the Arabidopsis 3963 gene or the Arabidopsis 4036 gene (herein referred to as 245, 5283, 2490, 3963 or 4036 activity) is essential in Arabidopsis seedlings. This implies that chemicals that inhibit the function of the protein in plants are likely to have detrimental effects on plants and are potentially good herbicide candidates. The present invention therefore provides methods of using a purified protein encoded by the gene sequences described below to identify inhibitors thereof, which can then be used as herbicides to suppress the growth of undesirable vegetation, e.g. in fields where crops are grown, particularly agronomically important crops such as maize and other cereal crops such as wheat, oats, rye, sorghum, rice, barley, millet, turf and forage grasses, and the like, as well as cotton, sugar cane, sugar beet, oilseed rape, and soybeans.

The present invention discloses a nucleotide sequence derived from Arabidopsis, designated the 245 gene. The nucleotide sequence of the cDNA clone is set forth in SEQ ID NO:1, and the corresponding amino acid sequence is set forth in SEQ ID NO:2. The nucleotide sequence of the partial genomic DNA sequence is set forth in SEQ ID NO:12. The present invention also includes nucleotide sequences substantially similar to those set forth in SEQ ID NO:1. The present invention also encompasses plant proteins whose amino acid sequence are substantially similar to the amino acid sequences set forth in SEQ ID NO:2. Such proteins can be used in a screening assay to identify inhibitors that are potential herbicides.

The present invention further discloses a nucleotide sequence derived from Arabidopsis, designated the 5283 gene. The nucleotide sequence of the cDNA clone is set forth in SEQ ID NO:3, and the corresponding amino acid sequence is set forth in SEQ ID NO:4. The nucleotide sequence of the genomic DNA sequence is set forth in SEQ ID NO:14. The present invention also includes nucleotide sequences substantially similar to those set forth in SEQ ID NO:3. The present invention also encompasses plant proteins whose amino acid sequence are substantially similar to the amino acid sequences set forth in SEQ ID NO:4. Such proteins can be used in a screening assay to identify inhibitors that are potential herbicides.

The present invention further discloses a nucleotide sequence derived from Arabidopsis, designated the 2490 gene. The nucleotide sequence of the cDNA clone is set forth in SEQ ID NO:5, and the corresponding amino acid sequence is set forth in SEQ ID NO:6. The nucleotide sequence of the genomic DNA sequence is set forth in SEQ ID NO:19. The present invention also includes nucleotide sequences substantially similar to those set forth in SEQ ID NO:5. The present invention also encompasses plant proteins whose amino acid sequence are substantially similar to the amino acid sequences set forth in SEQ ID NO:6. Such proteins can be used in a screening assay to identify inhibitors that are potential herbicides.

The present invention further discloses a nucleotide sequence derived from Arabidopsis, designated the 3963 gene. The nucleotide sequence of the cDNA clone is set forth in SEQ ID NO:7, and the corresponding amino acid sequence is set forth in SEQ ID NO:8. The nucleotide sequence of the genomic DNA sequence is set forth in SEQ ID NO:24, which contains genomic DNA sequences from both the portion of the MDK4 clone annotated as MDK4.6 and added sequences on the 3' end based on the inventors' reported cDNA clone. The present invention also includes nucleotide sequences substantially similar to those set forth in in SEQ ID NO:7. The present invention also encompasses plant proteins whose amino acid sequence are substantially similar to the amino acid sequences set forth in SEQ ID NO:8. Such proteins can be used in a screening assay to identify inhibitors that are potential herbicides.

The present invention further discloses a nucleotide sequence derived from Arabidopsis, designated the 4036 gene. The nucleotide sequence of the cDNA clone is set forth in SEQ ID NO:9, and the corresponding amino acid sequence is set forth in SEQ ID NO:10. The nucleotide sequence of the genomic DNA sequence is set forth in SEQ ID NO:27. Thirteen nucleotide differences are observed by comparing the cDNA clone, derived from cv. Landsberg, and the genomic sequence, derived from cv. Columbia; and Table 1, below, further identifies these differences. SEQ ID NO:28 is the same as SEQ ID NO:9, but with these thirteen nucleotide differences. The corresponding amino acid sequence of SEQ ID NO:28 is set forth in SEQ ID NO:29. The present invention also includes nucleotide sequences substantially similar to those set forth in SEQ ID NO:9. The present invention also encompasses plant proteins whose amino acid sequence are substantially similar to the amino acid sequences set forth in SEQ ID NO:10 and SEQ ID NO:29. Such proteins can be used in a screening assay to identify inhibitors that are potential herbicides.

In a preferred embodiment, the present invention relates to a method for identifying chemicals having the ability to inhibit 245, 5283, 2490, 3963 or 4036 activity in plants preferably comprising the steps of: a) obtaining transgenic plants, plant tissue, plant seeds or plant cells, preferably stably transformed, comprising a non-native nucleotide sequence encoding an enzyme having 245, 5283, 2490, 3963 or 4036 activity and capable of overexpressing an enzymatically active 245, 5283, 2490, 3963 or 4036 gene product (either full length or truncated but still active); b) applying a chemical to the transgenic plants, plant cells, tissues or parts and to the isogenic non-transformed plants, plant cells, tissues or parts; c) determining the growth or viability of the transgenic and non-transformed plants, plant cells, tissues after application of the chemical; d) comparing the growth or viability of the transgenic and non-transformed plants, plant cells, tissues after application of the chemical; and e) selecting chemicals that suppress the viability or growth of the non-transgenic plants, plant cells, tissues or parts, without significantly suppressing the growth of the viability or growth of the isogenic transgenic plants, plant cells, tissues or parts. In a preferred embodiment, the enzyme having 245, 5283, 2490, 3963 or 4036 activity is encoded by a nucleotide sequence derived from a plant, preferably *Arabidopsis thaliana*, desirably identical or substantially similar to the nucleotide sequence set forth in SEQ ID NO:1, SEQ ID NO:3, SEQ ID NO:5, SEQ ID NO:7, or SEQ ID NO:9, respectively. In another embodiment, the enzyme having 245, 5283, 2490, 3963 or 4036 activity is encoded by a nucleotide sequence capable of encoding the amino acid sequence of SEQ ID NO:2, SEQ ID NO:4, SEQ ID NO:6, SEQ ID NO:8 or SEQ ID NO:10 respectively. In yet another embodiment, the enzyme having 245, 5283, 2490, 3963 or 4036 activity has an amino acid sequence identical or substantially similar to the amino acid sequence set forth in SEQ ID NO:2, SEQ ID NO:4, SEQ ID NO:6, SEQ ID NO:8 or SEQ ID NO:10 respectively.

The present invention further embodies plants, plant tissues, plant seeds, and plant cells that have modified 245, 5283, 2490, 3963 or 4036 activity and that are therefore tolerant to inhibition by a herbicide at levels normally inhibitory to naturally occurring 245, 5283, 2490, 3963 or 4036 activity. Herbicide tolerant plants encompassed by the invention include those that would otherwise be potential targets for normally inhibiting herbicides, particularly the agronomically important crops mentioned above. According to this embodiment, plants, plant tissue, plant seeds, or plant cells are transformed, preferably stably transformed, with a recombinant DNA molecule comprising a suitable promoter functional in plants operatively linked to a nucleotide coding sequence that encodes a modified 245, 5283, 2490, 3963 or 4036 gene that is tolerant to inhibition by a herbicide at a concentration that would normally inhibit the activity of wild-type, unmodified 245, 5283, 2490, 3963 or 4036 gene product. Modified 245, 5283, 2490, 3963 or 4036 activity may also be conferred upon a plant by increasing expression of wild-type herbicide-sensitive 245, 5283, 2490, 3963 or 4036 protein by providing multiple copies of wild-type 245, 5283, 2490, 3963 or 4036 genes to the plant or by overexpression of wild-type 245, 5283, 2490, 3963 or 4036 genes under control of a stronger-than-wild-type promoter. The transgenic plants, plant tissue, plant seeds, or plant cells thus created are then selected by conventional selection techniques, whereby herbicide tolerant lines are isolated, characterized, and developed. Alternately, random or site-specific mutagenesis may be used to generate herbicide tolerant lines.

Therefore, the present invention provides a plant, plant cell, plant seed, or plant tissue transformed with a DNA molecule comprising a nucleotide sequence isolated from a plant that encodes an enzyme having 245, 5283, 2490, 3963 or 4036 activity, wherein the DNA expresses the 245, 5283, 2490, 3963 or 4036 activity and wherein the DNA molecule confers upon the plant, plant cell, plant seed, or plant tissue tolerance to a herbicide in amounts that normally inhibits naturally occurring 245, 5283, 2490, 3963 or 4036 activity. According to one example of this embodiment, the enzyme having 245, 5283, 2490, 3963 or 4036 activity is encoded by a nucleotide sequence identical or substantially similar to the nucleotide sequence set forth in SEQ ID NO:1, SEQ ID NO:3, SEQ ID NO:5, SEQ ID NO:7, or SEQ ID NO:9, respectively, or has an amino acid sequence identical or substantially similar to the amino acid sequence set forth in SEQ ID NO:2, SEQ ID NO:4, SEQ ID NO:6, SEQ ID NO:8, or SEQ ID NO:10, respectively.

The invention also provides a method for suppressing the growth of a plant comprising the step of applying to the plant a chemical that inhibits the naturally occurring 245, 5283, 2490, 3963 or 4036 activity in the plant. In a related aspect, the present invention is directed to a method for selectively suppressing the growth of undesired vegetation in a field containing a crop of planted crop seeds or plants, comprising the steps of: (a) optionally planting herbicide tolerant crops or crop seeds, which are plants or plant seeds that are tolerant to a herbicide that inhibits the naturally occurring 245, 5283, 2490, 3963 or 4036 activity; and (b) applying to the herbicide tolerant crops or crop seeds and the undesired vegetation in the field a herbicide in amounts that inhibit naturally occurring 245, 5283, 2490, 3963 or 4036 activity, wherein the herbicide suppresses the growth of the weeds without significantly suppressing the growth of the crops.

Encompassed by the invention is an isolated DNA molecule comprising a nucleotide sequence substantially similar to any one of the sequences selected from the group consisting of SEQ ID NO:1, SEQ ID NO:3, SEQ ID NO:5, SEQ ID NO:7 and SEQ ID NO:9. Preferred is the DNA molecule according to the invention, wherein the sequence encodes an amino acid sequence substantially similar to any one of the sequences selected from the group consisting of SEQ ID NO:2, SEQ ID NO:4, SEQ ID NO:6, SEQ ID NO:8 and SEQ ID NO:10. Further preferred is DNA molecule according to the invention, wherein the sequence is any one of the sequences selected from the group consisting of SEQ ID NO:1, SEQ ID NO:3, SEQ ID NO:5, SEQ ID NO:7 and SEQ ID NO:9. Further preferred is the DNA molecule according to the invention, wherein the sequence encodes the amino acid sequence of any one of the sequences selected from the group consisting of SEQ ID NO:2, SEQ ID NO:4, SEQ ID NO:6, SEQ ID NO:8 and SEQ ID NO:10. Further preferred is a DNA molecule according to the invention, wherein said nucleotide sequence is a plant nucleotide sequence. More prefered is the DNA molecule according to the invention, wherein the plant is *Arabidopsis thaliana*. Further preferred is a DNA molecule according to the invention, wherein the protein has any one of the activities selected from the group consisting of 245 activity, 5283 activity, 2490 activity, 396 activity and 4036 activity. Further encompassed by the invention is an amino acid sequence comprising an amino acid sequence encoded by a nucleotide sequence substantially similar to any one of the sequences selected from the group consisting of SEQ ID NO:1, SEQ ID NO:3, SEQ ID NO:5, SEQ ID NO:7 and SEQ ID NO:9. Preferred is the amino acid sequence according to the invention comprising an amino acid sequence encoded by any one of the sequences selected from the group consisting of SEQ ID NO:1, SEQ ID NO:3, SEQ ID NO:5, SEQ ID NO:7 and SEQ ID NO:9. A further object of the invention is an amino acid sequence comprising an amino acid sequence substantially similar to any one of the sequences selected from the group consisting of SEQ ID NO:2, SEQ ID NO:4, SEQ ID NO:6, SEQ ID NO:8 and SEQ ID NO:10. Preferred is the amino acid sequence according to the invention, wherein the sequence is any one of the sequences selected from the group consisting of SEQ ID NO:2, SEQ ID NO:4, SEQ ID NO:6, SEQ ID NO:8 and SEQ ID NO:10. Further preferred is the amino acid sequence according to the invention, wherein the protein has any one of the activities selected from the group consisting of 245, 5283, 2490, 3963 and 4036 activity. Encompassed by the invention is an amino acid sequence comprising at least 20 consecutive amino acid residues of the amino acid sequence encoded by any one of the sequences selected from the group consisting of SEQ ID NO:1, SEQ ID NO:3, SEQ ID NO:5, SEQ ID NO:7 and SEQ ID NO:9. Further encompassed is an amino acid sequence comprising at least 20 consecutive amino acid residues of the amino acid sequence selected from the group consisting of SEQ ID NO:2, SEQ ID NO:4, SEQ ID NO:6, SEQ ID NO:8 and SEQ ID NO:10. An object of the invention is an expression cassette comprising a promoter operatively linked to a DNA molecule according to the invention. Further encompassed by the invention is a recombinant vector comprising an expression cassette according to the invention, wherein said vector is capable of being stably transformed into a host cell. Further encompassed is a host cell comprising an expression cassette according to the invention, wherein said nucleotide sequence is expressible in said cell. Preferred is a host cell according to the invention, wherein said host cell is an eukaryotic cell. More preferred is a host cell according to the invention, wherein said host cell is selected from the group consisting of an insect cell, a yeast cell, and a plant cell. Also more preferred is a host cell according to the invention, wherein said host cell is a prokaryotic cell. Also more preferred is a host cell according to the invention, wherein said host cell is a bacterial cell. Encompassed is a plant or seed comprising a plant cell according to the invention. Preferred is a plant according to the invention, wherein said plant is tolerant to an inhibitor of any one of the activities selected from the group consisting of 245 activity, 5283 activity, 2490 activity, 3963 activity and 4036 activity.

Further encompassed in the invention is a method comprising obtaining a host cell comprising a heterologous DNA molecule encoding a protein having 245, 5283, 2490, 3963, or 4036 activity; and expressing said protein in said host cell. Preferably the host cell is a bacterial cell, a yeast cell or an insect cell.

Further encompassed is a process for making nucleotides sequences encoding gene products having altered activity selected from the group consisting of 245 activity, 5283 activity, 2490 activity, 3963 activity and 4036 activity comprising, a) shuffling a nucleotide sequence of claim 1, b) expressing the resulting shuffled nucleotide sequences and c) selecting for altered activity selected from the group consisting of 245 activity, 5283 activity, 2490 activity, 3963 activity and 4036 activity as compared to the activity selected from the group consisting of 245 activity, 5283 activity, 2490 activity, 3963 activity and 4036 activity of the gene product of said unmodified nucleotide sequence.

Preferred is a process according to the invention, wherein the nucleotide sequence is any one of the sequences selected from the group consisting of SEQ ID NO:1, SEQ ID NO:3, SEQ ID NO:5, SEQ ID NO:7 and SEQ ID NO:9. Encompassed by the invention is a shuffled DNA molecule obtainable by the process according to the invention. Encompassed by the invention is a shuffled DNA molecule produced by the process according to the invention. Further encompassed by the invention is a shuffled DNA molecule obtained by the according to the invention, wherein said shuffled DNA molecule encodes a gene product having enhanced tolerance to an inhibitor of any one of the activities selected from the group consisting of 245 activity, 5283 activity, 2490 activity, 3963 activity and 4036 activity. A further object of the invention is an expression cassette comprising a promoter operatively linked to a nucleotide sequence according to the invention. Further encompassed by the invention is a recombinant vector comprising an expression cassette according to the invention, wherein said vector is capable of being stably transformed into a host cell. A further object of the invention is a host cell comprising an expression cassette according the invention, wherein said nucleotide sequence is expressible in said cell. Preferred is a host cell according to the invention, wherein said host cell is an eukaryotic cell. Also preferred is a host cell according to the invention, wherein said host cell is selected from the group consisting of an insect cell, a yeast cell, and a plant cell. Also preferred is a host cell according to the invention, wherein said host cell is a prokaryotic cell. Also preferred is a host cell according to the invention, wherein said host cell is a bacterial cell. An object of the invention is a plant or seed comprising a plant cell according to the invention. Preferred is a plant according to the invention, wherein said plant is tolerant to an inhibitor selected from the group consisting of 245, 5283, 2490, 3963 and 4036 activity. Further encompassed is a method for selecting compounds that interact with the protein encoded by any one of the sequences selected from the group consisting of SEQ ID NO:1, SEQ ID NO:3, SEQ ID NO:5, SEQ ID NO:7 and SEQ ID NO:9, comprising:

a) expressing a DNA molecule comprising any one of the sequences selected from the group consisting of SEQ ID NO:1, SEQ ID NO:3, SEQ ID NO:5, SEQ ID NO:7 and SEQ ID NO:9, respectively, or a sequence substantially similar to any one of the sequences selected from the group consisting of SEQ ID NO:1, SEQ ID NO:3, SEQ ID NO:5, SEQ ID NO:7 and SEQ ID NO:9 to generate the corresponding protein, b) testing a compound suspected of having the ability to interact with the protein expressed in step (a), and c) selecting compounds that interact with the protein in step (b).

A further object of the invention is a process of identifying an inhibitor of any one of the activities selected from the group consisting of 245 activity, 5283 activity, 2490 activity, 3963 activity and 4036 activity comprising:

a) introducing a DNA molecule comprising a nucleotide sequence of any one of the sequences selected from the group consisting of SEQ ID NO:1, SEQ ID NO:3, SEQ ID NO:5, SEQ ID NO:7 and SEQ ID NO:9, respectively, and having any one of the activities selected from the group consisting of 245 activity, 5283 activity, 2490 activity, 3963 activity and 4036 activity, or nucleotide sequences substantially similar thereto, or a homolog thereof, into a plant cell, such that said sequence is functionally expressible at levels that are higher than wild-type expression levels, b) combining said plant cell with a compound to be tested for the ability to inhibit any one of the activities selected from the group consisting of 245 activity, 5283 activity, 2490 activity, 3963 activity and 4036 activity under conditions conducive to such inhibition, c) measuring plant cell growth under the conditions of step (b), and d) comparing the growth of said plant cell with the growth of a plant cell having anunaltered activity selected from the group consisting of 245 activity, 5283 activity, 2490 activity, 3963 activity and 4036 activity under identical conditions, and e) selecting said compound that inhibits plant cell growth in step (d).

Encompassed by the invention is a compound having herbicidal activity identifiable according to the process according to the invention. Further encompassed is a process of identifying compounds having herbicidal activity comprising:

a) combining a protein according to the invention and a compound to be tested for the ability to interact with said protein, under conditions conducive to interaction, b) selecting a compound identified in step (a) that is capable of interacting with said protein, c) applying identified compound in step (b) to a plant to test for herbicidal activity, and d) selecting compounds having herbicidal activity.

Further encompassed is a compound having herbicidal activity identifiable according to the process according to the invention. A further object of the invention is a method for suppressing the growth of a plant comprising, applying to said plant a compound that inhibits the activity of the amino acid sequence according to the invention in an amount sufficient to suppress the growth of said plant. Preferred is the method according to the invention, wherein the compound is a compound having herbicidal activity identifiable according to the process according to the invention.

Encompassed is a method of improving crops comprising, applying to a herbicide tolerant plant or seed according to the invention, a compound having herbicidal activity identifiable according to a process according to the invention, in an amount that inhibits the growth of undesired vegetation without significantly suppressing the growth of the herbicide tolerant plant or seed. An object of the invention is a DNA molecule comprising a nucleotide sequence substantially similar to any one of the sequences selected from the group consisting of SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29.

It is an object of the invention to provide an effective and beneficial method to identify novel herbicides. A feature of the invention is the identification of a gene in Arabidopsis, herein referred to as the 245 gene, which shows sequence similarity to peptide release factor 2 (Craigen et al. (1985) Proc. Natl. Acad. Sci, 82: 3616–3620; Craigen and Caskey (1987) Biochimie 69: 1031–1041; Ito et al. (1998) Proc. Natl. Acad. Sci., 95: 8165–8169). Another feature of the invention is the discovery that the 245 gene is essential for seedling growth and development. An advantage of the present invention is that the newly discovered essential gene containing a novel herbicidal mode of action enables one skilled in the art to easily and rapidly identify novel herbicides.

A further feature of the invention is the identification of a gene in Arabidopsis, herein referred to as the 5283 gene, which shows sequence similarity to the following: an uncharacterized gene from *Schizosaccharomyces pombe*; the *Saccharomyces cerevisiae* PRP31 gene that encodes a factor essential for pre-mRNA splicing (Weidenhammer et al. (1996) Nucleic Acids Res. 24: 1164–1170; Weidenhammer et al. (1997) Mol. Cell. Biol., 17: 3580–3585); the *Pisum sativum* SARBP-1 and SARBP-2 genes that encode Scaffold Attachment Region (SAR) DNA-binding proteins (Rzepecki et al. (1995) Acta Biochim. Pol., 42: 75–81); and the *Saccharomyces cerevisiae* SIK1 gene that encodes a protein that can suppress the growth inhibitory effects of IKB (Morin et al. (1995) Cell Growth & Differentiation, 6: 789–798). The SIK1 gene product is also referred to as Nop56, which is shown to be an essential nucleolar protein (Gautier et al. (1997) Mol. Cell. Biol. 17: 7088–7098).

Another feature of the invention is the discovery that the 5283 gene is essential for seedling growth and development. An advantage of the present invention is that the newly discovered essential gene containing a novel herbicidal mode of action enables one skilled in the art to easily and rapidly identify novel herbicides.

A further feature of the invention is the identification of a gene in Arabidopsis, herein referred to as the 2490 gene, which encodes a protein with sequence similarity to a chloroplast envelope protein (Ko et al. (1995) The Journal of Biological Chem. 270: 28601–28608; Wu et al. (1994) The Journal of Biological Chem. 269: 32264–32271; Pang et al. (1997) The Journal of Biological Chem. 272: 25623–25627). Another feature of the invention is the discovery that the 2490 gene is essential for seedling growth and development. An advantage of the present invention is that the newly discovered essential gene containing a novel herbicidal mode of action enables one skilled in the art to easily and rapidly identify novel herbicides.

A further feature of the invention is the identification of a gene in Arabidopsis, herein referred to as the 3963 gene, which encodes a protein with sequence similarity to a number of DNA repair proteins, including Rad32 p from *Schizosaccharomyces pombe* (Genbank accession numberQ09683); hMre11 from *Homo sapiens* (Genbank accession number U37359); and Mre11p from *Saccharomyces cerevisiae* (Genbank accession number U60829) (Johzuka and Ogawa (1995) Genetics, 139: 1521–1532; Paull and Gellert (1998) Molecular Cell, 1: 969–979). Another feature of the invention is the discovery that the 3963 gene is essential for seedling growth and development. An advantage of the present invention is that the newly discovered essential gene containing a novel herbicidal mode of action enables one skilled in the art to easily and rapidly identify novel herbicides.

A further feature of the invention is the identification of a gene in Arabidopsis, herein referred to as the 4036 gene, which encodes a protein with sequence similarity to 1-deoxy-D-xylulose 5-phosphate reductoisomerase from a number of organisms including Synechocystis sp. (SWISS-PROTQ55663), *Bacillus subtilis* (SWISS-PROT 031753), and *Escherichia coli* (SWISS-PROT P45568) (Takahashi et al. (1998) Proc. Natl. Acad. Sci. USA, 95: 9879–9884). An important and unexpected feature of the invention is the discovery that the 4036 gene is essential for seedling growth and development. An advantage of the present invention is that the newly discovered essential gene containing a novel herbicidal mode of action enables one skilled in the art to easily and rapidly identify novel herbicides.

Other objects and advantages of the present invention will become apparent to those skilled in the art from a study of the following description of the invention and non-limiting examples.

DEFINITIONS

For clarity, certain terms used in the specification are defined and presented as follows:

Chimeric: is used to indicate that a DNA sequence, such as a vector or a gene, is comprised of more than one DNA sequences of distinct origin which are fused together by recombinant DNA techniques resulting in a DNA sequence, which does not occur naturally, and which particularly does not occur in the plant to be transformed.

Co-factor: natural reactant, such as an organic molecule or a metal ion, required in an enzyme-catalyzed reaction. A co-factor is e.g. AND(P), riboflavin (including FAD and FMN), folate, molybdopterin, thiamin, biotin, lipoic acid, pantothenic acid and coenzyme A, S-adenosylmethionine, pyridoxal phosphate, ubiquinone, menaquinone. Optionally, a co-factor can be regenerated and reused.

DNA shuffling: DNA shuffling is a method to rapidly, easily and efficiently introduce mutations or rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule. The shuffled DNA encodes an enzyme modified with respect to the enzyme encoded by the template DNA, and preferably has an altered biological activity with respect to the enzyme encoded by the template DNA.

Enzyme activity: means herein the ability of an enzyme to catalyze the conversion of a substrate into a product. A substrate for the enzyme comprises the natural substrate of the enzyme but also comprises analogues of the natural substrate, which can also be converted, by the enzyme into a product or into an analogue of a product. The activity of the enzyme is measured for example by determining the amount of product in the reaction after a certain period of time, or by determining the amount of substrate remaining in the reaction mixture after a certain period of time. The activity of the enzyme is also measured by determining the amount of an unused co-factor of the reaction remaining in the reaction mixture after a certain period of time or by determining the amount of used co-factor in the reaction mixture after a certain period of time. The activity of the enzyme is also measured by determining the amount of a donor of free energy or energy-rich molecule (e.g. ATP, phosphoenolpyruvate, acetyl phosphate or phosphocreatine) remaining in the reaction mixture after a certain period of time or by determining the amount of a used donor of free energy or energy-rich molecule (e.g. ADP, pyruvate, acetate or creatine) in the reaction mixture after a certain period of time.

Expression: refers to the transcription and/or translation of an endogenous gene or a transgene in plants. In the case of antisense constructs, for example, expression may refer to the transcription of the antisense DNA only.

Herbicide: a chemical substance used to kill or suppress the growth of plants, plant cells, plant seeds, or plant tissues.

Heterologous DNA Sequence: a DNA sequence not naturally associated with a host cell into which it is introduced, including non-naturally occurring multiple copies of a naturally occurring DNA sequence; and genetic constructs wherein an otherwise homologous DNA sequence is operatively linked to a non-native sequence.

Homologous DNA Sequence: a DNA sequence naturally associated with a host cell into which it is introduced.

Inhibitor: a chemical substance that causes abnormal growth, e.g., by inactivating the enzymatic activity of a protein such as a biosynthetic enzyme, receptor, signal transduction protein, structural gene product, or transport protein that is essential to the growth or survival of the plant. In the context of the instant invention, an inhibitor is a chemical substance that alters the enzymatic activity encoded by the 245 gene, the 5283 gene, the 2490 gene, the 3963 gene or the 4036 gene from a plant. More generally, an inhibitor causes abnormal growth of a host cell by interacting with the gene product encoded by the 245gene, the 5283 gene, the 2490 gene, the 3963 gene or the 4036 gene.

Isogenic: plants which are genetically identical, except that they may differ by the presence or absence of a heterologous DNA sequence.

Isolated: in the context of the present invention, an isolated DNA molecule or an isolated enzyme is a DNA molecule or enzyme that, by the hand of man, exists apart from its native environment and is therefore not a product of nature. An isolated DNA molecule or enzyme may exist in a purified form or may exist in a non-native environment such as, for example, in a transgenic host cell.

Marker gene: a gene encoding a selectable or screenable trait.

Mature protein: protein which is normally targeted to a cellular organelle, such as a chloroplast, and from which the transit peptide has been removed.

Minimal Promoter: promoter elements, particularly a TATA element, that are inactive or that have greatly reduced promoter activity in the absence of upstream activation. In the presence of a suitable transcription factor, the minimal promoter functions to permit transcription.

Modified Enzyme Activity: enzyme activity different from that which naturally occurs in a plant (i.e. enzyme activity that occurs naturally in the absence of direct or indirect manipulation of such activity by man), which is tolerant to inhibitors that inhibit the naturally occurring enzyme activity.

Plant: refers to any plant, particularly to seed plants.

Plant cell: structural and physiological unit of the plant, comprising a protoplast and a cell wall. The plant cell may be in form of an isolated single cell or a cultured cell, or as a part of higher organized unit such as, for example, a plant tissue, or a plant organ.

Plant material: refers to leaves, stems, roots, flowers or flower parts, fruits, pollen, pollen tubes, ovules, embryo sacs, egg cells, zygotes, embryos, seeds, cuttings, cell or tissue cultures, or any other part or product of a plant.

Pre-protein: protein which is normally targeted to a cellular organelle, such as a chloroplast, and still comprising its transit peptide.

Recombinant DNA molecule: a combination of DNA sequences that are joined together using recombinant DNA technology Selectable marker gene: a gene whose expression does not confer a selective advantage to a transformed cell, but whose expression makes the transformed cell phenotypically distinct from untransformed cells.

Significant Increase: an increase in enzymatic activity that is larger than the margin of error inherent in the measurement technique, preferably an increase by about 2-fold or greater of the activity of the wild-type enzyme in the presence of the inhibitor, more preferably an increase by about 5-fold or greater, and most preferably an increase by about 10-fold or greater.

Significantly less: means that the amount of a product of an enzymatic reaction is reduced by more than the margin of error inherent in the measurement technique, preferably a decrease by about 2-fold or greater of the activity of the wild-type enzyme in the absence of the inhibitor, more preferably an decrease by about 5-fold or greater, and most preferably an decrease by about 10-fold or greater.

In its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the substantially similar nucleotide sequence encodes the polypeptide encoded by the reference nucleotide sequence. The term "substantially similar" is specifically intended to include nucleotide sequences wherein the sequence has been modified to optimize expression in particular cells. The percentage of identity between the substantially similar nucleotide sequence and the reference nucleotide sequence desirably is at least 65%, more desirably at least 75%, preferably at least 85%, more preferably at least 90%, still more preferably at least 95%, yet still more preferably at least 99%. Sequence comparisons are carried out using a Smith-Waterman sequence alignment algorithm (see e.g. Waterman, M. S. Introduction to Computational Biology: Maps, sequences and genomes. Chapman & Hall. London: 1995. ISBN 0-412-99391-0,). The localS program, version 1.16, is used with following parameters: match: 1, mismatch penalty: 0.33, open-gap penalty: 2, extended-gap penalty: 2. A nucleotide sequence "substantially similar" to reference nucleotide sequence hybridizes to the reference nucleotide sequence in 7% sodium dodecyl sulfate (SDS), 0.5 M NaPO$_4$, 1 mM EDTA at 50° C. with washing in 2× SSC, 0.1% SDS at 50° C., more desirably in 7% sodium dodecyl sulfate (SDS), 0.5 M NaPO$_4$, 1 mM EDTA at 50° C. with washing in 1× SSC, 0.1% SDS at 50° C., more desirably still in 7% sodium dodecyl sulfate (SDS), 0.5 M NaPO$_4$, 1 mM EDTA at 50° C. with washing in 0.5× SSC, 0.1% SDS at 50° C., preferably in 7% sodium dodecyl sulfate (SDS), 0.5 M NaPO$_4$, 1 mM EDTA at 50° C. with washing in 0.1× SSC, 0.1% SDS at 50° C., more preferably in 7% sodium dodecyl sulfate (SDS), 0.5 M NaPO$_4$, 1 mM EDTA at 50° C. with washing in 0.1× SSC, 0.1% SDS at 65° C. As used herein the term "245 gene", "5283 gene", "2490 gene", "3963 gene" or "4036 gene" refers to a DNA molecule comprising SEQ ID NO:1, SEQ ID NO:3, SEQ ID NO:5, SEQ ID NO:7, or SEQ ID NO:9, respectively, or comprising a nucleotide sequence substantially similar to SEQ ID NO:1, SEQ ID NO:3, SEQ ID NO:5, SEQ ID NO:7 or SEQ ID NO:9, respectively. Homologs of the 245 gene, the 5283 gene, the 2490 gene, the 3963 gene or the 4036 gene include nucleotide sequences that encode an amino acid sequence that is at least 30% identical to SEQ ID NO:2, SEQ ID NO:4, SEQ ID NO:6, SEQ ID NO:8 or SEQ ID NO:10, respectively, as measured, using the parameters described below, wherein the amino acid sequence encoded by the homolog has the biological activity of the 245, 5283, 2490, 3963, or 4036 protein, respectively.

The term "substantially similar", when used herein with respect to a protein, means a protein corresponding to a reference protein, wherein the protein has substantially the same structure and function as the reference protein, e.g. where only changes in amino acids sequence not affecting the polypeptide function occur. When used for a protein or an amino acid sequence the percentage of identity between the substantially similar and the reference protein or amino acid sequence desirably is at least 65%, more desirably at least 75%, preferably at least 85%, more preferably at least 90%, still more preferably at least 95%, yet still more preferably at least 99%, using default BLAST analysis parameters. As used herein the term "245 protein", "5283 protein", "2490 protein", "3963 protein" or "4036 protein" refers to an amino acid sequence. encoded by a DNA molecule, comprising a nucleotide sequence substantially similar to SEQ ID NO:1, SEQ ID NO:3, SEQ ID NO:5, SEQ ID NO:7, or SEQ ID NO:9, respectively. Homologs of the 245 protein , the 5283 protein, the 2490 protein, the 3963 protein or the 4036 protein are amino acid sequences that are at least 30% identical to SEQ ID NO:2, SEQ ID NO:4, SEQ ID NO:6, SEQ ID NO:8 or SEQ ID NO:10, respectively, as measured using the parameters described below, wherein the homologs have the biological activity of the 245, 5283, 2490, 3963, or 4036 protein, respectively.

One skilled in the art is also familiar with other analysis tools, such as GAP analysis, to determine the percentage of identity between the "substantially similar" and the reference nucleotide sequence, or protein or amino acid sequence. In the present invention, "substantially similar" is therefore also determined using default GAP analysis parameters with the University of Wisconsin GCG, SEQWEB application of GAP, based on the algorithm of Needleman and Wunsch (Needleman and Wunsch (1970) J Mol. Biol. 48: 443–453).

Thus, in the context of the "245 gene" and using GAP analysis as described above, "substantially similar" refers to nucleotide sequences that encode a protein having at least 47% identity, more preferably at least 60% identity, still more preferably at least 75% identity, still more preferably at least 85% identity, still more preferably at least 95% identity, yet still more preferably at least 99% identity to SEQ ID NO:2.

In the context of the "5283 gene" and using GAP analysis as described above, "substantially similar" refers to nucleotide sequences that encode a protein having at least 74% identity, more preferably at least 80% identity, still more preferably at least 85% identity, still more preferably at least 90% identity, still more preferably at least 95% identity, yet still more preferably at least 99% identity to SEQ ID NO:4. Also, "substantially similar" preferably also refers to nucleotide sequences having at least 80% identity, more preferably at least 90% identity, still more preferably 95% identity, yet still more preferably at least 99% identity, to SEQ ID NO:3, wherein said nucleotide sequence comparisons are conducted using GAP analysis as described above.

In the context of the "2490 gene" and using GAP analysis as described above, "substantially similar" refers to nucleotide sequences that encode a protein having at least 82% identity, more preferably at least 85% identity, more preferably at least 90% identity, still more preferably at least 95% identity, yet still more preferably at least 99% identity to SEQ ID NO:6. Also, "substantially similar" preferably also refers to nucleotide sequences having at least 87% identity, more preferably at least 90% identity, still more preferably 95% identity, yet still more preferably at least 99% identity, to SEQ ID NO:5, wherein said nucleotide sequence comparisons are conducted using GAP analysis as described above.

In the context of the "3963 gene" and using GAP analysis as described above, "substantially similar" refers to nucleotide sequences that encode a protein having at least 40% identity, more preferably at least 60% identity, more preferably at least 80% identity, still more preferably at least 90% identity, still more preferably at least 95% identity, yet still more preferably at least 99% identity to SEQ ID NO:8. Also, "substantially similar" preferably also refers to nucleotide sequences having at least 49% identity, more preferably at least 60% identity, still more preferably 80% identity, more preferably at least 90% identity, more preferably at least 95% identity, yet still more preferably at least 99% identity, to SEQ ID NO:7, wherein said nucleotide sequence comparisons are conducted using GAP analysis as described above.

In the context of the "4036 gene" and using GAP analysis as described above, "substantially similar" refers to nucleotide sequences that encode a protein having at least 67% identity, more preferably at least 80% identity, more preferably at least 85% identity, still more preferably at least 90% identity, still more preferably at least 95% identity, yet still more preferably at least 99% identity to SEQ ID NO:10.

Further, using GAP analysis as described above, "homologs of the 245 gene" include nucleotide sequences that encode an amino acid sequence that has at least 24% identity to SEQ ID NO:2, more preferably at least 30% identity, still more preferably at least 40% identity, still more preferably at least 45% identity, yet still more preferably at least 55% identity, still more preferably at least 65% identity, yet still more preferably at least 75% identity to SEQ ID NO:2, wherein the amino acid sequence encoded by the homolog has the biological activity of the 245 protein.

Further, using GAP analysis as described above, "homologs of the 5283 gene" include nucleotide sequences that encode an amino acid sequence that has at least 23% identity to SEQ ID NO:4, more preferably at least 40% identity, still more preferably at least 50% identity, still more preferably at least 60% identity, yet still more preferably at least 74% identity to SEQ ID NO:4, wherein the amino acid sequence encoded by the homolog has the biological activity of the 5283 protein.

Further, using GAP analysis as described above, "homologs of the 2490 gene" include nucleotide sequences that encode an amino acid sequence that has at least 30% identity to SEQ ID NO:6, more preferably at least 30% identity, still more preferably at least 50% identity, still more preferably at least 60% identity, yet still more preferably at least 80% identity to SEQ ID NO:6, wherein the amino acid sequence encoded by the homolog has the biological activity of the 2490 protein.

Further, using GAP analysis as described above, "homologs of the 3963 gene" include nucleotide sequences that encode an amino acid sequence that has at least 34% identity to SEQ ID NO:8, more preferably at least 40% identity, still more preferably at least 50% identity, still more preferably at least 60% identity, yet still more preferably at: least 75% identity to SEQ ID NO:8, wherein the amino acid sequence encoded by the homolog has the biological activity of the 3963 protein.

Further, using GAP analysis as described above, "homologs of the 4036 gene" include nucleotide sequences that encode an amino acid sequence that has at least 44% identity to SEQ ID NO:10, more preferably at least 50% identity, still more preferably at least 60% identity, yet still more preferably at least 75% identity to SEQ ID NO:I0, wherein the amino acid sequence encoded by the homolog has the biological activity of the 4036 protein.

When using GAP analysis as described above with respect to a protein or an amino acid sequence and in the context of the "245 gene", the percentage of identity between the "substantially similar" protein or amino acid sequence and the reference protein or amino acid sequence (in this case SEQ ID NO:2) is at least 47%, more preferably at least 60%, still more preferably at least 75%, still more preferably at least 85%, still more preferably at least 95%, yet still more preferably at least 99%. "Homologs of the 245 protein" include amino acid sequences that are at least 24% identical to SEQ ID NO:2, more preferably at least 30% identical, still more preferably at least 40% identical, still more preferably at least 45% identical, yet still more preferably at least 55% identical, still more preferably at least 65% identical, yet still more preferably at least 75% identical to SEQ ID NO:2, wherein homologs of the 245 protein have the biological activity of the 245 protein.

In the context of the "5283 gene" and using GAP analysis as described above, the percentage of identity between the substantially similar protein or amino acid sequence and the reference protein or amino acid sequence (in this case SEQ ID NO:4) is at least 74%, more preferably at least 80%, still more preferably at least 85%, still more preferably at least 90%, still more preferably at least 95%, yet still more preferably at least 99%. "Homologs of the 5283 protein" include amino acid sequences that at least 23% identity to SEQ ID NO:4, more preferably at least 40% identity, still more preferably at least 50% identity, still more preferably at least 60% identity, yet still more preferably at least 74% identity to SEQ ID NO:4, wherein homologs of the 5283 protein have the biological activity of the 5283 protein.

In the context of the "2490 gene" and using GAP analysis as described above, the percentage of identity between the substantially similar protein or amino acid sequence and the reference protein or amino acid sequence (in this case SEQ ID NO:6) is at least 82%, more preferably at least 85%, more preferably at least 90%, still more preferably at least 95%, yet still more preferably at least 99%. "Homologs of the 2490 protein" include amino acid sequences that have at least 30% identity to SEQ ID NO:6, more preferably at least 30% identity, still more preferably at least 50% identity, still more preferably at least 60% identity, yet still more preferably at least 80% identity to SEQ ID NO:6, wherein the homologs of the 2490 protein have the biological activity of the 2490 protein.

In the context of the "3963 gene" and using GAP analysis as described above, the percentage of identity between the substantially similar protein or amino acid sequence and the reference protein or amino acid sequence (in this case SEQ ID NO:8) is at least 40%, more preferably at least 60%, more preferably at least 80%, still more preferably at least 90%, still more preferably at least 95%, yet still more preferably at least 99%. "Homologs of the 3963 protein" include amino acid sequences that has at least 34% identity to SEQ ID NO:8, more preferably at least 40% identity, still more preferably at least 50% identity, still more preferably at least 60% identity, yet still more preferably at least 75% identity to SEQ ID NO:8, wherein the homologs of the 3963 protein have the biological activity of the 3963 protein.

In the context of the "4036 gene" and using GAP analysis as described above, the percentage of identity between the substantially similar reference protein or amino acid sequence and the reference protein or amino acid sequence (in this case SEQ ID NO:10) is at least 67%, more preferably at least 80%, more preferably at least 85%, still more preferably at least 90%, still more preferably at least 95%, yet still more preferably at least 99%. "Homologs of the 4036 protein" include amino acid sequences that have at least 44% identity to SEQ ID NO:10, more preferably at least 50% identity, still more preferably at least 60% identity, yet still more preferably at least 75% identity to SEQ ID NO:10, wherein the homologs of the 4036 protein has the biological activity of the 4036 protein.

Substrate: a substrate is the molecule that an enzyme naturally recognizes and converts to a product in the biochemical pathway in which the enzyme naturally carries out its function, or is a modified version of the molecule, which is also recognized by the enzyme and is converted by the enzyme to a product in an enzymatic reaction similar to the naturally-occurring reaction.

Tolerance: the ability to continue essentially normal growth or function when exposed to an inhibitor or herbicide in an amount sufficient to suppress the normal growth or function of native, unmodified plants.

Transformation: a process for introducing heterologous DNA into a cell, tissue, or plant. Transformed cells, tissues, or plants are understood to encompass not only the end product of a transformation process, but also transgenic progeny thereof.

Transgenic: stably transformed with a recombinant DNA molecule that preferably comprises a suitable promoter operatively linked to a DNA sequence of interest.

BRIEF DESCRIPTION OF THE SEQUENCES IN THE SEQUENCE LISTING

SEQ ID NO:1 cDNA sequence for the Arabidopsis 245 gene
SEQ ID NO:2 amino acid sequence encoded by the Arabidopsis 245 DNA sequence shown in SEQ ID NO:1
SEQ ID NO:3 cDNA sequence for the Arabidopsis 5283 gene
SEQ ID NO:4 amino acid sequence encoded by the Arabidopsis 5283 DNA sequence shown in SEQ ID NO:3
SEQ ID NO:5 cDNA sequence for the Arabidopsis 2490 gene
SEQ ID NO:6 amino acid sequence encoded by the Arabidopsis 2490 DNA sequence shown in SEQ ID NO:5
SEQ ID NO:7 cDNA sequence for the Arabidopsis 3963 gene
SEQ ID NO:8 amino acid sequence encoded by the Arabidopsis 3963 DNA sequence shown in SEQ ID NO:7
SEQ ID NO:9 cDNA sequence for the Arabidopsis 4036 gene
SEQ ID NO:10 amino acid sequence encoded by the Arabidopsis 4036 DNA sequence shown in SEQ ID NO:9
SEQ ID NO:11 oligonucleotide SLP346for
SEQ ID NO:12 partial genomic sequence of the Arabidopsis 245 gene
SEQ ID NO:13 3'UTR from the cDNA sequence for the Arabidopsis 245 gene
SEQ ID NO:14 genomic sequence of the Arabidopsis 5283 gene
SEQ ID NO:15 oligonucleotide SLP328
SEQ ID NO:16 oligonucleotide LW60
SEQ ID NO:17 5'UTR from the cDNA sequence for the Arabidopsis 5283 gene
SEQ ID NO:18 3'UTR from the cDNA sequence for the Arabidopsis 5283 gene
SEQ ID NO:19 genomic sequence of the Arabidopsis 2490 gene
SEQ ID NO:20 5'UTR from the cDNA for the Arabidopsis 2490 gene
SEQ ID NO:21 3'UTR from the cDNA sequence for the Arabidopsis 2490 gene
SEQ ID NO:22 oligonucleotide SLP369
SEQ ID NO:23 oligonucleotide SLP370
SEQ ID NO:24 genomic sequence of the Arabidopsis 3963 gene
SEQ ID NO:25 oligonucleotide -21
SEQ ID NO:26 3'UTR from the cDNA sequence for the Arabidopsis 3963 gene
SEQ ID NO:27 genomic sequence of the Arabidopsis 4036 gene
SEQ ID NO:28 cDNA coding sequence for the Arabidopsis 4036 gene including variations between the cDNA and genomic sequence from cultivars Landsberg and Columbia
SEQ ID NO:29 amino acid sequence encoded by the Arabidopsis 4036 DNA sequence shown in SEQ ID NO:28

DETAILED DESCRIPTION OF THE INVENTION

I. Essentiality of the 245 Gene, 5283 Gene, 2490 Gene, 3963 Gene, or 4036 Gene in Arabidopsis Demonstrated by T-DNA Insertion Mutagenesis As shown in the examples below, the identification of a novel gene structure, as well as the essentiality of the 245 gene, 5283 gene, 2490 gene, 3963 gene or 4036 gene for normal plant growth and development, have been demonstrated for the first time in Arabidopsis using T-DNA insertion mutagenesis. Having established the essentiality of 245, 5283, 2490, 3963 or 4036 function in plants and having identified the genes encoding these essential activities, the inventors thereby provide an important and sought after tool for new herbicide development.

Arabidopsis insertional mutant lines segregating for seedling lethal mutations are identified as a first step in the identification of essential proteins. Starting with T2 seeds collected from single T1 plants containing T-DNA insertions in their genomes, those lines segregating homozygous seedling lethal seedlings are identified. These lines are found by placing seeds onto minimal plant growth media, which contains the fungicides benomyl and maxim, and screening for inviable seedlings after 7 and 14 days in the light at room temperature. Inviable phenotypes include altered pigmentation or altered morphology. These phenotypes are observed either on plates directly or in soil following transplantation of seedlings.

When a line is identified as segregating a seedling lethal, it is determined if the resistance marker in the T-DNA co-segregates with the lethality (Errampalli et al. (1991) The Plant Cell, 3:149–157). Co-segregation analysis is done by placing the seeds on media containing the selective agent and scoring the seedlings for resistance or sensitivity to the agent. Examples of selective agents used are hygromycin or phosphinothricin. About 35 resistant seedlings are transplanted to soil and their progeny are examined for the segregation of the seedling lethal. In the case in which the T-DNA insertion disrupts an essential gene, there is co-segregation of the resistance phenotype and the seedling lethal phenotype in every plant. Therefore, in such a case, all resistant plants segregate seedling lethals in the next generation; this result indicates that each of the resistant plants is heterozygous for the DNA causing both phenotypes.

For those lines showing co-segregation of the T-DNA resistance marker and the seedling lethal phenotype, Southern analysis is performed as an initial step in the characterization of the molecular nature of each insertion. Southerns are done with genomic DNA isolated from heterozygotes and using probes capable of hybridizing with the T-DNA vector DNA. Using the results of the Southern analysis, appropriate restriction enzymes are chosen to perform plasmid rescue in order to molecularly clone Arabidopsis genomic DNA flanking one or both sides of the T-DNA insertion. Plasmids obtained in this manner are analyzed by restriction enzyme digestion to sort the plasmids into classes based on their digestion pattern. For each class of plasmid clone, the DNA sequence is determined. The resulting sequences are analyzed for the presence of non-T-DNA vector sequences. When such sequences are found, they are used to search DNA and protein databases using the BLAST and BLAST2 programs (Altschul et al. (1990) J Mol. Biol. 215: 403–410; Altschul et al (1997) Nucleic Acid Res. 25:3389–3402). Additional genomic and cDNA sequences for each gene are identified by standard molecular biology procedures.

II. Sequences of the Arabidopsis 245, 5283, 2490, 3963, and 4036 Genes

The Arabidopsis 245 gene is identified by isolating DNA flanking the T-DNA border from the tagged seedling-lethal line #245. A region of the Arabidopsis DNA, flanking the T-DNA border, is 99% identical to the genomic survey sequence F 17K7TR (accession #B24357). The inventors are the first to demonstrate that the 245 gene product is essential for normal growth and development in plants, as well as defining the function of the 245 gene product through protein homology. The present invention discloses the cDNA nucleotide sequence of the Arabidopsis 245 gene as well as the amino acid sequence of the Arabidopsis 245 protein. The nucleotide sequence corresponding to the cDNA clone is set forth in SEQ ID NO:1, and the amino acid sequence encoding the protein is set forth in SEQ ID NO:2. The UTR sequence found 3' to SEQ ID NO:1 is set forth in SEQ ID NO:13. The nucleotide sequence corresponding to the partial genomic DNA is set forth in SEQ ID NO:12. The present invention also encompasses an isolated amino acid sequence derived from a plant, wherein said amino acid sequence is identical or substantially similar to the amino acid sequence encoded by the nucleotide sequence set forth in SEQ ID NO:1, wherein said amino acid sequence has 245 activity. Using BLAST and BLAST2 programs with the default settings, the sequence of the 245 gene shows similarity to peptide release factor 2 from numerous prokaryotic species. Notable species similarities include: *Escherichia coli* (RF-2) [Swiss-Prot accession #P07012]; *Salmonella typhimurium* (RF-2 Salty)[Swiss-Prot accession #P28353]; and *Mycobacterium tuberculosis* (RF-2: prfB)[Swiss-Prot accession #005782]. Using GAP analysis of the following protein sequences with the 245 protein results in the following sequence identities with the 245 protein: *Escherichia coli* (RF-2) [Swiss-Prot accession #P07012](27.2% identity); *Salmonella typhimurium* (RF-2 Salty)[Swiss-Prot accession #P28353] (24.6% identity); and *Mycobacterium tuberculosis* (RF-2: prfB)[Swiss-Prot accession #005782] (27.2% identity). In addition, Synechocystis (GenPept accession #BAA18577) (31.5% identity); and P1 clone MAB16, chromosome 5 of *Arabidopsis thaliana* (Accession #AB018112NID) (46.2% identity).

The Arabidopsis 5283 gene is identified by isolating DNA flanking the T-DNA border from the tagged seedling-lethal line #5283. A region of the Arabidopsis DNA, flanking the T-DNA border is identical to an internal region of a sequenced BAC of Arabidopsis (BAC T13D8, chromosome 1). This BAC clone contains 116,177 bp of sequence, of which a very small portion corresponds to the genomic region that contains the 5283 gene. Notwithstanding the BAC information, the inventors are the first to demonstrate that the 5283 gene product is essential for normal growth and development in plants, as well as defining the function of the 5283 gene product through protein homology. The present invention discloses the cDNA nucleotide sequence of the Arabidopsis 5283 gene as well as the amino acid sequence of the Arabidopsis 5283 protein. The nucleotide sequence corresponding to the cDNA clone is set forth in SEQ ID NO:3, and the amino acid sequence encoding the protein is set forth in SEQ ID NO:4. The nucleotide sequence corresponding to the genomic DNA is set forth in SEQ ID NO:14. The nucleotide sequence corresponding to the 5'UTR from the cDNA sequence is set forth in SEQ ID NO:17, and the nucleotide sequence corresponding to the 3'UTR from the cDNA sequence is set forth in SEQ ID NO:18. The present invention also encompasses an isolated amino acid sequence derived from a plant, wherein said amino acid sequence is identical or substantially similar to the amino acid sequence encoded by the nucleotide sequence set forth in SEQ ID NO:3, wherein said amino acid sequence has 5283 activity. Using BLAST and BLAST2 programs with the default settings, the sequence of the 5283 protein shows similarity to SPBC119.13c from *S. pombe* [GENPEPT accession #CAA17928]; SAR DNA-binding proteins from plants [SARBP-1; Genbank accession #AF061962 and SARBP-2: Genbank accession

AF061963]; and prp31 and SIK1p (Nop56) from *S. cerevisiae* [PRP31: Swiss Prot accession #Q12460]. Using GAP analysis of the following protein sequences with the 5283 protein results in the following sequence identities with the 5283 protein: SPBC119.13c from *S. pombe* [GENPEPT accession #CAA17928] (40.5% identity); SAR DNA-binding proteins from plants [SARBP-1; Genbank accession #AF061962 (23.5% identity), and SARBP-2: Genbank accession #AF061963] (24.2% identity); and prp31 and SIK1p (Nop56) from *S. cerevisiae* [PRP31: Swiss Prot accession #Q12460] (24.1% identity). In addition, *Arabidopsis thaliana* (GENPEPT accession #AAC18800) results in 73.8% identity with the 5283 protein.

The Arabidopsis 2490 gene is identified by isolating DNA flanking the T-DNA border from the tagged seedling-lethal line #2490. Arabidopsis DNA flanking the T-DNA border is identical to an internal region of a sequenced P1 clone of Arabidopsis (P1 MTG13, chromosome 5). This P1 clone contains 50,641 bp of sequence, of which a small portion corresponds to the genomic region that contains the 2490 gene. The sequence of a 2490 cDNA containing the entire coding sequence for the 2490 protein is obtained by determining the sequence of the 144K24 EST clone (obtained from Michigan State University). Notwithstanding the BAC and EST sequence information, the inventors are the first to establish definitively the entire gene sequence, and to demonstrate that the 2490 gene product is essential for normal growth and development in plants, as well as defining the function of the 2490 gene product through protein homology. The present invention discloses the cDNA nucleotide sequence of the Arabidopsis 2490 gene as well as the amino acid sequence of the Arabidopsis 2490 protein. The nucleotide sequence corresponding to the cDNA clone is set forth in SEQ ID NO:5, and the amino acid sequence encoding the protein is set forth in SEQ ID NO:6. The UTR sequence found 5' to SEQ ID NO:5 is set forth in SEQ ID NO:20, and the UTR sequence found 3' to SEQ ID NO:5 is set forth in SEQ ID NO:21. The nucleotide sequence corresponding to the genomic DNA is set forth in SEQ ID NO:19. The present invention also encompasses an isolated amino acid sequence derived from a plant, wherein said amino acid sequence is identical or substantially similar to the amino acid sequence encoded by the nucleotide sequence set forth in SEQ ID NO:5, wherein said amino acid sequence has 2490 activity. Using BLAST and BLAST2 programs with the default settings, the sequence of the 2490 protein shows similarity to the Toc36 (bce42B) chloroplast envelope protein from *Brassica napus* (Ko et al. (1995) The Journal of Biological Chem. 270: 28601–28608; Wu et al. (1994) The Journal of Biological Chem. 269: 32264–32271; Pang et al. (1997) The Journal of Biological Chem. 272: 25623–25627). Using GAP analysis of the 2490 protein and the Toc36 (bce42B) chloroplast envelope protein from *Brassica napus* (Genbank accession #X79091) results in 81.7% identity with the 2490 protein.

The Arabidopsis 3963 gene is identified by isolating DNA flanking the T-DNA border from the tagged seedling-lethal line #3963. A region of the Arabidopsis DNA flanking the T-DNA border is 100% identical to the genomic sequence for P1 clone MDK4 on chromosome 5 (Genbank accession number AB010695). The inventors are the first to demonstrate that the 3963 gene product is essential for normal growth and development in plants, as well as defining the function of the 3963 gene product through protein homology. The present invention discloses the cDNA nucleotide sequence of the Arabidopsis 3963 gene as well as the amino acid sequence of the Arabidopsis 3963 protein. The nucleotide sequence corresponding to the cDNA clone is set forth in SEQ ID NO:7, and the amino acid sequence encoding the protein is set forth in SEQ ID NO:8. The UTR sequence found 3' to SEQ ID NO:7 is set forth in SEQ ID NO:26. The nucleotide sequence corresponding to the genomic DNA is set forth in SEQ ID NO:24. The present invention also encompasses an isolated amino acid sequence derived from a plant, wherein said amino acid sequence is identical or substantially similar to the amino acid sequence encoded by the nucleotide sequence set forth in SEQ ID NO:7, wherein said amino acid sequence has 3963 activity. Using BLAST and BLAST2 programs with the default settings, the sequence of the 3963 gene shows similarity to a number of DNA repair proteins, including Rad32p from *Schizosaccharomyces pombe* (Genbank accession numberQ09683); hMre11 from *Homo sapiens* (Genbank accession number U37359); and Mre11p from Saccharomyces cerevisiae (Genbank accession number U60829). Using GAP analysis of the following protein sequences with the 3963 protein results in the following sequence identities with the 3963 protein: Rad32p from *Schizosaccharomyces pombe* (Genbank accession numberQ09683) (37.5% identity); hMre11 from *Homo sapiens* (Genbank accession number U37359) (39.4% identity); and Mre11p from *Saccharomyces cerevisiae* (Genbank accession number U60829) (34.7% identity).

The Arabidopsis 4036 gene is identified by isolating DNA flanking the T-DNA border from the tagged seedling-lethal line #4036. A region of the Arabidopsis DNA flanking the T-DNA border is 100% identical to the published genomic sequence for P1 clone MQB2, from chromosome 5 of Arabidopsis (Genbank accession #AB009053). The inventors are the first to demonstrate that the 4036 gene product is essential for normal growth and development in plants, as well as defining the function of the 4036 gene through protein homology. The present invention discloses the cDNA coding nucleotide sequence of the Arabidopsis 4036 gene as well as the amino acid sequence of the Arabidopsis 4036 protein. The nucleotide sequences corresponding to the cDNA of cv. Landsberg and that of two cultivars are set forth in SEQ ID NO:9 and SEQ ID NO:28, respectively. The corresponding amino acid sequences encoding the proteins are set forth in SEQ ID NO:10 and SEQ ID NO:29. The nucleotide sequence corresponding to the genomic DNA is set forth in SEQ ID NO:27. Thirteen nucleotide differences are observed by comparing the cDNA clone, derived from cv. Landsberg, and the genomic sequence, derived from cv. Columbia, and these variations are listed below in Table 1.

TABLE 1

Nucleotide Differences Observed Between the 4036 cDNA Clone, from cv. Landsberg, and the 4036 Genomic Sequence, from cv. Columbia

| Nucleotide #* difference | cv. Landsberg | cv. Columbia | Codon containing nucleotide (amino acid residue in cv. Landsberg and amino acid residue in cv. Columbia)** |
| --- | --- | --- | --- |
| 115 | G | A | GAT to AAT (Asp to Asn) |
| 207 | T | C | GTT to GTC (Val to Val) |
| 273 | C | T | TCC to TCT (Ser to Ser) |
| 276 | C | T | ATC to ATT (Ile to Ile) |
| 321 | T | C | TTT to TTC (Phe to Phe) |
| 393 | G | A | GCG to GCA (Ala to Ala) |
| 485 | T | A | CTA to CAA (Leu to Gln) |
| 464 | C | T | CCC to CTC (Pro to Leu) |
| 559 | A | C | AAG to CAG (Lys to Gln) |
| 963 | T | G | CCT to CCG (Pro to Pro) |

TABLE 1-continued

Nucleotide Differences Observed Between the 4036 cDNA Clone, from cv. Landsberg, and the 4036 Genomic Sequence, from cv. Columbia

| Nucleotide #* difference | cv. Landsberg | cv. Columbia | Codon containing nucleotide (amino acid residue in cv. Landsberg and amino acid residue in cv. Columbia)** |
|---|---|---|---|
| 1101 | T | A | CCT to CCA (Pro to Pro) |
| 1254 | T | C | TTT to TTC (Phe to Phe) |
| 1393 | G | A | GAT to AAT (Asp to Asn) |

*SEQ ID NO:9 used as a reference for nucleotide numbering
**Amino acid residues: Ala (alanine); Asn (asparagine); Asp (aspartic acid); Gln (glutamine); Ile (isoleucine); Leu (leucine); Lys (lysine); Phe (phenylalanine); Pro (proline); Ser (serine); and Val (valine)

The present invention also encompasses an isolated amino acid sequence derived from a plant, wherein said amino acid sequence is identical or substantially similar to the amino acid sequence encoded by the nucleotide sequence set forth in SEQ ID NO:9, wherein said amino acid sequence has 4036 activity. Using BLAST and BLAST2 programs with the default settings, the sequence of the 4036 gene shows similarity to 1-deoxy-D-xylulose 5-phosphate reductoisomerase from a number of organisms including Synechocystis sp. (SWISS-PROTQ55663), *Bacillus subtilis* (SWISS-PROT 031753), and *Escherichia coli* (SWISS-PROT P45568) (Takahashi et al. (1998) Proc. Natl. Acad. Sci. USA, 95: 9879–9884). Using GAP analysis of the following protein sequences with the 4036 protein results in the following sequence identities with the 4036 protein: 1-deoxy-D-xylulose 5-phosphate reductoisomerase from Synechocystis sp. (SWISS-PROTQ55663) (66.1% identity); *Bacillus subtilis* (SWISS-PROT 031753) (45.4% identity); and *Escherichia coli* (SWISS-PROT P45568) (44.6% identity) (Takahashi et al. (1998) Proc. Natl. Acad. Sci. USA, 95: 9879–9884).

III. Recombinant Production of 245, 5283, 2490, 3963, or 4036 Activity and Uses Thereof For recombinant production of 245, 5283, 2490, 3963 or 4036 activity in a host organism, a nucleotide sequence encoding a protein having 245, 5283, 2490, 3963 or 4036 activity is inserted into an expression cassette designed for the chosen host and introduced into the host where it is recombinantly produced. For example, SEQ ID NO:1 or SEQ ID NO:1 associated with SEQ ID NO:13 as a 3' UTR, nucleotide sequences substantially similar to SEQ ID NO:1, or homologs of the 245 coding sequence can be used for the recombinant production of a protein having 245 activity. The choice of specific regulatory sequences such as promoter, signal sequence, 5' and 3' untranslated sequences, and enhancer appropriate for the chosen host is within the level of skill of the routineer in the art. The resultant molecule, containing the individual elements operably linked in proper reading frame, may be inserted into a vector capable of being transformed into the host cell. Suitable expression vectors and methods for recombinant production of proteins are well known for host organisms such as *E. coli*, yeast, and insect cells (see, e.g., Luckow and Summers, *Bio/Technol*. 6: 47 (1988), and baculovirus expression vectors, e.g., those derived from the genome of *Autographica californica* nuclear polyhedrosis virus (AcMNPV). A preferred baculovirus/insect system is pAcHLT (Pharmingen, San Diego, Calif.) used to transfect *Spodoptera frugiperda* Sf9 cells (ATCC) in the presence of linear *Autographa californica* baculovirus DNA (Pharmigen, San Diego, Calif.). The resulting virus is used to infect HighFive *Tricoplusia ni* cells (Invitrogen, La Jolla, Calif.). In a similar fashion, recombinant production of 5283, 2490, 3963, or 4036 activity is obtained.

In a preferred embodiment, the nucleotide sequence encoding a protein having 245, 5283, 2490, 3963 or 4036 activity is derived from an eukaryote, such as a mammal, a fly or a yeast, but is preferably derived from a plant. In a further preferred embodiment, the nucleotide sequence is identical or substantially similar to the nucleotide sequence set forth in SEQ ID NO:1, SEQ ID NO:3, SEQ ID NO:5, SEQ ID NO:7 or SEQ ID NO:9 respectively or encodes a protein having 245, 5283, 2490, 3963 or 4036 activity, respectively, whose amino acid sequence is identical or substantially similar to the amino acid sequence set forth in SEQ ID NO:2, SEQ ID NO:4, SEQ ID NO:6, SEQ ID NO:8 or SEQ ID NO:10 respectively. The nucleotide sequence set forth in SEQ ID NO:1, SEQ ID NO:3, SEQ ID NO:5, SEQ ID NO:7 or SEQ ID NO:9 encodes the Arabidopsis 245 protein, Arabidopsis 5283 protein, Arabidopsis 2490 protein, Arabidopsis 3963 protein or Arabidopsis 4036 protein, whose amino acid sequence is set forth in SEQ ID NO:2, SEQ ID NO:4, SEQ ID NO:6, SEQ ID NO:8 or SEQ ID NO:10 respectively. In another preferred embodiment, the nucleotide sequence is derived from a prokaryote, preferably a bacteria, e.g. *E. coli*. Recombinantly produced protein having 245, 5283, 2490, 3963 or 4036 activity is isolated and purified using a variety of standard techniques. The actual techniques that may be used will vary depending upon the host organism used, whether the protein is designed for secretion, and other such factors familiar to the skilled artisan (see, e.g. chapter 16 of Ausubel, F. et al., "Current Protocols in Molecular Biology", pub. by John Wiley & Sons, Inc. (1994).

Assays Utilizing the 245, 5283, 2490, 3963, or 4036 Protein

Recombinantly produced proteins having 245, 5283, 2490, 3963 or 4036 activity are useful for a variety of purposes. For example, they can be used in in vitro assays to screen known herbicidal chemicals whose target has not been identified to determine if they inhibit 245, 5283, 2490, 3963 or 4036 activity. Such in vitro assays may also be used as more general screens to identify chemicals that inhibit such enzymatic activity and that are therefore novel herbicide candidates. Alternatively, recombinantly produced proteins having 245, 5283, 2490, 3963 or 4036 activity may be used to elucidate the complex structure of these molecules and to further characterize their association with known inhibitors in order to rationally design new inhibitory herbicides as well as herbicide tolerant forms of the enzymes. In Vitro Inhibitor Assays: Discovery of Small Molecule Ligand that Interacts with the Gene Product of SEQ ID NO:1, SEQ ID NO:3, SEQ ID NO:5, SEQ ID NO:7, or SEQ ID NO:9 respectively.

Once a protein has been identified as a potential herbicide target, the next step is to develop an assay that allows screening a large number of chemicals to determine which ones interact with the protein. Although it is straightforward to develop assays for proteins of known function, developing assays with proteins of unknown functions is more difficult.

This difficulty can be overcome by using technologies that can detect interactions between a protein and a compound without knowing the biological function of the protein. A short description of three methods is presented, including fluorescence correlation spectroscopy, surface-enhanced laser desorption/ionization, and biacore technologies.

Fluorescence Correlation Spectroscopy (FCS) theory was developed in 1972 but it is only in recent years that the technology to perform FCS became available (Madge et al. (1972) Phys. Rev. Lett., 29: 705–708; Maiti et al. (1997) Proc. Natl. Acad. Sci. USA, 94: 11753–11757). FCS measures the average diffusion rate of a fluorescent molecule within a small sample volume. The sample size can be as low as 10' fluorescent molecules and the sample volume as low as the cytoplasm of a single bacterium. The diffusion rate is a function of the mass of the molecule and decreases as the mass increases. FCS can therefore be applied to protein-ligand interaction analysis by measuring the change in mass and therefore in diffusion rate of a molecule upon binding. In a typical experiment, the target to be analyzed is expressed as a recombinant protein with a sequence tag, such as a poly-histidine sequence, inserted at the N or C-terminus. The expression takes place in E. coli, yeast or insect cells. The protein is purified by chromatography. For example, the poly-histidine tag can be used to bind the expressed protein to a metal chelate column such as Ni2+ chelated on iminodiacetic acid agarose. The protein is then labeled with a fluorescent tag such as carboxytetramethyl-rhodamine or BODIPY® (Molecular Probes, Eugene, Oreg.). The protein is then exposed in solution to the potential ligand, and its diffusion rate is determined by FCS using instrumentation available from Carl Zeiss, Inc. (Thornwood, N.Y.). Ligand binding is determined by changes in the diffusion rate of the protein.

Surface-Enhanced Laser Desorption/Ionization (SELDI) was invented by Hutchens and Yip during the late 1980's (Hutchens and Yip (1993) Rapid Commun. Mass Spectrom. 7: 576–580). When coupled to a time-of-flight mass spectrometer (TOF), SELDI provides a mean to rapidly analyze molecules retained on a chip. It can be applied to ligand-protein interaction analysis by covalently binding the target protein on the chip and analyze by MS the small molecules that bind to this protein (Worrall et al. (1998) Anal. Biochem. 70: 750–756). In a typical experiment, the target to be analyzed is expressed as described for FCS. The purified protein is then used in the assay without further preparation. It is bound to the SELDI chip either by utilizing the poly-histidine tag or by other interaction such as ion exchange or hydrophobic interaction. The chip thus prepared is then exposed to the potential ligand via, for example, a delivery system capable to pipet the ligands in a sequential manner (autosampler). The chip is then submitted to washes of increasing stringency, for example a series of washes with buffer solutions containing an increasing ionic strength. After each wash, the bound material is analyzed by submitting the chip to SELDI-TOF. Ligands that specifically bind the target will be identified by the stringency of the wash needed to elute them.

Biacore relies on changes in the refractive index at the surface layer upon binding of a ligand to a protein immobilized on the layer. In this system, a collection of small ligands is injected sequentially in a 2–5 ul cell with the immobilized protein. Binding is detected by surface plasmon resonance (SPR) by recording laser light refracting from the surface. In general, the refractive index change for a given change of mass concentration at the surface layer, is practically the same for all proteins and peptides, allowing a single method to be applicable for any protein (Liedberg et al. (1983) Sensors Actuators 4: 299–304; Malmquist (1993) Nature, 361: 186–187). In a typical experiment, the target to be analyzed is expressed as described for FCS. The purified protein is then used in the assay without further preparation. It is bound to the Biacore chip either by utilizing the poly-histidine tag or by other interaction such as ion exchange or hydrophobic interaction. The chip thus prepared is then exposed to the potential ligand via the delivery system incorporated in the instruments sold by Biacore (Uppsala, Sweden) to pipet the ligands in a sequential manner (autosampler). The SPR signal on the chip is recorded and changes in the refractive index indicate an interaction between the immobilized target and the ligand. Analysis of the signal kinetics on rate and off rate allows the discrimination between non-specific and specific interaction.

Also, an assay for small molecule ligands that interact with a polypeptide is an inhibitor assay. For example, such an inhibitor assay useful for identifying inhibitors of essential plant genes, such as 245, 5283, 2490, 3963, or 4036 genes, comprises the steps of:

a) reacting a plant 245, 5283, 2490, 3963, or 4036 protein and a substrate thereof in the presence of a suspected inhibitor of the protein's function;

b) comparing the rate of enzymatic activity in the presence of the suspected inhibitor to the rate of enzymatic activity under the same conditions in the absence of the suspected inhibitor; and c) determining whether the suspected inhibitor inhibits the 245, 5283, 2490, 3963, or 4036 protein.

For example, the inhibitory effect on plant 245, 5283, 2490, 3963, or 4036 protein may be determined by a reduction or complete inhibition of 245, 5283, 2490, 3963, or 4036 activity in the assay. Such a determination may be made by comparing, in the presence and absence of the candidate inhibitor, the amount of substrate used or intermediate or product made during the reaction.

IV. In vivo Inhibitor Assay

In one embodiment, a suspected herbicide, for example identified by in vitro screening, is applied to plants at various concentrations. The suspected herbicide is preferably sprayed on the plants. After application of the suspected herbicide, its effect on the plants, for example death or suppression of growth, is recorded.

In another embodiment, an in vivo screening assay for inhibitors of the 245, 5283, 2490, 3963 or 4036 activity uses transgenic plants, plant tissue, plant seeds or plant cells capable of overexpressing a nucleotide sequence having 245, 5283, 2490, 3963 or 4036 activity, wherein the 245, 5283, 2490, 3963 or 4036 gene product is enzymatically active in the transgenic plants, plant tissue, plant seeds or plant cells. The nucleotide sequence is preferably derived from an eukaryote, such as a yeast, but is preferably derived from a plant. In a further preferred embodiment, the nucleotide sequence is identical or substantially similar to the nucleotide sequence set forth in SEQ ID NO:1, SEQ ID NO:3, SEQ ID NO:5, SEQ ID NO:7, or SEQ ID NO:9, or encodes an enzyme having 245, 5283, 2490, 3963 or 4036 activity, whose amino acid sequence is identical or substantially similar to the amino acid sequence set forth in SEQ ID NO:2, SEQ ID NO:4, SEQ ID NO:6, SEQ ID NO:8 or SEQ ID NO:10 respectively. In another preferred embodiment, the nucleotide sequence is derived from a prokaryote, preferably a bacteria, e.g. E. coli.

A chemical is then applied to the transgenic plants, plant tissue, plant seeds or plant cells and to the isogenic non-transgenic plants, plant tissue, plant seeds or plant cells, and the growth or viability of the transgenic and non-transformed plants, plant tissue, plant seeds or plant cells are determined after application of the chemical and compared. Compounds capable of inhibiting the growth of the non-transgenic plants, but not affecting the growth of the transgenic plants are selected as specific inhibitors of 245, 5283, 2490, 3963 or 4036 activity.

V. Herbicide Tolerant Plants

The present invention is further directed to plants, plant tissue, plant seeds, and plant cells tolerant to herbicides that inhibit the naturally occurring 245, 5283, 2490, 3963 or 4036 activity in these plants, wherein the tolerance is conferred by an altered 245, 5283, 2490, 3963 or 4036 activity respectively. Altered 245, 5283, 2490, 3963 or 4036 activity may be conferred upon a plant according to the invention by increasing expression of wild-type herbicide-sensitive 245, 5283, 2490, 3963 or 4036 gene, for example by providing additional wild-type 245, 5283, 2490, 3963 or 4036 genes and/or by overexpressing the endogenous 245, 5283, 2490, 3963 or 4036 gene respectively, for example by driving expression with a strong promoter. Altered 245, 5283, 2490, 3963 or 4036 activity also may be accomplished by expressing nucleotide sequences that are substantially similar to SEQ ID NO:1, SEQ ID NO:3, SEQ ID NO:5, SEQ ID NO:7, or SEQ ID NO:9 respectively or homologs thereof in a plant. Still further altered 245, 5283, 2490, 3963 or 4036 activity is conferred on a plant by expressing modified herbicide-tolerant 245, 5283, 2490, 3963 or 4036 genes respectively in the plant. Combinations of these techniques may also be used. Representative plants include any plants to which these herbicides are applied for their normally intended purpose. Preferred are agronomically important crops such as cotton, soybean, oilseed rape, sugar beet, maize, rice, wheat, barley, oats, rye, sorghum, millet, turf, forage, turf grasses, and the like.

A. Increased Expression of Wild-Type 245, 5283, 2490, 3963, or 4036

Achieving altered 245 activity or 5283, 2490, 3963 4036 activity respectively through increased expression results in a level of 245 activity or 5283, 2490, 3963, 4036 activity respectively in the plant cell at least sufficient to overcome growth inhibition caused by the herbicide when applied in amounts sufficient to inhibit normal growth of control plants. The level of expressed enzyme generally is at least two times, preferably at least five times, and more preferably at least ten times the natively expressed amount. Increased expression may be due to multiple copies of a wild-type 245 gene or 5283, 2490, 3963 or 4036 gene respectively; multiple occurrences of the coding sequence within the gene (i.e. gene amplification) or a mutation in the non-coding, regulatory sequence of the endogenous gene in the plant cell. Plants having such altered gene activity can be obtained by direct selection in plants by methods known in the art (see, e.g. U.S. Pat. No. 5,162,602, and U.S. Pat. No. 4,761,373, and references cited therein). These plants also may be obtained by genetic engineering techniques known in the art. Increased expression of a herbicide-sensitive 245 gene or 5283, 2490, 3963 or 4036 gene respectively can also be accomplished by transforming a plant cell with a recombinant or chimeric DNA molecule comprising a promoter capable of driving expression of an associated structural gene in a plant cell operatively linked to a homologous or heterologous structural gene encoding the 245 protein or the 5283, 2490, 3963 or 4036 protein respectively or a homolog thereof Preferably, the transformation is stable, thereby providing a heritable transgenic trait.

B. Expression of Modified Herbicide-Tolerant 245, 5283, 2490, 3963, or 4036 Proteins According to this embodiment, plants, plant tissue, plant seeds, or plant cells are stably transformed with a recombinant DNA molecule comprising a suitable promoter functional in plants operatively linked to a coding sequence encoding a herbicide tolerant form of the 245, 5283, 2490, 3963 or 4036 protein respectively. A herbicide tolerant form of the enzyme has at least one amino acid substitution, addition or deletion that confers tolerance to a herbicide that inhibits the unmodified, naturally occurring form of the enzyme. The transgenic plants, plant tissue, plant seeds, or plant cells thus created are then selected by conventional selection techniques, whereby herbicide tolerant lines are isolated, characterized, and developed. Below are described methods for obtaining genes that encode herbicide tolerant forms of 245, 5283, 2490, 3963 or 4036 protein respectively:

One general strategy involves direct or indirect mutagenesis procedures on microbes. For instance, a genetically manipulatable microbe such as *E. Coli* or *S. cerevisiae* may be subjected to random mutagenesis in vivo with mutagens such as UV light or ethyl or methyl methane sulfonate. Mutagenesis procedures are described, for example, in Miller, *Experiments in Molecular Genetics*, Cold Spring Harbor Laboratory, Cold Spring Harbor, N.Y. (1972); Davis et al., *Advanced Bacterial Genetics*, Cold Spring Harbor Laboratory, Cold Spring Harbor, N.Y. (1980); Sherman et al., *Methods in Yeast Genetics*, Cold Spring Harbor Laboratory, Cold Spring Harbor, N.Y. (1983); and U.S. Pat. No. 4,975,374. The microbe selected for mutagenesis contains a normal, inhibitor-sensitive 245, 5283, 2490, 3963 or 4036 gene respectively and is dependent upon the activity conferred by this gene. The mutagenized cells are grown in the presence of the inhibitor at concentrations that inhibit the unmodified gene. Colonies of the mutagenized microbe that grow better than the unmutagenized microbe in the presence of the inhibitor (i.e. exhibit resistance to the inhibitor) are selected for further analysis. 245, 5283, 2490, 3963 or 4036 genes respectively conferring tolerance to the inhibitor are isolated from these colonies, either by cloning or by PCR amplification, and their sequences are elucidated. Sequences encoding altered gene products are then cloned back into the microbe to confirm their ability to confer inhibitor tolerance.

A method of obtaining mutant herbicide-tolerant alleles of a plant 245, 5283, 2490, 3963 or 4036 gene involves direct selection in plants. For example, the effect of a mutagenized 245, 5283, 2490, 3963 or 4036 gene on the growth inhibition of plants such as Arabidopsis, soybean, or maize is determined by plating seeds sterilized by art-recognized methods on plates on a simple minimal salts medium containing increasing concentrations of the inhibitor. Such concentrations are in the range of 0.001, 0.003, 0.01, 0.03, 0.1, 0.3, 1, 3, 10, 30, 110, 300, 1000 and 3000 parts per million (ppm). The lowest dose at which significant growth inhibition can be reproducibly detected is used for subsequent experiments. Determination of the lowest dose is routine in the art.

Mutagenesis of plant material is utilized to increase the frequency at which resistant alleles occur in the selected population. Mutagenized seed material is derived from a variety of sources, including chemical or physical mutagenesis or seeds, or chemical or physical mutagenesis or pollen (Neuffer, In *Maize for Biological Research* Sheridan, ed. Univ. Press, Grand Forks, N.Dak., pp. 61–64 (1982)), which is then used to fertilize plants and the resulting $M_1$ mutant seeds collected. Typically for Arabidopsis, $M_2$ seeds (Lehle Seeds, Tucson, Ariz.), which are progeny seeds of plants grown from seeds mutagenized with chemicals, such as ethyl methane sulfonate, or with physical agents, such as gamma rays or fast neutrons, are plated at densities of up to 10,000 seeds/plate (10 cm diameter) on minimal salts medium containing an appropriate concentration of inhibitor to select for tolerance. Seedlings that continue to grow and remain green 7–21 days after plating are transplanted to soil and grown to maturity and seed set. Progeny of these seeds are tested for tolerance to the herbicide. If the tolerance trait is dominant, plants whose seed segregate 3:1/resistant:sensitive are presumed to have been heterozygous for the resistance at the $M_2$ generation. Plants that give rise to all resistant seed are presumed to have been homozygous for the resistance at the $M_2$ generation. Such mutagenesis on intact seeds and screening of their M2 progeny seed can also be carried out on other species, for instance soybean (see, e.g. U.S. Pat. No. 5,084,082). Alternatively, mutant seeds to be screened for herbicide tolerance are obtained as a result of fertilization with pollen mutagenized by chemical or physical means.

Confirmation that the genetic basis of the herbicide tolerance is a 245, 5283, 2490, 3963 or 4036 gene respectively is ascertained as exemplified below. First, alleles of the 245, 5283, 2490, 3963 or 4036 gene respectively from plants exhibiting resistance to the inhibitor are isolated using PCR with primers based either upon the Arabidopsis cDNA coding sequences shown in SEQ ID NO:1, SEQ ID NO:3, SEQ ID NO:5, SEQ ID NO:7, or SEQ ID NO:9 respectively or, more preferably, based upon the unaltered 245, 5283, 2490, 3963 or 4036 gene sequence from the plant used to generate tolerant alleles. After sequencing the alleles to determine the presence of mutations in the coding sequence, the alleles are tested for their ability to confer tolerance to the inhibitor on plants into which the putative tolerance-conferring alleles have been transformed. These plants can be either Arabidopsis plants or any other plant whose growth is susceptible to the 245, 5283, 2490, 3963 or 4036 inhibitors respectively. Second, the inserted 245, 5283, 2490, 3963 or 4036 genes are mapped relative to known restriction fragment length polymorphisms (RFLPs) (See, for example, Chang et al. *Proc. Natl. Acad, Sci, USA* 85: 6856–6860 (1988); Nam et al., *Plant Cell* 1: 699–705 (1989), cleaved amplified polymorphic sequences (CAPS) (Konieczny and Ausubel (1993) The Plant Journal, 4(2): 403–410), or SSLPs (Bell and Ecker (1994) Genomics, 19: 137–144). The 245, 5283, 2490, 3963 or 4036 inhibitor tolerance trait respectively is independently mapped using the same markers. When tolerance is due to a mutation in that 245, 5283, 2490, 3963 or 4036 gene respectively, the tolerance trait maps to a position indistinguishable from the position of the 245, 5283, 2490, 3963 or 4036 gene.

Another method of obtaining herbicide-tolerant alleles of a 245, 5283, 2490, 3963 or 4036 gene is by selection in plant cell cultures. Explants of plant tissue, e.g. embryos, leaf disks, etc. or actively growing callus or suspension cultures of a plant of interest are grown on medium in the presence of increasing concentrations of the inhibitory herbicide or an analogous inhibitor suitable for use in a laboratory environment. Varying degrees of growth are recorded in different cultures. In certain cultures, fast-growing variant colonies arise that continue to grow even in the presence of normally inhibitory concentrations of inhibitor. The frequency with which such faster-growing variants occur can be increased by treatment with a chemical or physical mutagen before exposing the tissues or cells to the inhibitor. Putative tolerance-conferring alleles of the 245, 5283, 2490, 3963 or 4036 gene respectively are isolated and tested as described in the foregoing paragraphs. Those alleles identified as conferring herbicide tolerance may then be engineered for optimal expression and transformed into the plant. Alternatively, plants can be regenerated from the tissue or cell cultures containing these alleles.

Still another method involves mutagenesis of wild-type, herbicide sensitive plant 245, 5283, 2490, 3963 or 4036 genes respectively in bacteria or yeast, followed by culturing the microbe on medium that contains inhibitory concentrations (i.e. sufficient to cause abnormal growth, inhibit growth or cause cell death) of the inhibitor, and then selecting those colonies that grow normally in the presence of the inhibitor. More specifically, a plant cDNA, such as the Arabidopsis cDNA encoding the 245, 5283, 2490, 3963 or 4036 protein respectively, is cloned into a microbe that otherwise lacks the 245, 5283, 2490, 3963 or 4036 activity respectively. The transformed microbe is then subjected to in vivo mutagenesis or to in vitro mutagenesis by any of several chemical or enzymatic methods known in the art, e.g. sodium bisulfite (Shortle et al., *Methods Enzymol.* 100:457–468 (1983); methoxylamine (Kadonaga et al., *Nucleic Acids Res.* 13:1733–1745 (1985); oligonucleotide-directed saturation mutagenesis (Hutchinson et al., *Proc. Natl. Acad. Sci. USA*, 83:710–714 (1986); or various polymerase misincorporation strategies (see, e.g. Shortle et al., Proc. Natl. Acad. Sci. USA, 79:1588–1592 (1982); Shiraishi et al., *Gene* 64:313–319 (1988); and Leung et al, *Technique* 1:11–15 (1989). Colonies that grow normally in the presence of normally inhibitory concentrations of inhibitor are picked and purified by repeated restreaking. Their plasmids are purified and tested for the ability to confer tolerance to the inhibitor by retransforming them into the microbe lacking 245, 5283, 2490, 3963 or 4036 activity respectively. The DNA sequences of cDNA inserts from plasmids that pass this test are then determined.

Herbicide resistant 245, 5283, 2490, 3963 or 4036 proteins respectively are also obtained using methods involving in vitro recombination, also called DNA shuffling. By DNA shuffling, mutations, preferably random mutations, are introduced into nucleotide sequences encoding 245, 5283, 2490, 3963 or 4036 activity respectively. DNA shuffling also leads to the recombination and rearrangement of sequences within a 245, 5283, 2490, 3963 or 4036 gene respectively or to recombination and exchange of sequences between two or more different of 245, 5283, 2490, 3963 or 4036 genes respectively. These methods allow for the production of millions of mutated 245, 5283, 2490, 3963 or 4036 coding sequences respectively. The mutated genes, or shuffled genes, are screened for desirable properties, e.g. improved tolerance to herbicides and for mutations that provide broad spectrum tolerance to the different classes of inhibitor chemistry. Such screens are well within the skills of a routineer in the art.

In a preferred embodiment, a mutagenized 245, 5283, 2490, 3963 or 4036 gene respectively is formed from at least one template 245, 5283, 2490, 3963 or 4036 gene respectively, wherein the template 245, 5283, 2490, 3963 or 4036 gene respectively has been cleaved into double-stranded random fragments of a desired size, and comprising the steps of adding to the resultant population of double-stranded random fragments one or more single or double-stranded oligonucleotides, wherein said oligonucleotides comprise an area of identity and an area of heterology to the double-stranded random fragments; denaturing the resultant mixture of double-stranded random fragments and oligonucleotides into single-stranded fragments; incubating the resultant population of single-stranded fragments with a polymerase under conditions which result in the annealing of said single-stranded fragments at said areas of identity to form pairs of annealed fragments, said areas of identity being sufficient for one member of a pair to prime replication of the other, thereby forming a mutagenized doublestranded polynucleotide; and repeating the second and third steps for at least two further cycles, wherein the resultant mixture in the second step of a further cycle includes the mutagenized double-stranded polynucleotide from the third step of the previous cycle, and the further cycle forms a further mutagenized double-stranded. polynucleotide, wherein the mutagenized polynucleotide is a mutated 245, 5283, 2490, 3963 or 4036 gene respectively having enhanced tolerance to a herbicide which inhibits naturally occurring 245, 5283, 2490, 3963 or 4036 activity respectively. In a preferred embodiment, the concentration of a single species of double-stranded random fragment in the population of double-stranded random fragments is less than 1% by weight of the total DNA. In a further preferred embodiment, the template double-stranded polynucleotide comprises at least about 100 species of polynucleotides. In another preferred embodiment, the size of the double-stranded random fragments is from about 5 bp to 5 kb. In a further preferred embodiment, the fourth step of the method comprises repeating the second and the third steps for at least 10 cycles. Such method is described e.g. in Stemmer et al. (1994) Nature 370: 389–391, in U.S. Pat. No. 5,605,793, U.S. Pat. No. 5,811,238 and in Crameri et al. (1998) Nature 391: 288–291, as well as in WO 97/20078, and these references are incorporated herein by reference.

In another preferred embodiment, any combination of two or more different 245 genes are mutagenized in vitro by a staggered extension process (StEP), as described e.g. in Zhao et al. (1998) Nature Biotechnology 16: 258–261. The two or more 245 genes are used as template for PCR amplification with the extension cycles of the PCR reaction preferably carried out at a lower temperature than the optimal polymerization temperature of the polymerase. In a similar fashion, the StEP is performed with the 5283, 2490, 3963, or 4036 genes. For example, when a thermostable polymerase with an optimal temperature of approximately 72° C. is used, the temperature for the extension reaction is desirably below 72° C., more desirably below 65° C., preferably below 60° C., more preferably the temperature for the extension reaction is 55° C. Additionally, the duration of the extension reaction of the PCR cycles is desirably shorter than usually carried out in the art, more desirably it is less than 30 seconds, preferably it is less than 15 seconds, more preferably the duration of the extension reaction is 5 seconds. Only a short DNA fragment is polymerized in each extension reaction, allowing template switch of the extension products between the starting DNA molecules after each cycle of denaturation and annealing, thereby generating diversity among the extension products. The optimal number of cycles in the PCR reaction depends on the length of the 245, 5283, 2490, 3963 or 4036 genes respectively to be mutagenized but desirably over 40 cycles, more desirably over 60 cycles, preferably over 80 cycles are used. Optimal extension conditions and the optimal number of PCR cycles for every combination of 245, 5283, 2490, 3963 or 4036 genes respectively are determined as described in using procedures well-known in the art. The other parameters for the PCR reaction are essentially the same as commonly used in the art. The primers for the amplification reaction are preferably designed to anneal to DNA sequences located outside of the 245, 5283, 2490, 3963 or 4036 genes, e.g. to DNA sequences of a vector comprising the 245, 5283, 2490, 3963 or 4036 genes respectively, whereby the different 245, 5283, 2490, 3963 or 4036 genes respectively used in the PCR reaction are preferably comprised in separate vectors. The primers desirably anneal to sequences located less than 500 bp away from 245, 5283, 2490, 3963 or 4036 respectively sequences, preferably less than 200 bp, more preferably less than 120 bp away from the 245, 5283, 2490, 3963 or 4036 sequences respectively. Preferably, the 245, 5283, 2490, 3963 or 4036 sequences respectively are surrounded by restriction sites, which are included in the DNA sequence amplified during the PCR reaction, thereby facilitating the cloning of the amplified products into a suitable vector. In another preferred embodiment, fragments of 245, 5283, 2490, 3963 or 4036 genes respectively having cohesive ends are produced as described in WO 98/05765. The cohesive ends are produced by ligating a first oligonucleotide corresponding to a part of a 245, 5283, 2490, 3963 or 4036 gene respectively to a second oligonucleotide not present in the gene or corresponding to a part of the gene not adjoining to the part of the gene corresponding to the first oligonucleotide, wherein the second oligonucleotide contains at least one ribonucleotide. A double-stranded DNA is produced using the first oligonucleotide as template and the second oligonucleotide as primer. The ribonucleotide is cleaved and removed. The nucleotide(s) located 5' to the ribonucleotide is also removed, resulting in double-stranded fragments having cohesive ends. Such fragments are randomly reassembled by ligation to obtain novel combinations of gene sequences.

Any 245, 5283, 2490, 3963 or 4036 gene respectively or any combination of 245, 5283, 2490, 3963 or 4036 genes is used for in vitro recombination in the context of the present invention, for example, a 245, 5283, 2490, 3963 or 4036 gene respectively derived from a plant, such as, e.g. *Arabidopsis thaliana*, e.g. a 245, 5283, 2490, 3963 or 4036 gene respectively set forth in SEQ ID NO:1, SEQ ID NO:3, SEQ ID NO:5, SEQ ID NO:7, or SEQ ID NO:9 respectively, or a 245-like, 5283-like, 2490-like, 3963-like or 4036-like gene respectively from *E. coli* (Craigen et al. (1985) Proc Natl Acad Sci, 82: 3616–3620; Craigen and Caskey (1987) Biochimie, 69: 1031–1041; Ito et al. (1998) Proc Natl Acad Sci, 95: 8165–8169), all of which are incorporated herein by reference. Whole 245, 5283, 2490, 3963 or 4036 genes respectively or portions thereof are used in the context of the present invention. The library of mutated 245, 5283, 2490, 3963 or 4036 genes respectively obtained by the methods described above are cloned into appropriate expression vectors and the resulting vectors are transformed into an appropriate host, for example an algae like Chlamydomonas, a yeast or a bacteria. An appropriate host is preferably a host that otherwise lacks 245, 5283, 2490, 3963 or 4036 activity, for example *E. Coli*. Host cells transformed with the vectors comprising the library of mutated 245, 5283, 2490, 3963 or 4036 genes respectively are cultured on medium that contains inhibitory concentrations of the inhibitor and those colonies that grow in the presence of the inhibitor are selected. Colonies that grow in the presence of normally inhibitory concentrations of inhibitor are picked and purified by repeated restreaking. Their plasmids are purified and the DNA sequences of cDNA inserts from plasmids that pass this test are then determined.

An assay for identifying a modified 245, 5283, 2490, 3963 or 4036 gene respectively that is tolerant to an inhibitor may be performed in the same manner as the assay to identify inhibitors of the 245, 5283, 2490, 3963 or 4036 activity respectively (Inhibitor Assay, above) with the following modifications: First, a mutant 245, 5283, 2490, 3963 or 4036 protein respectively is substituted in one of the reaction mixtures for the wild-type 245, 5283, 2490, 3963 or 4036 protein respectively of the inhibitor assay. Second, an inhibitor of wild-type enzyme is present in both reaction mixtures. Third, mutated activity (activity in the presence of inhibitor and mutated enzyme) and unmutated activity (activity in the presence of inhibitor and wild-type enzyme) are compared to determine whether a significant increase in enzymatic activity is observed in the mutated activity when compared to the unmutated activity. Mutated activity is any measure of activity of the mutated enzyme while in the presence of a suitable substrate and the inhibitor. Unmutated activity is any measure of activity of the wild-type enzyme while in the presence of a suitable substrate and the inhibitor.

In addition to being used to create herbicide-tolerant plants, genes encoding herbicide tolerant 245, 5283, 2490, 3963 or 4036 protein respectively can also be used as selectable markers in plant cell transformation methods. For example, plants, plant tissue, plant seeds, or plant cells transformed with a heterologous DNA sequence can also be transformed with a sequence encoding an altered 245, 5283, 2490, 3963 or 4036 activity respectively capable of being expressed by the plant. The transformed cells are transferred to medium containing an inhibitor of the enzyme in an amount sufficient to inhibit the growth or survivability of plant cells not expressing the modified coding sequence, wherein only the transformed cells will grow. The method is applicable to any plant cell capable of being transformed with a modified 245, 5283, 2490, 3963 or 4036 gene, and can be used with any heterologous DNA sequence of interest. Expression of the heterologous DNA sequence and the modified gene can be driven by the same promoter functional in plant cells, or by separate promoters.

VI. Plant Transformation Technology

A wild type or herbicide-tolerant form of the 245, 5283, 2490, 3963 or 4036 gene respectively, or homologs thereof, can be incorporated in plant or bacterial cells using conventional recombinant DNA technology. Generally, this involves inserting a DNA molecule encoding the 245, 5283, 2490, 3963 or 4036 gene respectively into an expression system to which the DNA molecule is heterologous (i.e., not normally present) using standard cloning procedures known in the art. The vector contains the necessary elements for the transcription and translation of the inserted protein-coding sequences in a host cell containing the vector. A large number of vector systems known in the art can be used, such as plasmids, bacteriophage viruses and other modified viruses. The components of the expression system may also be modified to increase expression. For example, truncated sequences, nucleotide substitutions, nucleotide optimization or other modifications may be employed. Expression systems known in the art can be used to transform virtually any crop plant cell under suitable conditions. A heterologous DNA sequence comprising a wild-type or herbicide-tolerant form of the 245, 5283, 2490, 3963 or 4036 gene respectively is preferably stably transformed and integrated into the genome of the host cells. In another preferred embodiment, the heterologous DNA sequence comprising a wild-type or herbicide-tolerant form of the 245, 5283, 2490, 3963 or 4036 gene respectively located on a self-replicating vector. Examples of self-replicating vectors are viruses, in particular gemini viruses. Transformed cells can be regenerated into whole plants such that the chosen form of the 245, 5283, 2490, 3963 or 4036 gene respectively confers herbicide tolerance in the transgenic plants.

A. Requirements for Construction of Plant Expression Cassettes Gene sequences intended for expression in transgenic plants are first assembled in expression cassettes behind a suitable promoter expressible in plants. The expression cassettes may also comprise any further sequences required or selected for the expression of the heterologous DNA sequence. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described infra. The following is a description of various components of typical expression cassettes.

1. Promoters

The selection of the promoter used in expression cassettes will determine the spatial and temporal expression pattern of the heterologous DNA sequence in the plant transformed with this DNA sequence. Selected promoters will express heterologous DNA sequences in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters known in the art can be used. For example, for constitutive expression, the CaMV 35S promoter, the rice actin promoter, or the ubiquitin promoter may be used. For regulatable expression, the chemically inducible PR-1 promoter from tobacco or Arabidopsis may be used (see, e.g., U.S. Pat. No. 5,689,044).

2. Transcriptional Terminators

A variety of transcriptional terminators are available for use in expression cassettes. These are responsible for the termination of transcription beyond the heterologous DNA sequence and its correct polyadenylation. Appropriate transcriptional terminators are those that are known to function in plants and include the CaMV 35S terminator, the tml terminator, the nopaline synthase terminator and the pea rbcS E9 terminator. These can be used in both monocotyledonous and dicotyledonous plants.

3. Sequences for the Enhancement of Regulation of Expression

Numerous sequences have been found to enhance gene expression from within the transcriptional unit and these sequences can be used in conjunction with the genes of this invention to increase their expression in transgenic plants. For example, various intron sequences such as introns of the maize AdhI gene have been shown to enhance expression, particularly in monocotyledonous cells. In addition, a number of non-translated leader sequences derived from viruses are also known to enhance expression, and these are particularly effective in dicotyledonous cells.

4. Coding Sequence Optimization

The coding sequence of the selected gene optionally is genetically engineered by altering the coding sequence for optimal expression in the crop species of interest. Methods for modifying coding sequences to achieve optimal expression in a particular crop species are well known (see, e.g. Perlak et al., *Proc. Natl. Acad. Sci. USA* 88: 3324 (1991); and Koziel et al., *Bio/technol.* 11: 194 (1993); Fennoy and Bailey-Serres. *Nucl. Acids Res.* 21: 5294–5300 (1993). Methods for modifying coding sequences by taking into account codon usage in plant genes and in higher plants, green algae, and cyanobacteria are well known (see table 4 in: Murray et al. *Nucl. Acids Res.* 17: 477–498 (1989); Campbell and Gowri *Plant Physiol.* 92: 1–11(1990).

5. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104–15109 (1988)). Other gene products are localized to other organelles such as the mitochondrion and the peroxisome (e.g. Unger et al. Plant Molec. Biol. 13: 411–418 (1989)). The cDNAs encoding these products can also be manipulated to effect the targeting of heterologous products encoded by DNA sequences to these organelles. In addition, sequences have been characterized which cause the targeting of products encoded by DNA sequences to other cell compartments. Amino terminal sequences are responsible for targeting to the ER, the apoplast, and extracellular secretion from aleurone cells (Koehler & Ho, Plant Cell 2: 769–783 (1990)). Additionally, amino terminal sequences in conjunction with carboxy terminal sequences are responsible for vacuolar targeting of gene products (Shinshi et al. Plant Molec. Biol. 14: 357–368 (1990)). By the fusion of the appropriate targeting sequences described above to heterologous DNA sequences of interest it is possible to direct this product to any organelle or cell compartment.

B. Construction of Plant Transformation Vectors

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra. Gene 19: 259–268 (1982); Bevan et al., Nature 304:184–187 (1983)), the bar gene, which confers resistance to the herbicide phosphinothricin (White et al., Nucl. Acids Res 18: 1062 (1990), Spencer et al. Theor. Appl. Genet 79: 625–631 (1990)), the hph gene, which confers resistance to the antibiotic hygromycin (Blochinger & Diggelmann, Mol Cell Biol 4: 2929–2931), and the dhfr gene, which confers resistance to methotrexate (Bourouis et al., EMBO J. 2(: 1099–1104 (1983)), and the EPSPS gene, which confers resistance to glyphosate (U.S. Pat. Nos. 4,940,935 and 5,188,642).

1. Vectors Suitable for Agrobacterium Transformation

Many vectors are available for transformation using *Agrobacterium tumefaciens*. These typically carry at least one T-DNA border sequence and include vectors such as pBIN19 (Bevan, Nucl. Acids Res. (1984)). Typical vectors suitable for Agrobacterium transformation include the binary vectors pCIB200 and pCIB2001, as well as the binary vector pCIB10 and hygromycin selection derivatives thereof. (See, for example, U.S. Pat. No. 5,639,949).

2. Vectors Suitable for non-Agrobacterium Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on Agrobacterium include transformation via particle bombardment, protoplast uptake (e.g. PEG and electroporation) and microinjection. The choice of vector depends largely on the preferred selection for the species being transformed. Typical vectors suitable for non-Agrobacterium transformation include pCIB3064, pSOG19, and pSOG35. (See, for example, U.S. Pat. No. 5,639,949).

C. Transformation Techniques

Once the coding sequence of interest has been cloned into an expression system, it is transformed into a plant cell. Methods for transformation and regeneration of plants are well known in the art. For example, Ti plasmid vectors have been utilized for the delivery of foreign DNA, as well as direct DNA uptake, liposomes, electroporation, microinjection, and microprojectiles. In addition, bacteria from the genus Agrobacterium can be utilized to transform plant cells.

Transformation techniques for dicotyledons are well known in the art and include Agrobacterium-based techniques and techniques that do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. In each case the transformed cells are regenerated to whole plants using standard techniques known in the art.

Transformation of most monocotyledon species has now also become routine. Preferred techniques include direct gene transfer into protoplasts using PEG or electroporation techniques, particle bombardment into callus tissue, as well as Agrobacterium-mediated transformation.

D. Plastid Transformation

In another preferred embodiment, a nucleotide sequence encoding a polypeptide having 245, 5283, 2490, 3963, or 4036 activity is directly transformed into the plastid genome. Plastid expression, in which genes are inserted by homologous recombination into the several thousand copies of the circular plastid genome present in each plant cell, takes advantage of the enormous copy number advantage over nuclear-expressed genes to permit expression levels that can readily exceed 10% of the total soluble plant protein. In a preferred embodiment, the nucleotide sequence is inserted into a plastid targeting vector and transformed into the plastid genome of a desired plant host. Plants homoplasmic for plastid genomes containing the nucleotide sequence are obtained, and are preferentially capable of high expression of the nucleotide sequence.

Plastid transformation technology is for example extensively described in U.S. Pat. Nos. 5,451,513, 5,545,817, 5,545,818, and 5,877,462 in PCT application no. WO 95/16783 and WO 97/32977, and in McBride et al. (1994) Proc. Natl. Acad. Sci. USA 91, 7301–7305, all incorporated herein by reference in their entirety. The basic technique for plastid transformation involves introducing regions of cloned plastid DNA flanking a selectable marker together with the nucleotide sequence into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Natl. Acad. Sci. USA 87, 8526–8530; Staub, J. M., and Maliga, P. (1992) Plant Cell 4, 39–45). The presence of cloning sites between these markers allowed creation of a plastid targeting vector for introduction of foreign genes (Staub, J. M., and Maliga, P. (1993) EMBO J. 12, 601–606). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P. (1993) *Proc. Natl. Acad. Sci. USA* 90, 913–917). Other selectable markers useful for plastid transformation are known in the art and encompassed within the scope of the invention.

VII. Breeding

The wild-type or altered form of a 245, 5283, 2490, 3963 or 4036 gene respectively of the present invention can be utilized to confer herbicide tolerance to a wide variety of plant cells, including those of gymnosperms, monocots, and dicots. Although the gene can be inserted into any plant cell falling within these broad classes, it is particularly useful in crop plant cells, such as rice, wheat, barley, rye, corn, potato, carrot, sweet potato, sugar beet, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane.

The high-level expression of a wild-type 245, 5283, 2490, 3963 or 4036 gene respectively and/or the expression of herbicide-tolerant forms of a 245, 5283, 2490, 3963 or 4036 gene respectively conferring herbicide tolerance in plants, in combination with other characteristics important for production and quality, can be incorporated into plant lines through breeding approaches and techniques known in the art.

Where a herbicide tolerant 245, 5283, 2490, 3963 or 4036 gene allele respectively is obtained by direct selection in a crop plant or plant cell culture from which a crop plant can be regenerated, it is moved into commercial varieties using traditional breeding techniques to develop a herbicide tolerant crop without the need for genetically engineering the allele and transforming it into the plant.

The invention will be further described by reference to the following detailed examples. These examples are provided for purposes of illustration only, and are not intended to be limiting unless otherwise specified.

EXAMPLES

Standard recombinant DNA and molecular cloning techniques used here are well known in the art and are described by Sambrook, et al., *Molecular Cloning*, eds., Cold Spring Harbor Laboratory Press, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987), Reiter, et al., *Methods in Arabidopsis Research*, World Scientific Press (1992), and Schultz et al., *Plant Molecular Biology Manual*, Kluwer Academic Publishers (1998). These references describe the standard techniques used for all steps in tagging and cloning genes from T-DNA mutagenized populations of Arabidopsis: plant infection and transformation; screening for the identification of seedling mutants; cosegregation analysis; and plasmid rescue.

Example 1

Sequence Analysis of Tagged Seedling—Lethal Line #245 From the T-DNA Mutagenized Population of Arabidopsis The plasmid rescue technique is used to molecularly clone Arabidopsis genomic DNA flanking one or both sides of T-DNA insertions resulting from T-DNA mutagenesis. Plasmids obtained in this manner are analyzed by restriction enzyme digestion to sort the plasmids into classes based on their digestion pattern. For each class of plasmid clone, the DNA sequence is determined. The resulting sequences are analyzed for the presence of non-T-DNA vector sequences. The plasmids recovered from the plasmid rescue protocol are sequenced using the slp346for primer (SEQ ID NO:11). Primer slp346for provides information on the flanking sequence immediately adjacent to the left T-DNA border. Plasmid rescue is validated by PCR of genomic DNA from a homozygote for the 245 mutation. This PCR experiment uses a primer anchored in the predicted flanking sequence and the slp346for primer (anchored in the T-DNA insertion). Finding a PCR product of the size expected based on the sequence of the plasmid rescued clone confirms a valid rescue. The sequence obtained from primer slp346for is used in a BLASTx search against nucleotide sequence databases (Altschul et al. (1990) J Mol. Biol. 215:403–410; Altschul et al. (1997) Nucleic Acids Res. 25: 3389–3402.). The BLAST search results show that the recovered plant flanking sequence shows a high level of similarity to numerous prokaryotic peptide release factor two proteins. The BLAST results indicate that the T-DNA insertion has occurred in the ORF of the first identified plant derived peptide release factor two.

A DNA fragment that includes peptide release factor sequence similarity is isolated by amplification of Arabidopsis genomic DNA using the polymerase chain reaction. This fragment is used to probe an Arabidopsis cDNA library in the λYES vector (Elledge et al. (1991) Proc. Natl. Acad. Sci. 88:1731–1735). Positive phage clones are isolated and characterized using standard molecular biology techniques. The resultant cDNA clones are excised from the phage and the nucleotide sequence is determined. The DNA sequence is shown in SEQ ID NO:1. The deduced amino acid sequence is analyzed using the BLASTx search against nucleotide sequence databases (Altschul et al. (1990) J Mol. Biol. 215:403–410; Altschul et al. (1997) Nucleic Acids Res. 25: 3389–3402). The BLAST search results show that the recovered 245 cDNA shows sequence similarity to the same set of prokaryotic peptide release factors.

Example 2

Sequence Analysis of Tagged Seedling—Lethal Line #5283 From the T-DNA Mutagenized Population of Arabidopsis The plasmid rescue technique is used to molecularly clone Arabidopsis genomic DNA flanking one or both sides of T-DNA insertions resulting from T-DNA mutagenesis. Plasmids obtained in this manner are analyzed by restriction enzyme digestion to sort the plasmids into classes based on their digestion pattern. For each class of plasmid clone, the DNA sequence is determined. The resulting sequences are analyzed for the presence of non-T-DNA vector sequences. The plasmids recovered from the plasmid rescue protocol are sequenced using the slp346for primer (SEQ ID NO:11). Primer slp346for provides information on the flanking sequence immediately adjacent to the left T-DNA border. Plasmid rescue is validated by PCR of genomic DNA from a heterozygote for the 5283 mutation. This PCR experiment uses a primer anchored in the predicted flanking sequence and the slp328 primer (SEQ ID NO:15) (anchored in the T-DNA insertion). Finding a PCR product of the size expected based on the sequence of the plasmid rescued clone confirms a valid rescue.

The sequence obtained from primer SLP346for is used in a BLASTn search against nucleotide sequence databases (Altschul et al. (1990) J Mol. Biol. 215:403–410; Altschul et al. (1997) Nucleic Acids Res. 25: 3389–3402.). The BLAST search results show that the recovered sequence is identical to genomic DNA located in Arabidopsis chromosome I, BAC T13D8 (Genbank accession number AC004473). Primer LW60 (SEQ ID NO:16), the reverse complement to nucleotides #32,964–32,987 in the BAC T13D8 sequence (5'-aaacgcttaccatatctctttcta-3'), is designed and used to determine the sequence downstream of the T-DNA insert; this experiment identifies the junction of the right border. The region of genomic DNA where the T-DNA insertion occurred includes bases #32,879 through #32,885 of the annotated BAC T13D8 sequence, resulting in a six-base deletion. This insertion occurs 90 nucleotides upstream of the sequence annotated on BAC T13D8 as encoding a protein similar to S. cerevisiae SIK1P protein (Genbank accession number U20237). A DNA fragment that includes bases #33,025 through bases #34,338 of the BAC T13D8 sequence is isolated by amplification of Arabidopsis genomic DNA using the polymerase chain reaction. This fragment is used to probe an Arabidopsis cDNA library in the 1YES vector (Elledge et al. (1991) Proc. Natl. Acad. Sci. 88:1731–1735). Positive phage clones are isolated and characterized using standard molecular biology techniques. The resultant cDNA clones are excised from the phage and the nucleotide sequence is determined. One full-length clone is identified. The deduced amino acid sequence is analyzed using the tBLASTn search against nucleotide sequence databases (Altschul et al. (1990) J Mol. Biol. 215:403–410; Altschul et al. (1997) Nucleic Acids Res. 25: 3389–3402). The BLAST search results show that the recovered 5283 cDNA sequence is derived from the same genomic sequence located in Arabidopsis chromosome I, BAC T13D8. The intron/exon boundaries of the cDNA sequence are the same as those predicted for the Arabidopsis SIK1P homolog (Genbank accession number AC004473), with the following exceptions. The initiator codon for the 5283 cDNA is encoded by bases #32975 through #32977, followed immediately by an intron at bases #32978 through #33199.

Example 3

Sequence Analysis of Tagged Seedling—Lethal Line #2490 From the T-DNA Mutagenized Population of Arabidopsis The plasmid rescue technique is used to molecularly clone Arabidopsis genomic DNA flanking one or both sides of T-DNA insertions resulting from T-DNA mutagenesis. Plasmids obtained in this manner are analyzed by restriction enzyme digestion to sort the plasmids into classes based on their digestion pattern. For each class of plasmid clone, the DNA sequence is determined. The resulting sequences are analyzed for the presence of non-T-DNA vector sequences. The plasmids recovered from the plasmid rescue protocol are sequenced using the SLP346for primer (5' GCGGACATCTACATTTTTGA 3': SEQ ID NO:11). Primer SLP346for provides information on the flanking sequence immediately adjacent to the left T-DNA border. Clones for both ends of the T-DNA insertion are recovered as plasmids containing left T-DNA border. Plasmid rescue is validated by Southern blot analysis comparing genomic DNA from a plant heterozygous for the 2490 mutation with genomic DNA from a plant homozygous for the wild-type 2490 gene. The probe for the Southern blot is prepared from a PCR product generated with the SLP369 (5' CAGACCACAATACCTTCAAAAATA 3': SEQ ID NO:22) and SLP370 (5' CCATTGTGTCTCCCTCCCGCTGTT 3': SEQ ID NO:23) primers. Finding an additional BamH1 fragment in the 2490 heterozygote confirms a valid rescue.

The sequences obtained from the above clones are used in a BLASTn search against nucleotide sequence databases (Altschul et al. (1990) J Mol. Biol. 215: 403–410; Altschul et al (1997) Nucleic Acids Res. 25: 3389–3402). The search results show that the recovered sequences are identical to genomic DNA from Arabidopsis chromosome 5 P1 clone MTG13 (Genbank #AB008270). When the region of genomic DNA where the insertion event occurred is used in a BLASTn search of the Genbank EST database, four sequences derived from the ends of two ESTs, 144K24 (144K24 T7 Genbank #T76608 and 144K24XP Genbank #AA404903) and GBGF153 (5' end Genbank #F15182 and 3' end Genbank #F15181) are identified. The complete sequence of the 144K24 EST is determined and this sequence encodes the full open reading frame (ORF) for the 2490 gene. BLAST analysis of this EST indicates that the 2490 protein has sequence similarity with the Brassica napus Toc36 protein (Genbank #X79091; Ko et al. (1995) The Journal of Biological Chem. 270: 28601–28608; Wu et al. (1994) The Journal of Biological Chem. 269: 32264–32271; Pang et al. (1997) The Journal of Biological Chem. 272: 25623–25627). The Toc36 protein has also been referred to as bce44B, Com44, and Cim44. Because the genomic DNA that contains the 2490 ORF was not annotated correctly until now, the inventors are the first to provide experimental documentation of the correct ORF and sequence similarity for the 2490 gene.

Example 4

Sequence Analysis of Tagged Seedling—Lethal Line #3963 From the T-DNA Mutagenized Population of Arabidopsis The plasmid rescue technique is used to molecularly clone Arabidopsis genomic DNA flanking one or both sides of T-DNA insertions resulting from T-DNA mutagenesis. Plasmids obtained in this manner are analyzed by restriction enzyme digestion to sort the plasmids into classes based on their digestion pattern. For each class of plasmid clone, the DNA sequence is determined. The resulting sequences are analyzed for the presence of non-T-DNA vector sequences. The plasmids recovered from the plasmid rescue protocol are sequenced using the –21 primer (5' TGTAAAACGACGGCCAGT 3'; SEQ ID NO:25). Primer –21 provides information on the flanking sequence immediately adjacent to the right T-DNA border. Plasmid rescue is validated by PCR of genomic DNA from a heterozygote for the 3963 mutation. This PCR experiment uses a primer anchored in the predicted flanking sequence and the –21 primer (anchored in the T-DNA insertion). Finding a PCR product of the size expected based on the sequence of the plasmid rescued clone confirms a valid rescue. The sequence obtained from primer –21 is used in a BLASTn search against nucleotide sequence databases (Altschul et al. (1990) J Mol. Biol. 215:403–410; Altschul et al. (1997) Nucleic Acids Res. 25: 3389–3402.). The BLAST search results show that the recovered plant flanking sequence is 100% identical to the genomic sequence for P1 clone MDK4 on chromosome 5 (Genbank accession number AB010695). The T-DNA insertion occurred at base #36342 of the annotated P1 clone MDK4 sequence, in the gene identified as MDK4.6. A tBLASTX analysis of the recovered flanking sequence shows sequence similarity to Mre11p, a DNA repair protein from Sacchro-

*myces cerevisiae* (Genbank accession number U60829). A fragment that encodes part of the Arabidopsis 3963 protein is isolated by amplification of Arabidopsis genomic DNA using the polymerase chain reaction. This fragment is used to probe an Arabidopsis cDNA library in the λYES vector (Elledge et al. (1991) Proc. Natl. Acad. Sci. 88:1731–1735). Positive phage clones are isolated and characterized using standard molecular biology techniques. The resultant cDNA clones are excised from the phage and the nucleotide sequence is determined. One cDNA clone is identified. The cDNA sequence is shown in SEQ ID NO:7. The deduced amino acid sequence is analyzed using the BLASTx search against nucleotide sequence databases (Altschul et al. (1990) J Mol. Biol. 215:403–410; Altschul et al. (1997) Nucleic Acids Res. 25: 3389–3402). The BLAST search results show that the recovered 3963 cDNA shows sequence similarity to a number of DNA repair proteins, including Rad32p from *Schizosaccharomyces pombe* (Genbank accession numberQ09683); hMre11 from *Homo sapiens* (Genbank accession number U37359); and Mre11p from *Saccharomyces cerevisiae* (Genbank accession number U60829). Because the genomic DNA that contains the 3963 Open Reading Frame (ORF) was not annotated correctly in the prior art with respect to the exon/intron boundaries, the inventors are the first to provide experimental documentation of the correct ORF for the 3963 gene. The prior art indicates these exon/intron boundaries: 35662–35817, 36015–36172, 36315–36405, 36528–36647, 36728–36796, 36865–36956, 37045–37147, 37247–37354, 37476–37538, 37785–37862, 38060–38122, 38211–38271, 38753–38835, 38979–39092, 39468–39766, 39879–40002, 40161–40370. The exon/intron boundaries corresponding to the partial cDNA disclosed herein are: missing 5' end (first known base at 36147), 36147–36172, 36315–36405, 36528–36647, 36728–36796, 36865–36956, 37045–37147, 37247–37354, 37476–37538, 37610–37681, 37785–39092, 39212–39290, 39377–39445, 39532–39776, 39879–40002, 40161–40363, 40478–40508 (stop begins at 40509).

Example 5

Sequence Analysis of Tagged Seedling—Lethal Line #4036 From the T-DNA Mutagenized Population of Arabidopsis The plasmid rescue technique is used to molecularly clone Arabidopsis flanking DNA from one or both sides of the T-DNA insertions resulting from T-DNA mutagenesis. Plasmids obtained in this manner are analyzed by restriction enzyme digestion to sort the plasmids into classes based on their digestion pattern. For each class of plasmid clone, the DNA sequence is determined. The resulting sequences are analyzed for the presence of nonT-DNA vector sequences. The plasmids recovered from the plasmid rescue protocol are sequenced using the slp346 primer (5' GCGGACATCTACATTTTTGA 3'; SEQ ID NO:11). Primer slp346 provides information on the flanking sequence immediately adjacent to the left T-DNA border. The plasmid rescue is validated via PCR of template genomic DNA from a heterozygote for the 4036 insertion mutation. The experiment uses a primer anchored in the predicted flanking sequence and the slp328 primer (5' ACCTTAGGCGACTTTTGAAC 3'; SEQ ID NO:15; anchored in the T-DNA insertion). Finding a PCR product of the size expected based on the sequence of the plasmid rescue clone confirms a valid rescue.

The sequence obtained from the above clone is used in a BLASTn search against nucleotide databases (Altschul et al. (1990) J Mol. Biol. 215:403–410; Altschul et al. (1997) Nucleic Acids Res. 25;3389–3402). The BLAST results show that the plant flanking sequence is 100% identical to published genomic sequence of P1 MQB2, from chromosome 5 of Arabidopsis (Genbank accession #AB009053). The T-DNA insertion occurred at base 31,380 of the annotated P1 clone and interrupts a gene identified as MQB2.6. The protein encoded by the interrupted open reading frame (ORF) shows similarity to 1-deoxy-D-xylulose 5-phosphate reductoisomerase from a number of organisms including Synechocystis sp. (SWISS-PROTQ55663), *Bacillus subtilis* (SWISS-PROT 031753), and *Escherichia coli* (SWISS-PROT P45568) (Takahashi et al. (1998) Proc. Natl. Acad. Sci. USA, 95: 9879–9884). The genomic region encompassing the ORF is re-annotated with Web GeneMark software (Borodovsky, M. and Mclninch J. (1993) Computers & Chemistry, 17: 123–133). Primers are then designed to the 5' and 3' ends of the predicted ORF, and PCR is performed using DNA from the pFL61 Arabidopsis cDNA library (Minet et al. (1992) Plant J. 2: 417–422) as the template. The resulting PCR product is TA-ligated and cloned (Original TA Cloning Kit, Invitrogen), and sequenced. Because the genomic DNA that contains the 4036 ORF was not annotated correctly in the prior art with respect to the exon/intron boundaries, the inventors are the first to provide experimental documentation of the correct ORF for the 4036 gene.

The prior art indicates these exon/intron boundaries: 33490 . . . 33356, 31293 . . . 31207, 30971 . . . 30846, 30780 . . . 30718, 30622 . . . 30473, 30345 . . . 30288, 30194 . . . 30083, 29996 . . . 29892, 29805 . . . 29684, 29394 . . . 29248, 29162 . . . 28997. In the sequence of the present invention, base 31928 marks the first base of the cDNA's start codon and base 28996 marks the first base of the cDNA's stop codon. The 3' end of the exon containing the start codon is 31836, and the 5' end of the exon containing the stop codon is 29161. The internal exon/intron boundaries for the cDNA disclosed herein are: 31640 . . . 31448, 31294 . . . 31202, 30965 . . . 30843, 30777 . . . 30722, 30636 . . . 30473, 30355 . . . 30287, 30193 . . . 30082, 29995 . . . 29891, 29804 . . . 29684, 29394 . . . 29247.

Example 6a

Expression of Recombinant 245 Protein in *E. coli*

The coding region of the protein, corresponding to the cDNA clone SEQ ID NO:1, is subcloned into previously described expression vectors, and transformed into *E. coli* using the manufacturer's conditions. Specific examples include plasmids such as pBluescript (Stratagene, La Jolla, Calif.), pFLAG (International Biotechnologies, Inc., New Haven, Conn.), and pTrcHis (Invitrogen, La Jolla, Calif.). *E. coli* is cultured, and expression of the 245 activity is confirmed. Protein conferring 245 activity is isolated using standard techniques.

Example 6b

Expression of Recombinant 5283 Protein in *E. coli*

The coding region of the protein, corresponding to the cDNA clone SEQ ID NO:3, is subcloned into previously described expression vectors, and transformed into *E. coli* using the manufacturer's conditions. Specific examples include plasmids such as pBluescript (Stratagene, La Jolla, Calif.), pFLAG (International Biotechnologies, Inc., New Haven, Conn.), and pTrcHis (Invitrogen, La Jolla, Calif.). *E. coli* is cultured, and expression of the 5283 activity is confirmed. Protein conferring 5283 activity is isolated using standard techniques.

Example 6c

Expression of Recombinant 2490 Protein in E. coli

The coding region of the protein, corresponding to the cDNA clone SEQ ID NO:5, is subcloned into previously described expression vectors, and transformed into E. coli using the manufacturer's conditions. Specific examples include plasmids such as pBluescript (Stratagene, La Jolla, Calif.), pFLAG (International Biotechnologies, Inc., New Haven, Conn.), and pTrcHis (Invitrogen, La Jolla, Calif.). E. coli is cultured, and expression of the 2490 activity is confirmed. Protein conferring 2490 activity is isolated using standard techniques.

Example 6d

Expression of Recombinant 3963 Protein in E. coli

The coding region of the protein, corresponding to the cDNA clone SEQ ID NO:7, is subcloned into previously described expression vectors, and transformed into E. coli using the manufacturer's conditions. Specific examples include plasmids such as pBluescript (Stratagene, La Jolla, Calif.), pFLAG (International Biotechnologies, Inc., New Haven, Conn.), and pTrcHis (Invitrogen, La Jolla, Calif.). E. coli is cultured, and expression of the 3963 activity is confirmed. Protein conferring 3963 activity is isolated using standard techniques.

Example 6e

Expression of Recombinant 4036 Protein in E. coli

The coding region of the protein, corresponding to the cDNA clone SEQ ID NO:9, is subcloned into previously described expression vectors, and transformed into E. coli using the manufacturer's conditions. Specific examples include plasmids such as pBluescript (Stratagene, La Jolla, Calif.), pFLAG (International Biotechnologies, Inc., New Haven, Conn.), and pTrcHis (Invitrogen, La Jolla, Calif.). E. coli is cultured, and expression of the 4036 activity is confirmed. Protein conferring 4036 activity is isolated using standard techniques.

Example 7

In vitro Recombination of 245, 5283, 2490, 3963, or 4036 Genes by DNA Shuffling The nucleotide sequence of SEQ ID NO:1, SEQ ID NO:3, SEQ ID NO:5, SEQ ID NO:7, or SEQ ID NO:9, respectively, is amplified by PCR. The resulting DNA fragment is digested by DNaseI treatment essentially as described (Stemmer et al. (1994) PNAS 91: 10747–10751) and the PCR primers are removed from the reaction mixture. A PCR reaction is carried out without primers and is followed by a PCR reaction with the primers, both as described (Stemmer et al. (1994) PNAS 91: 10747–10751). The resulting DNA fragments are cloned into pTRC99a (Pharmacia, Cat no: 27-5007-01) for use in bacteria, or into pESC vectors (Stratagene Catalog) for use in yeast; and transformed into a bacterial or yeast strain deficient in 245, 5283, 2490, 3963, or 4036 activity, respectively, by electroporation using the Biorad Gene Pulser and the manufacturer's conditions. The transformed bacteria or yeast are grown on medium that contains inhibitory concentrations of an inhibitor of 245, 5283, 2490, 3963, or 4036 activity and those colonies that grow in the presence of the inhibitor are selected. Colonies that grow in the presence of normally inhibitory concentrations of inhibitor are picked and purified by repeated restreaking. Their plasmids are purified and the DNA sequences of cDNA inserts from plasmids that pass this test are then determined.

In a similar reaction, PCR-amplified DNA fragments comprising the A. thaliana 245, 5283, 2490, 3963, or 4036 gene, respectively, encoding the protein and PCR-amplified DNA fragments comprising the 245, 5283, 2490, 3963, or 4036 gene, respectively, from E. coli are recombined in vitro and resulting variants with improved tolerance to the inhibitor are recovered as described above.

Example 8a

In vitro Recombination of 245 Genes by Staggered Extension Process

The A. thaliana 245 gene encoding the 245 protein and the E. coli 245 gene are each cloned into the polylinker of a pBluescript vector. A PCR reaction is carried out essentially as described (Zhao et al. (1998) Nature Biotechnology 16: 258–261) using the "reverse primer" and the "M13 −20 primer" (Stratagene Catalog). Amplified PCR fragments are digested with appropriate restriction enzymes and cloned into pTRC99a and mutated 245 genes are screened as described in Example 7.

Example 8b

In vitro Recombination of 5283 Genes by Staggered Extension Process

The A. thaliana 5283 gene encoding the 5283 protein and the E. coli 5283 gene are each cloned into the polylinker of a pBluescript vector. A PCR reaction is carried out essentially as described (Zhao et al. (1998) Nature Biotechnology 16: 258–261) using the "reverse primer" and the "M13 −20 primer" (Stratagene Catalog). Amplified PCR fragments are digested with appropriate restriction enzymes and cloned into pTRC99a and mutated 5283 genes are screened as described in Example 7.

Example 8c

In vitro Recombination of 2490 Genes by Staggered Extension Process

The A. thaliana 2490 gene encoding the 2490 protein and the E. coli 2490 gene are each cloned into the polylinker of a pBluescript vector. A PCR reaction is carried out essentially as described (Zhao et al. (1998) Nature Biotechnology 16: 258–261) using the "reverse primer" and the "M13 −20 primer" (Stratagene Catalog). Amplified PCR fragments are digested with appropriate restriction enzymes and cloned into pTRC99a and mutated 2490 genes are screened as described in Example 7.

Example 8d

In vitro Recombination of 3963 Genes by Staggered Extension Process

The A. thaliana 3963 gene encoding the 3963 protein and the E. coli 3963 gene are each cloned into the polylinker of a pBluescript vector. A PCR reaction is carried out essentially as described (Zhao et al. (1998) Nature Biotechnology 16: 258–261) using the "reverse primer" and the "M13 −20 primer" (Stratagene Catalog). Amplified PCR fragments are digested with appropriate restriction enzymes and cloned into pTRC99a and mutated 3963 genes are screened as described in Example 7.

Example 8e

In vitro Recombination of 4036 Genes by Staggered Extension Process

The *A. thaliana* 4036 gene encoding the 4036 protein and the *E. coli* 4036 gene are each cloned into the polylinker of a pBluescript vector. A PCR reaction is carried out essentially as described (Zhao et al. (1998) Nature Biotechnology 16: 258–261) using the "reverse primer" and the "M13 –20 primer" (Stratagene Catalog). Amplified PCR fragments are digested with appropriate restriction enzymes and cloned into pTRC99a and mutated 4036 genes are screened as described in Example 7.

Example 9

In Vitro Binding Assays

Recombinant 245, 5283, 2490, 3963, or 4036 protein is obtained, for example, according to Example 6a,6b,6c,6d,or 6e, respectively. The protein is immobilized on chips appropriate for ligand binding assays using techniques which are well known in the art. The protein immobilized on the chip is exposed to sample compound in solution according to methods well know in the art. While the sample compound is in contact with the immobilized protein measurements capable of detecting protein-ligand interactions are conducted. Examples of such measurements are SELDI, biacore and FCS, described above. Compounds found to bind the protein are readily discovered in this fashion and are subjected to further characterization.

The above disclosed embodiments are illustrative. This disclosure of the invention will place one skilled in the art in possession of many variations of the invention. All such obvious and foreseeable variations are intended to be encompassed by the appended claims.

What is claimed is:

1. A method of identifying a compound that binds to a polypeptide comprising SEQ ID NO; 10, wherein said compound has herbicidal activity, comprising:

a) combining a polypeptide comprising SEQ ID NO:10 and a compound to be tested for the ability to bind to said polypeptide, under conditions conducive to binding;

b) selecting a compound identified in step (a) that binds to said polypeptide;

c) applying a compound selected in step (b) to a plant to test for herbicidal activity; and d) selecting a compound identified in step (c) that has herbicidal activity.

* * * * *